(12) United States Patent
Strelchenok et al.

(10) Patent No.: US 7,030,158 B2
(45) Date of Patent: Apr. 18, 2006

(54) THERAPEUTIC COMPOUNDS

(75) Inventors: Oleg Strelchenok, Lidingö (SE); Julian Aleksov, Lidingö (SE)

(73) Assignee: Ardenia Investments Ltd., London (GB)

( * ) Notice: Subject to any disclaimer, the term of this patent is extended or adjusted under 35 U.S.C. 154(b) by 147 days.

(21) Appl. No.: 10/295,139

(22) Filed: Nov. 15, 2002

(65) Prior Publication Data

US 2004/0048923 A1    Mar. 11, 2004

Related U.S. Application Data

(60) Provisional application No. 60/398,200, filed on Jul. 23, 2002.

(30) Foreign Application Priority Data

Jul. 23, 2002    (SE) ................... 0202311-7

(51) Int. Cl.
  *C07C 309/23*   (2006.01)
  *C07C 313/04*   (2006.01)
  *A61K 31/19*    (2006.01)
  *A61K 31/215*   (2006.01)

(52) U.S. Cl. ............... 514/550; 514/553; 562/106; 562/126

(58) Field of Classification Search ............ 514/562, 514/550, 553; 562/126, 106
See application file for complete search history.

(56) References Cited

U.S. PATENT DOCUMENTS 6,642,271 B1 * 11/2003 Strelchenok et al. ....... 514/562

FOREIGN PATENT DOCUMENTS

DE    40 32 187 A1    4/1992

OTHER PUBLICATIONS

Arsenov, D.V. et al. (2001) "Synthesis of N-(all-trans-retinoyl) doxorubicin and Study of the Antitumor Activity of its Complex with Blood Serum Proteins" *Pharmaceutical Chemistry Journal* 35 (4): 186-189 (Original and English translation).

* cited by examiner

*Primary Examiner*—Bernard Dentz
(74) *Attorney, Agent, or Firm*—Morrison & Foerster LLP

(57) ABSTRACT

A group of new compounds, N-(all-trans-Retinoyl)-L-cysteic acid, N-(13-cis-Retinoyl)-L-cysteic acid, N-(all-trans-Retinoyl)-L-cysteinesulfinic acid, N-(13-cis-Retinoyl)-L-cysteinesulfinic acid, N-(all-trans-Retinoyl)-L-homocysteic acid, N-(13-cis-Retinoyl)-L-homocysteic acid, and sodium salts of these compounds, including sodium salts of their esters and amides, is shown to exhibit therapeutic effects per se, and which compounds in combination with cytotoxic compounds, such as docetaxel, paclitaxel, doxorubicin and mitoxantrone, exhibit a synergistic effect. These compounds make it possible to manufacture new formulations of poorly soluble pharmaceutical compounds, and the present invention discloses a process of manufacturing water-soluble formulations of such compounds, exemplified by docetaxel, and paclitaxel, exhibiting enhanced pharmacological activity, and formulations of water-soluble pharmaceuticals exemplified by doxorubicin and mitoxantrone, exhibiting improved therapeutic efficacy.

49 Claims, No Drawings

THERAPEUTIC COMPOUNDS

CROSS REFERENCE TO RELATED APPLICATIONS

This application claims priority to U.S. Provisional Patent Application Ser. No. 60/398,200 filed Jul. 23, 2002, and Swedish Patent Application No. SE 0202311-7 filed Jul. 23, 2002, which are hereby incorporated by reference in their entirety.

FIELD OF THE INVENTION

This invention relates to novel compounds having therapeutic properties in themselves, and being capable of potentiating the efficacy of other therapeutically active compounds, for example cytotoxic compounds used in the treatment of cancer. The novel compounds have been shown to possess a cell growth inhibiting property per se. In addition to this, these compounds have surprisingly been found to make it possible to manufacture new formulations of poorly soluble compounds, exemplified here by poorly soluble cytotoxic compounds, such as docetaxel and paclitaxel, the formulations exhibiting improved solubility and therapeutic efficacy. The compounds have also been found to make it possible to manufacture new formulations of other cytotoxic compounds, such as doxorubicin and mitoxantrone, exhibiting improved therapeutic efficacy. Further, the inventive compounds in saline in the presence of calcium, and in particular the corresponding cis- and trans-isoforms of a compound according to the invention have been found to exhibit therapeutic properties.

BACKGROUND OF THE INVENTION

Docetaxel is a representative of the taxoid family. [(2R, 3S)-N-carboxy-3-phenylisoserine, N-tert-butyl ester, 13-ester with 5β-20-epoxy-1,2α, 4,7β,10β, 13α-hexahydroxytax-11-en-9-one 4-acetate 2-benzoate, trihydrate, the active ingredient in Taxotere®, Rhone-Poulenc Rorer, Collegeville, Pa., USA] The compound may be prepared through synthesis from its chemical precursor, naturally present in the renewable needle biomass of yew plants.

Docetaxel is the most effective agent for the treatment of metastatic breast cancer. Currently, practical use has confirmed that docetaxel has high activity also against non-small-cell and small-cell lung, ovarian, head, neck and gastric cancers; as well as melanoma, and soft tissue sarcomas. It promotes the assembly of and stabilizes microtubules and thus inhibits their depolymerization. Docetaxel is highly protein bound, namely, to $\alpha_1$-acid glycoprotein, albumin and lipoproteins. The pharmacokinetic profile is characterized by the initial rapid distribution of docetaxel to the peripheral compartments and in a later phase, the slow efflux of docetaxel from said peripheral compartments.

Docetaxel is highly lipophilic and poorly soluble in water. Taxotere® is a formulation in single-dose vials containing 20 mg (0.5 mL) or 80 mg (2.0 mL) docetaxel (anhydrous). Each ml of this product contains 40 mg docetaxel (anhydrous) and 1040 mg polysorbate 80. The diluent for Taxotere® contains 13% ethanol in water-for-injection.

The safety pattern of Taxotere® includes a premedication regimen. All patients should be premedicated with oral corticosteroids to reduce the severity of fluid retention and hypersensitivity reactions. Other less severe side effects include neurotoxicities, cutaneous reactions, alopecia and asthenia.

Docetaxel is now challenging the role of old agents in the treatment of cancer and is at present approved after failure of other chemotherapy. For example, docetaxel has proven to be the most effective drug against liver metastases. In clinical trials, patients with metastatic breast cancer exhibit response rates for first-line docetaxel treatment at a dose of 100 mg/m$^2$ exceeding those for paclitaxel at doses <250 mg/m$^2$.

The combination of doxorubicin and paclitaxel has entered clinical trials for treatment of patients with breast cancer. There are grounds for assuming that pharmacokinetic interactions between paclitaxel and doxorubicin can intensify anthracycline cardiotoxicity. Docetaxel in contrast has no influence on the pharmacokinetics of doxorubicin. Therefore docetaxel is the number one candidate for use with doxorubicin in clinical trials (C. L. Vogel, J-M. Nabholtz, The Oncologist, 1999, v. 4, p. 17–33; J. E. Cortes, R. Pazdur, J. Clin. Oncology, 1995, v. 13, p. 2643–2655).

Doxorubicin, an anthracycline water-soluble antibiotic, continues to be an important agent of first-line chemotherapy in the treatment of a variety of solid and hematopoieitic tumors. Doxorubicin is isolated from *Streptomyces peucetius* var. *caesius*. The chemical name for doxorubicin is {(8S,10S)-10-[(3-amino-2,3,6-trideoxy-α-L-lyxo-hexopyranosyl)oxy]-8-glycolyl-7,8,9,10-tetrahydro-6,8,11-trihydroxy-1-methoxy-5,12-naphtacenedione hydrochloride, the active ingredient in Adriamycin®, Pharmacia, Sweden}. Adriamycin® contains 50 mg doxorubicin hydrochloride, 250 mg lactose monohydrate, 5 mg methyl para-hydroxybenzoate in dry form.

The efficacy of doxorubicin is complicated by its dose-limiting toxicity, chronic or acute cardiotoxicity and a spontaneous or acquired resistance. It needs to be emphasized that doxorubicin has a certain affinity for phospholipids and the development of resistance appears to be linked to some membrane alterations. At present, the antiproliferative and cytotoxic effects of doxorubicin are believed to be connected with the DNA synthesis inhibition, free radical formation and lipid peroxidation, DNA binding and DNA cross-linking, direct membrane effects.

Trials with incorporation of doxorubicin into combination regimens for the treatment of breast cancer has exhibited modest survival rates for women with metastatic disease.

Drug resistance, both intrinsic and acquired, is fundamental reason for the clinical failure of this compound in breast cancer treatment. Nevertheless, the vast clinical experience gathered so far shows doxorubicin as a well-tolerated and effective drug for most anthracycline-sensitive tumors (D. A. Gewirtz, Biochem. Pharmacol., 1999, v. 57, No. 7, p. 727–741; Vogel and Nabholtz, supra)

Mitoxantrone is a synthetic antracenedione cytotoxic agent derived from the anthraquinone dye ametandrone having structural similarities to doxorubicin. It has a mechanism of action similar to the anthracyclines. Mitoxantrone intercalates in DNA and inhibits DNA synthesis. The drug's antitumor activity is also attributed to its interaction with DNA topoisomerase II.

Mitoxantrone is the active ingredient in Novantrone®, Wyeth Lederle. Novantrone® is a concentrate for infusions, 2 mg/ml. Each ml of concentrate contains 2 mg mitoxantrone hydrochloride, 8 mg sodium chloride, 0.05 mg sodium acetate, 0.46 mg acetic acid, and 0.15 mg sodium sulfate. Mitoxantrone exhibits clinical efficacy in the treatment of leukemia, lymphoma and breast cancer. It is also effective for palliative treatment of hepatic, advanced ovarian carcinoma and hormone-resistant prostate cancer.

The cumulative doses of mitoxantrone can provoke cardiotoxicity and immunosuppresion. Patients having a history of anthracycline therapy can suffer from congestive heart failure (D. Faulds et al., Drugs, 1991, v. 41, No. 3, p. 400–449).

The modern trends in the combat of cancer are challenging the main role of monotherapy in the treatment of patients. Clinical experience suggests a great potential of combination therapy in the adjuvant setting. The creation of effective therapeutic options for the adjuvant setting however requires the development of a new formulation strategy for water insoluble compounds, in order to maximize the potential of the drugs.

In the last years, drug formulations based on nutritional emulsion products have been used. Such formulations need to be adjusted with significant drug loading and to be supplemented by emulsifiers. The formulations must be strictly specified in droplet size distribution. This complicates manufacturing and requires high-pressure homogenization of the lipid emulsions. Moreover, several technical issues need to be addressed, such as the long-term stability and the elimination of the possibility of drug precipitation upon dilution (L. Collins-Gold, et al., Modem Drug Discovery, 2000, Vol. 3, No. 3, p. 44–46, 48).

In co-pending applications (U.S. Ser. No. 10/098,873 and PCT/SE02/00380) the present inventors have disclosed N-Retinoyl-L-cysteic acid, N-Retinoyl-L-homocysteic acid, N-Retinoyl-L-cysteinesulfinic acid, as well as sodium salts of these compounds.

In the present patent application, the inventors disclose novel isoforms of N-Retinoyl-L-cysteic acid, N-Retinoyl-L-homocysteic acid, N-Retinoyl-L-cysteinesulfinic acid, their esters and amides, as well as salts thereof. These novel compounds exhibit cell growth inhibiting properties and in addition to this, also make it possible to manufacture new micellar formulations of poorly water soluble cytotoxic compounds, such as paclitaxel and docetaxel, exhibiting improved solubility and therapeutical efficacy and new micellar formulations of doxorubicin and mitoxantrone, demonstrating improved therapeutic efficacy.

SHORT SUMMARY OF THE INVENTION

The present invention makes available a group of new compounds as defined in the claims attached hereto; N-(all-trans-Retinoyl)-L-cysteic acid (I-1), N-(13-cis-Retinoyl)-L-cysteic acid (II-1), N-(all-trans-Retinoyl)-L-cysteinesulfinic acid (I-2), N-(13-cis-Retinoyl)-L-cysteinesulfinic acid (II-2), N-(all-trans-Retinoyl)-L-homocysteic acid (I-3), N-(13-cis-Retinoyl)-L-homocysteic acid (II-3) and sodium salts of these compounds and also sodium salts of their esters and amides, which exhibit therapeutic effects per se, and which in combination with cytotoxic compounds, such as docetaxel, paclitaxel, doxorubicin and mitoxantrone, exhibit a synergistic effect. Further, the present invention discloses methods of manufacturing water-soluble formulations of poorly soluble pharmaceuticals, such as docetaxel, and paclitaxel, exhibiting enhanced pharmacological activity, and the formulations of water-soluble pharmaceuticals such as doxorubicin and mitoxantrone, exhibiting improved therapeutic efficacy. The invention also makes available methods for the treatment of cancer wherein the inventive compounds and the formulations are administered to patients in aqueous medium of abundant sodium ions containing calcium ions. The present invention also makes available a novel pharmaceutical composition comprising at least one of the inventive compounds in saline solution in the presence of calcium, and preferably two corresponding cis- and trans isoforms of one of said compounds, said isoforms capable of forming a complex with calcium.

DESCRIPTION OF THE INVENTION

In co-pending applications (U.S. Ser. No. 10/098,873 and PCT/SE02/00380) the present inventors have shown that N-(all-trans-Retinoyl)-L-cysteic acid (I-1), N-(13-cis-Retinoyl)-L-cysteic acid (II-1), N-(all-trans-Retinoyl)-L-cysteinesulfinic acid (I-2), N-(13-cis-Retinoyl)-L-cysteinesulfinic acid (II-2), N-(all-trans-Retinoyl)-L-homocysteic acid (I-3) and N-(13-cis-Retinoyl)-L-homocysteic acid (II-3) are capable of increasing the solubility of paclitaxel, as well as potentiating its therapeutic efficacy.

Now the inventors have surprisingly found that sodium salts of a group of novel esters (I-1a–I-1e, I-3a; II-1a–I-1e, II-3b) and sodium salts of amides (I-1f–I-1h, I-3f, II-1f) of these compounds possess the same properties.

The general structural formulas of these compounds and the structural formulas of each synthesized compound are presented below:

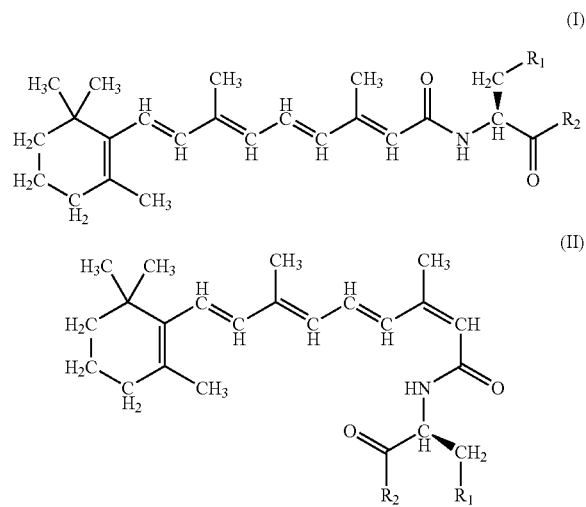

wherein

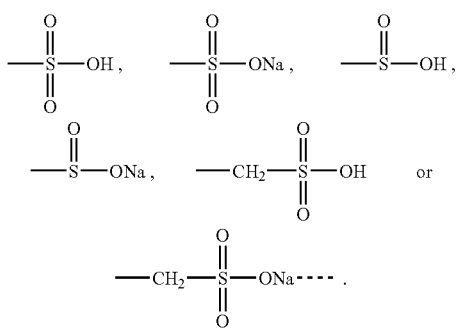

and R2 is selected from OH, ONa, NH$_2$, NHCH$_3$, N(CH$_3$)$_2$, OX wherein X is C$_1$–C$_5$ alkyl.

Individual compounds, falling within the scope of the above general formula, have been synthesized by the inventors, and derivatives prepared thereof. Examples of these compounds are given below.

First, a group of N-(all-trans-retinoyl)-L-cysteic acid derivatives is exemplified:

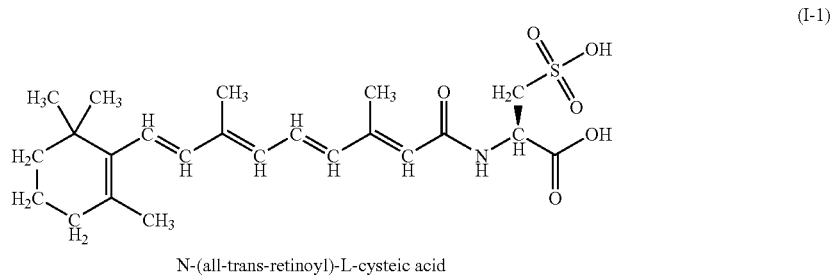

N-(all-trans-retinoyl)-L-cysteic acid (I-1)

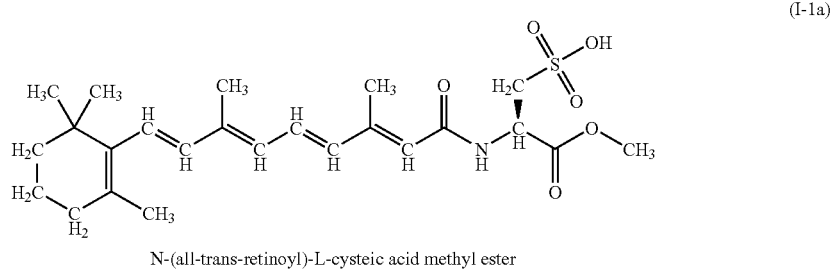

N-(all-trans-retinoyl)-L-cysteic acid methyl ester (I-1a)

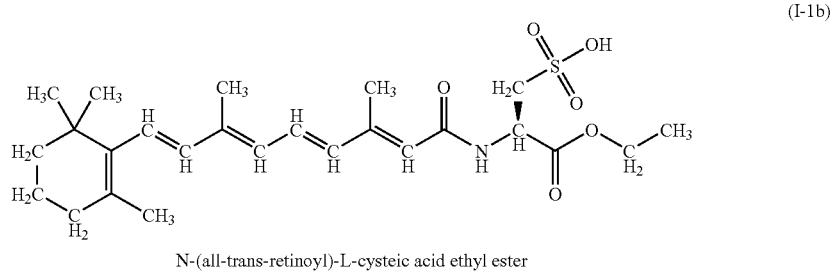

N-(all-trans-retinoyl)-L-cysteic acid ethyl ester (I-1b)

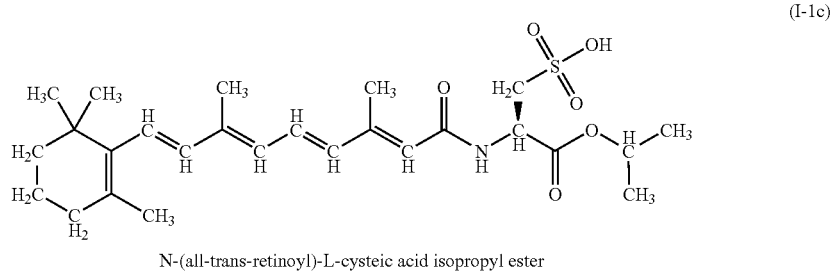

N-(all-trans-retinoyl)-L-cysteic acid isopropyl ester (I-1c)

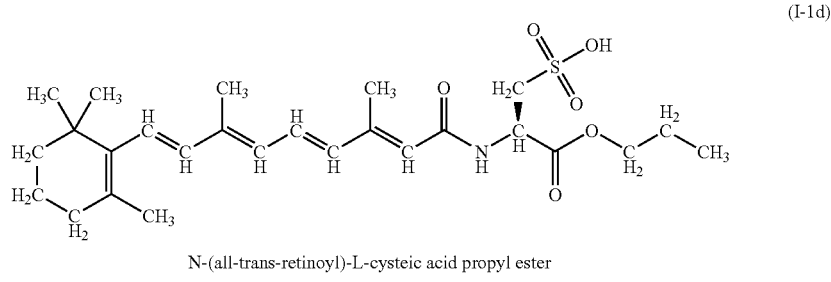

N-(all-trans-retinoyl)-L-cysteic acid propyl ester (I-1d)

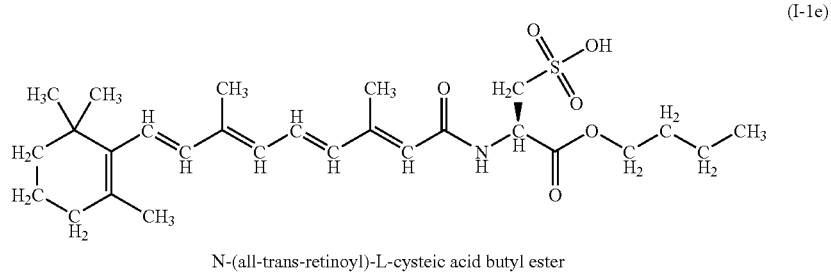

N-(all-trans-retinoyl)-L-cysteic acid butyl ester (I-1e)

-continued

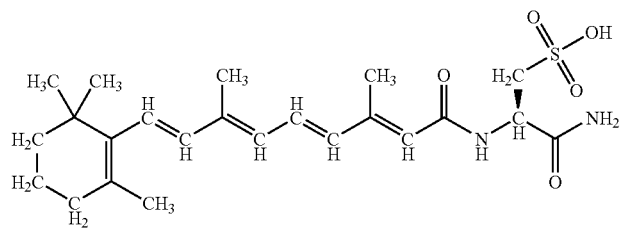
N-(all-trans-retinoyl)-L-cysteic acid amide (I-1f)

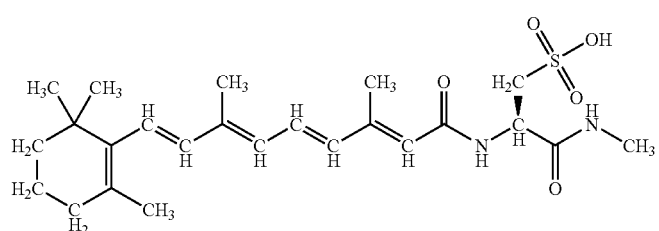
N-(all-trans-retinoyl)-L-cysteic acid methylamide (I-1g)

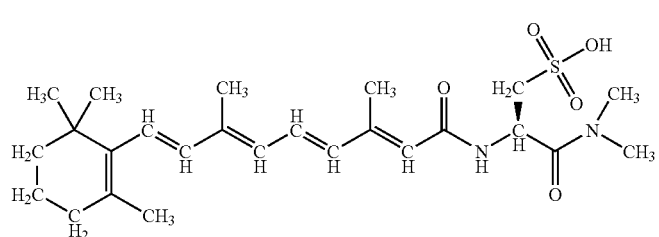
N-(all-trans-retinoyl)-L-cysteic acid dimethylamide (I-1h)

The invention also includes sodium salts of these compounds (I-1, I-1a through I-1h) exemplified above, as well as sodium salts of all compounds covered by the general formula.

The invention also encompasses the following compound (I-2) and derivatives thereof:

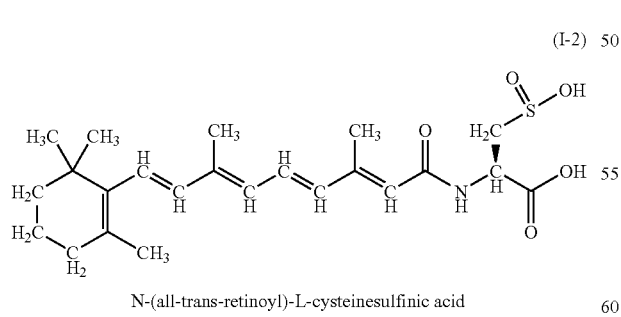
N-(all-trans-retinoyl)-L-cysteinesulfinic acid (I-2)

The invention also includes sodium salt of the above compound (I-2).

The invention also encompasses the following group of compounds (I-3, I-3a, I-3f) and derivatives thereof:

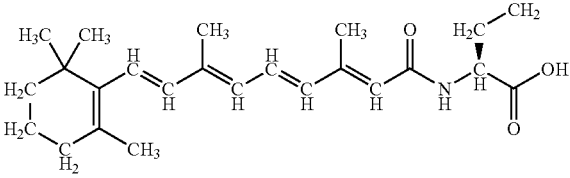
N-(all-trans-retinoyl)-L-homocysteic acid (I-3)

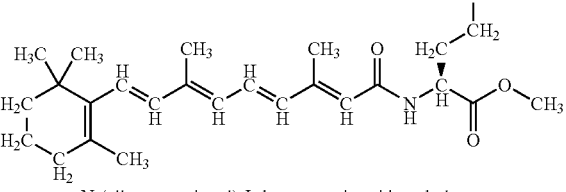
N-(all-trans-retinoyl)-L-homocysteic acid methyl ester (I-3a)

(I-3f)

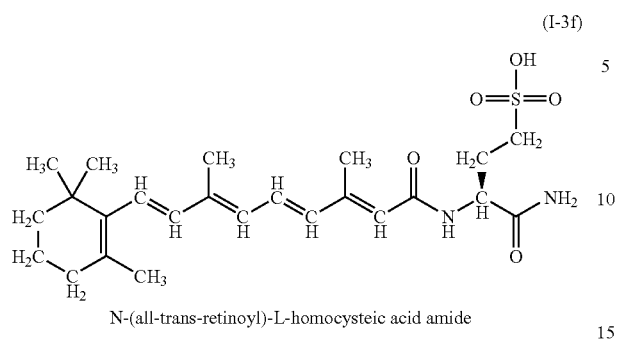

N-(all-trans-retinoyl)-L-homocysteic acid amide

The invention also includes sodium salts of these compounds (I-3, I-3a, I-3f) exemplified above, as well as sodium salts of all compounds covered by the general formula.

Further, the invention encompasses a group of N-(13-cis-retinoyl)-L-cysteic acid derivatives (II-1, II-1a through II-1f):

(II-1)

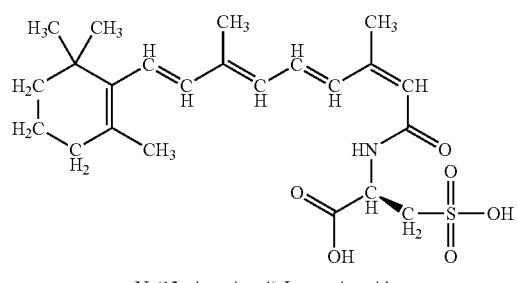

N-(13-cis-retinoyl)-L-cysteic acid (II-1a)

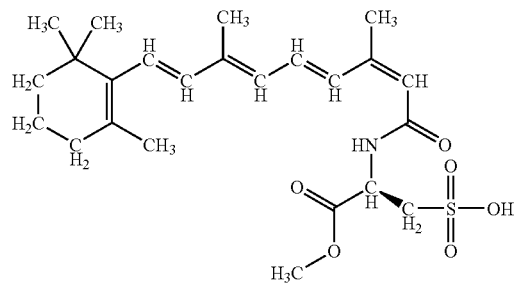

N-(13-cis-retinoyl)-L-cysteic acid methyl ester (II-1b)

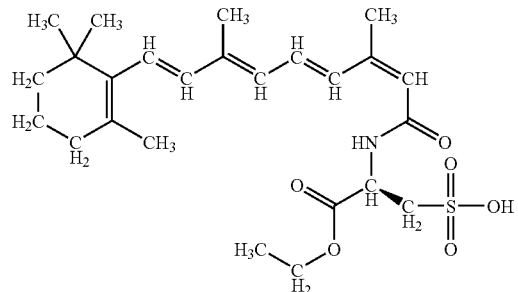

N-(13-cis-retinoyl)-L-cysteic acid ethyl ester (II-1c)

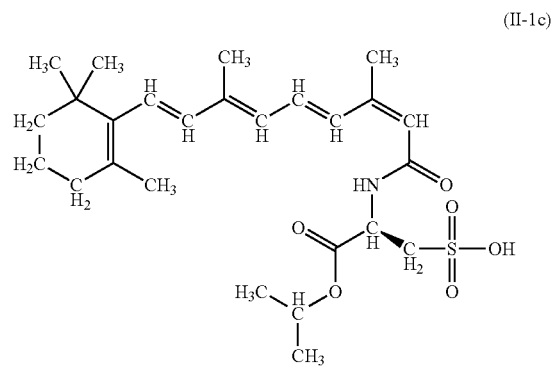

N-(13-cis-retinoyl)-L-cysteic acid isopropyl ester (II-1d)

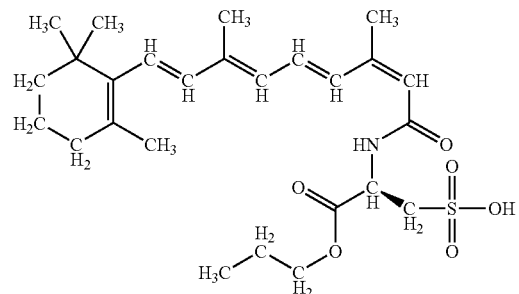

N-(13-cis-retinoyl)-L-cysteic acid propyl ester (II-1e)

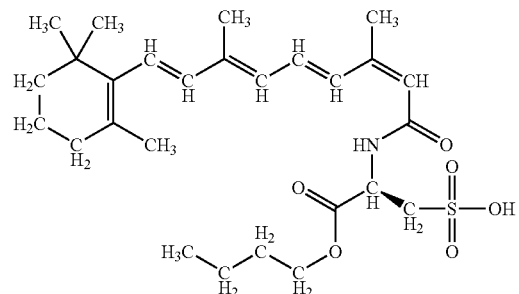

N-(13-cis-retinoyl)-L-cysteic acid butyl ester (II-1f)

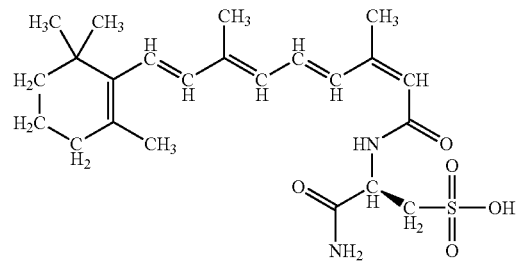

N-(13-cis-retinoyl)-L-cysteic acid amide

The invention also includes sodium salts of these compounds (II-1, II-1a through II-1f) exemplified above, as well as sodium salts of all compounds covered by the general formula.

Further, the invention encompasses the following compound (II-2) and derivatives thereof.

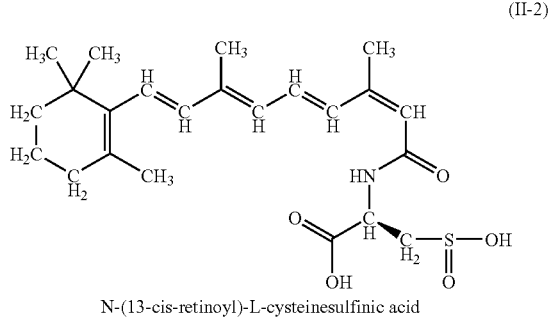

N-(13-cis-retinoyl)-L-cysteinesulfinic acid (II-2)

The invention also includes sodium salt of the above compound (II-2).

The invention also encompasses the following group of compounds (II-3, II-3b) and derivatives thereof:

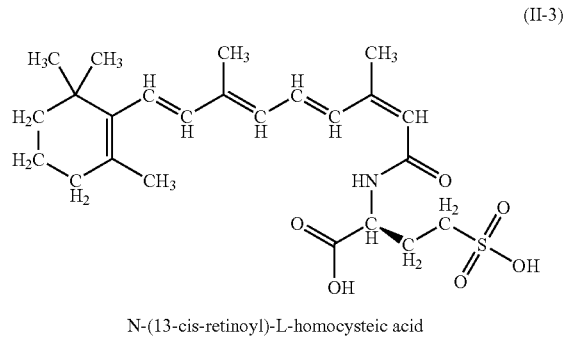

N-(13-cis-retinoyl)-L-homocysteic acid (II-3)

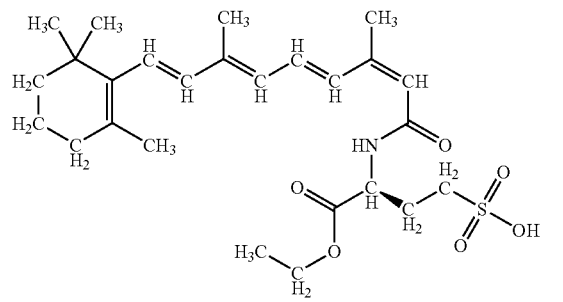

N-(13-cis-retinoyl)-L-homocysteic acid ethyl ester (II-3b)

The invention also includes sodium salts of the above compounds (II-3, II-3b) exemplified above, as well as sodium salts of all compounds covered by the general formula.

The present invention makes available the use of compounds defined by the general formula, in particular the above exemplified compounds, their sodium salts or derivatives thereof for the manufacture of a medicament. The present invention also makes available the use of the compounds defined by the general formula, in particular the above exemplified compounds, their sodium salts or a derivative thereof, for the manufacture of a medicament for treatment of cancer.

Further, the present invention makes available a pharmaceutical composition comprising an active substance in a therapeutically effective amount and one of the compounds defined by the general formula, in particular the above exemplified compounds, their sodium salts or a derivative thereof. In particular, the present invention makes available a pharmaceutical composition wherein the active substance is a cytotoxic compound and the potentiating compound is one of the above compounds, their sodium salts or a derivative thereof According to one embodiment of the invention, said active substances are docetaxel, paclitaxel, doxorubicin and mitoxantrone.

Another embodiment of the present invention is a method for potentiating the efficacy of a pharmaceutically active substance, wherein said substance is prepared in micellar form with at least one of the above compounds, their sodium salts or a derivative thereof.

Another embodiment is a method for increasing the solubility of a pharmaceutically active substance, wherein said substance is prepared in micellar form with at least one of the above compounds, their sodium salts or a derivative thereof.

Yet another embodiment is the method for improving the bio-availability of pharmaceutically active substance, wherein said substance is prepared in micellar form with at least one of the above compounds, their sodium salts or a derivative thereof.

The present invention also makes available a novel pharmaceutical composition, wherein at least one of the above compounds and preferably the corresponding cis- and trans-isomers of one of the above compounds, their sodium salts or a derivative thereof are present in saline, in the presence of calcium ions. Such formulations are disclosed further in the present description and examples, and they have been shown to exhibit surprising properties. Consequently, said invention also makes available a method for the treatment of cancer, wherein at least one of the above compounds or two cis-trans isomers of the above compounds, their sodium salts or derivatives thereof are administered to a patients in aqueous medium of abundant sodium ions containing calcium ions. The amount of calcium is preferably an amount corresponding to a concentration of $CaCl_2$ in the interval of about 2.2 to 2.6 mmol/L (8.8–10.4 mg/dL) or most preferably 2.3 mmol/L.

The present invention also makes available a method for the treatment of cancer, wherein at least one cytotoxic substance is mixed with at least one of the above compounds or two cis-trans isomers of the above compounds, their sodium salts or derivative thereof, and administered to a patient in aqueous medium of abundant sodium ions containing calcium ions. In particular, the invention concerns such methods, wherein the at least one cytotoxic substance is chosen among docetaxel, paclitaxel, doxorubicin and mitoxantrone.

The inventors have shown that the poorly soluble compounds docetaxel and paclitaxel can be dissolved in micelles of N-(all-trans-Retinoyl)-L-cysteic acid (I-1), N-(13-cis-Retinoyl)-L-cysteic acid (II-1), N-(all-trans-Retinoyl)-L-cysteinesulfinic acid (I-2), N-(13-cis-Retinoyl)-L-cysteinesulfinic acid (II-2), N-(all-trans-Retinoyl)-L-homocysteic acid (I-3), N-(13-cis-Retinoyl)-L-homocysteic acid (II-3), sodium salts of their esters (I-1a–I-1e, I-3a; II-1a–II-1e, II-3b) and sodium salts of their amides (I-1f–I-1h, I-3f, II-1f), creating mixed micelles. In this way, an excellent solubility of docetaxel and paclitaxel in the form of mixed micelles in saline is achieved.

Tests evaluating the cytotoxicity of the compounds (I-1a–I-1h, I-3a, I-3f, II-1a–II-1f, II-3b) in the form of sodium salts in the concentration range $10^{-9}$ to $10^{-7}$ M have been performed in cultures of human breast adenocarcinoma cell line MDA-MB-231 and revealed the following dependence: an increase of the concentrations of the inventive compounds led to an enhancement of cell growth inhibition, achieving a value close to 47% for compounds I-1a and II-1a; a value close to 48% for compounds I-1b and II-1b; a value close to 50% for compounds I-1c and I-1c; a value close to 54% for compounds I-1d and II-1d; a value close to 54% for compounds I-1e and II-1e; and a value close to 53% for compounds I-1f and II-1f; a value close to 43% for compound I-1g; a value close to 46% for compound I-1h; a value close to 49% for compound II-3a; a value close to 55% for compound I-3f, a value close to 62% for compound II-3b.

Sodium salts of the compounds I-1 and II-1 were converted into the corresponding acidic forms of the compounds and dissolved in methanol, in order to prepare the formulations docetaxel/compound I-1, docetaxel/compound II-1 and paclitaxel/compound II-1.

The cell growth inhibition of human breast adenocarcinoma cell line MDA-MB-231 achieved by the formulations docetaxel/compound (I-1 and II-1) was close to 86% (close to 48% compared to docetaxel alone as positive control). The concentration of docetaxel in the formulations docetaxel/compound I-1 and docetaxel/compound II-1 required to exhibit the same effect of cell growth inhibition of 50% was more than 5-fold lower, compared to docetaxel alone.

The cell growth inhibition of human ovary adenocarcinoma cell line SKOV-3 by the formulation paclitaxel/compound II-1 has been close to 84% (close to 44% compared to paclitaxel alone as positive control). The concentration of paclitaxel in the formulation paclitaxel/compound II-1 required to exhibit the same effect of cell growth inhibition of 50% was more than 3-fold lower, compared to paclitaxel alone.

In tests evaluating the cytotoxicity of the formulations of docetaxel and sodium salts of compounds (I-1a–I-1c, II-1a–II-1c), the formulation of paclitaxel and sodium salt of compound II-1a displayed the following effects: The cell growth inhibition of human prostate carcinoma cell line DU 145 by the formulations docetaxel/compound (I-1a and II-1a) was close to 88% (close to 53% compared to docetaxel alone as positive control); the cell growth inhibition of human ovary adenocarcinoma cell line SCOV-3 by the formulations docetaxel/compound (I-1b and II-1b) was close to 84% (close to 51% compared to docetaxel); and the cell growth inhibition of human lung carcinoma cell line A549 by the formulations docetaxel/compound (I-1c and II-1c) was close to 88% (close to 40% compared to docetaxel). The concentration of docetaxel in the formulations docetaxel/compound (I-1a–I-1c and II-1a–II-1c) required to exhibit the same effect of cell growth inhibition of 50% was approximately 2–5-fold lower, compared to docetaxel alone.

The cell growth inhibition of human ovary adenocarcinoma cell line SKOV-3 by the formulation paclitaxel/compound II-1a has been close to 82% (close to 39% compared to paclitaxel alone as positive control). The concentration of paclitaxel in the formulation paclitaxel/compound II-1a required to exhibit the same effect of cell growth inhibition of 50% was 2.8-fold lower, compared to paclitaxel alone.

Tests evaluating the cytotoxicity of the formulations of doxorubicin and sodium salts of compounds (I-1d and II-1d) displayed the following effects: The cell growth inhibition of human breast adenocarcinoma cell line MDA-MB-231 by the formulations doxorubicin/compound (I-1d and II-1d) was close to 76% (close to 48% compared to doxorubicin). The concentration of doxorubicin in the formulations doxorubicin/compound I-1d and doxorubicin/compound II-1d required to exhibit the same effect of cell growth inhibition of 50% was approximately 5 to 6-fold lower, compared to doxorubicin alone.

Tests evaluating the cytotoxicity of the formulations of mitoxantrone and sodium salts of compounds (I-1e, I-1f, II-1e and II-1f) displayed the following effects: The cell growth inhibition of human breast adenocarcinoma cell line MDA-MB-231 by the formulations mitoxantone/compound (I-1e and II-1e) was close to 78% (close to 47% compared to mitoxantrone); the cell growth inhibition of human prostate carcinoma cell line DU 145 by the formulations mitoxantrone/compound (I-1f and II-1f) was close to 80% (close to 52% compared to mitoxantrone). The concentration of mitoxantrone in the formulations mitoxantrone/compound (I-1e and II-1e) required to exhibit the same effect of cell growth inhibition of 50% was (12–20)-fold lower, compared to mitoxantrone alone. The concentration of mitoxantrone in the formulations mitoxantrone/compound (I-1f and II-1f) required to exhibit the same effect of cell growth inhibition of 50% was 4 to 6-fold lower, compared to mitoxantrone alone.

The inventive formulations of N-(all-trans-Retinoyl)-L-cysteic acid (I-1), N-(13-cis-Retinoyl)-L-cysteic acid (II-1), N-(all-trans-Retinoyl)-L-cysteinesulfinic acid (I-2), N-(13-cis-Retinoyl)-L-cysteinesulfinic acid (II-2), N-(all-trans-Retinoyl)-L-homocysteic acid (I-3), N-(13-cis-Retinoyl)-L-homocysteic acid (II-3), sodium salts of these compounds, sodium salts of their esters (I-1a–I-1e, I-3a; II-1a–II-1e, II-3b), sodium salts of their amides (I-1f–I-1h, I-3f, II-1f) and docetaxel or paclitaxel were prepared as follows.

Solutions of docetaxel or paclitaxel and any one of the inventive compounds (I-1–I-3, II-1–II-3 or sodium salts of these compounds; I-1a–I-1e, I-3a; II-1a–II-1e, II-3b; I-1f–I-1h, I-3f, II-1f) in ethanol (or other aliphatic alcohol) were first prepared in appropriate concentrations. Then aliquots of these solutions were mixed to form mixed micellar solutions with the desired molar ratio of docetaxel/compound (I-1–I-3, II-1–II-3 or sodium salts of these compounds; I-1a–I-1e, I-3a; II-1a–II-1e, II-3b; I-1f–I-1h, I-3f, II-1f) or paclitaxel/compound (I-1–I-3, II-1–II-3 or sodium salts of these compounds; I-1a–I-1e, I-3a; II-1a–II-1e, II-3b; I-1f–I-1h, I-3f, II-1f). After stirring, the organic solvent was evaporated in a rotary evaporator under reduced pressure. The resulting dry film was then dissolved in water. The obtained solution was filtered through a 22 μm sterile filter and lyophilized to obtain the formulations in dry form.

The formulations of docetaxel/compound and paclitaxel/compound in mixed-micellar systems in dry form were shown to be stable for a sufficient period of time awaiting usage. There was no change in the concentration of the active ingredients during 6-months storage at 4° C. The formulations docetaxel/compound (I-1–I-3, II-1–II-3 or sodium salts of these compounds; I-1a–I-1e, I-3a; II-1a–II-1e, II-3b; I-1f–I-1h, I-3f, II-1f) and paclitaxel/compound (I-1–I-3, II-1–II-3 or sodium salts of these compounds; I-1a–I-1e, I-3a; II-1a–II-1e, II-3b; I-1f–I-1h, I-3f, II-1f) were reconstituted with water or saline and exhibited unchanged cytotoxic action in MDA-MB-231 cell line after 6-months storage at 4° C.

The formulations of doxorubicin/compound or mitoxantrone/compound were prepared as follows:

An aliquot of stock water-alcohol solution of N-(all-trans-Retinoyl)-L-cysteic acid (I-1), N-(13-cis-Retinoyl)-L-cysteic acid (II-1), N-(all-trans-Retinoyl)-L-cysteinesulfinic acid (I-2), N-(13-cis-Retinoyl)-L-cysteinesulfinic acid (II-2), N-(all-trans-Retinoyl)-L-homocysteic acid (I-3), N-(13-cis-Retinoyl)-L-homocysteic acid (II-3), sodium salts of these compounds, sodium salts of their esters (I-1a–I-1e, I-3a; II-1a–II-1e, II-3b), sodium salts of their amides (I-1f–I-1h, I-3f, II-1f) was evaporated in a rotary evaporator under reduced pressure. The resulting dried film was dissolved in water. The obtained solution was mixed with an aliquot of solution of doxorubicin in water or with an aliquot of solution of mitoxantrone in water to form a mixed micellar solution with the desired molar ratio of doxorubicin/compound (I-1–I-3, II-1–II-3 or sodium salts of these compounds; I-1a–I-1e, I-3a; II-1a–I-1e, II-3b; I-1f–I-1h, I-3f, II-1f) or mitoxantrone/compound (I-1–I-3, II-1–II-3 or sodium salts of these compounds; I-1a–I-1e, I-3a; II-1a–II-1e, II-3b; I-1f–I-1h, I-3f, II-1f). Each solution was filtered through a 22 µm sterile filter and lyophilized to obtain the formulations in dry form.

The formulations of doxorubicin/compound and mitoxantrone/compound in mixed-micellar systems in dry form were shown to be stable for a sufficient period of time awaiting usage. There was no change in the concentration of the active ingredients during 6-months storage at 4° C. The formulations of doxorubicin/compound (I-1–I-3, II-1–II-3 or sodium salts of these compounds; I-1a–I-1e, I-3a; II-1a–II-1e, II-3b; I-1f–I-1h, I-3f, II-1f) and mitoxantrone/compound (I-1–I-3, II-1–II-3 or sodium salts of these compounds; I-1a–I-1e, I-3a; II-1a–II-1e, II-3b; I-1f–I-1h, I-3f, II-1f) were reconstituted with water and exhibited unchanged cytotoxic action in MDA-MB-231 cell line after 6-months storage at 4° C.

A comparative evaluation of the cytotoxicity of the inventive compounds was carried out using consecutive dilutions of their initial solutions before adding to cell cultures. The influence of calcium ions on the cytotoxicity of the compounds themselves and the formulations was exemplified by performing a series of consecutive dilutions of their initial solutions in saline with 2.3 mM $CaCl_2$ (A), normal saline (B) and culture media with 5% FBS (C).

The concentration of 2.3 mM $CaCl_2$ was chosen as it is widely known that total calcium in human serum is maintained between 2.2 and 2.6 mmol/L (8.8–10.4 mg/dL).

The comparative tests evaluating the cytotoxicity of the compounds (I-1, I-1f–I-1h, I-3f; II-1, II-1a, II-1f, II-3b) in the form of sodium salts in the concentration range $10^{-9}$ to $10^{-7}$ M related to dilution of their initial solutions in (A) and (B) have been performed in cultures of human breast adenocarcinoma cell line MDA-MB-231 and displayed the following results: an increase of the concentrations of the inventive compounds, led to a enhancement of cell growth inhibition, achieving a value close to 31% for compound I-1 in (B) and a value close to 41.5% for compound I-1 in (A) (close to 15% compared to compound I-1 in B); a value close to 45% for compound I-1f in (B) and a value close to 53% for compound I-1f in (A) (close to 15% compared to compound I-1f in B); a value close to 23% for compound I-1g in (B) and a value close to 43% for compound I-1g in (A) (close to 26.5% compared to compound I-1g in B); a value close to 26% for compound I-1h in (B) and a value close to 42% for compound I-1h in (A) (close to 21% compared to compound I-1h in B); a value close to 41% for compound I-3f in (B) and a value close to 54% for compound I-3f in (A) (close to 22% compared to compound I-3f in B); a value close to 32% for compound II-1 in (B) and a value close to 43% for compound II-1 in (A) (close to 15.5% compared to compound II-1 in B); a value close to 40.5% for compound II-1a in (B) and a value close to 49% for compound II-1a in (A) (close to 14% compared to compound II-1a in B); a value close to 46% for compound II-1f in (B) and a value close to 54% for compound II-1f in (A) (close to 15% compared to compound II-1f in B); a value close to 44% for compound II-3b in (B) and a value close to 60.5% for compound II-3b in (A) (close to 29% compared to compound II-3b in B).

The comparative tests evaluating the cytotoxicity of the compound II-1a in the form of sodium salt in the concentration range $10^{-9}$ to $10^{-7}$ M related to dilution its initial solution in (A) and (B) have been performed in cultures of human lung carcinoma cell line A549 and displayed the following effects: an increase of the concentration of the inventive compound led to a enhancement of cell growth inhibition, achieving a value close to 26% for compound II-1a in (B) and a value close to 34% for compound II-1a in (A) (close to 12% compared to compound II-1a in B).

The comparative tests evaluating the cytotoxicity of the formulation of docetaxel/compounds (I-1a+II-1a), paclitaxel/compound I-1, paclitaxel/compounds (I-1a+II-1a), doxorubicin/compounds (I-1a+II-1a), doxorubicin/compound I-1f in the concentration range $10^{-9}$ to $10^{-7}$ M related to dilution of their initial solutions in (A) and (B) and (C) have been performed in cultures of human breast adenocarcinoma cell line MDA-MB-231 and displayed the following results: The cell growth inhibition by the formulation docetaxel/compounds (I-1a+II-1a) in a concentration of of docetaxel of $10^{-7}$ M was close to 86% in (A) (close to 41% compared to docetaxel alone), was close to 81% in (B) (close to 18% compared to docetaxel alone), was close to 86.5% in (C) (close to 43% compared to docetaxel alone); by the formulation paclitaxel/compound I-1 in a concentration of of paclitaxel of $10^{-7}$ M was close to 83% in (A) (close to 39% compared to paclitaxel alone), was close to 79% in (B) (close to 26% compared to paclitaxel alone), was close to 84% in (C) (close to 42% compared to paclitaxel alone); by the formulation paclitaxel/compounds (I-1a+II-1a) in a concentration of of paclitaxel of $10^{-7}$ M was close to 84% in (A) (close to 45% compared to paclitaxel alone), was close to 79% in (B) (close to 25% compared to paclitaxel alone), was close to 85% in (C) (close to 48% compared to paclitaxel alone); by the formulation doxorubicin/compounds (I-1a+II-1a) in a concentration of of doxorubicin of $10^{-7}$ M was close to 77% in (A) (close to 48% compared to doxorubicin alone), was close to 66% in (B) (close to 25% compared to doxorubicin alone), was close to 78% in (C) (close to 51% compared to doxorubicin alone); by the formulation doxorubicin/compound I-1f in a concentration of of doxorubicin of $10^{-7}$ M was close to 81% in (A) (close to 58% compared to doxorubicin alone), was close to 70% in (B) (close to 33% compared to doxorubicin alone), was close to 82% in (C) (close to 60% compared to doxorubicin alone).

The concentrations of docetaxel in the formulation docetaxel/compounds (I-1a+II-1a) in (A), in the formulation in (B), in the formulation in (C) required to exhibit the same effect of cell growth inhibition of 50% were approximately 5.7-fold lower, 3.3-fold lower, 7.7-fold lower, respectively, compared to docetaxel alone.

The concentrations of paclitaxel in the formulation paclitaxel/compound I-1 in (A), in the formulation in (B), in the formulation in (C) required to exhibit the same effect of cell growth inhibition of 50% were approximately 11.3-fold lower, 2.8-fold lower, 14.1-fold lower, respectively, compared to paclitaxel alone.

The concentrations of paclitaxel in the formulation paclitaxel/compounds (I-1a+II-1a) in (A), in the formulation in (B), in the formulation in (C) required to exhibit the same effect of cell growth inhibition of 50% were approximately 7.7-fold lower, 2.1-fold lower, 10.0-fold lower, respectively, compared to paclitaxel alone.

The concentrations of doxorubicin in the formulation doxorubicin/compounds (I-1a+II-1a) in (A), in the formulation in (B), in the formulation in (C) required to exhibit the same effect of cell growth inhibition of 50% were approximately 18.2-fold lower, 2.8-fold lower, 34.4-fold lower, respectively, compared to doxorubicin alone.

The concentrations of doxorubicin in the formulation doxorubicin/compound I-1f in (A), in the formulation in (B), in the formulation in (C) required to exhibit the same effect of cell growth inhibition of 50% were approximately 17.3-fold lower, 3.0-fold lower, 30.5-fold lower, respectively, compared to doxorubicin alone.

The comparative tests evaluating the cytotoxicity of the formulation of docetaxel/compounds (I-1a+II-1a) in the concentration range $10^{-9}$ to $10^{-7}$ M related to dilution its initial solution in (A) and (B) and (C) have been performed in cultures of human lung carcinoma cell line A549 and displayed the following effects: The cell growth inhibition by the formulation in a concentration of of docetaxel of $10^{-7}$ M was close to 88% in (A) (close to 40% compared to docetaxel alone), was close to 85% in (B) (close to 23% compared to docetaxel alone), was close to 88% in (C) (close to 41% compared to docetaxel alone).

The concentrations of docetaxel in the formulation docetaxel/compounds (I-1a+II-1a) in (A), in the formulation in (B), in the formulation in (C) required to exhibit the same effect of cell growth inhibition of 50% were approximately 2.2-fold lower, 1.5-fold lower, 2.2-fold lower, respectively, compared to docetaxel alone.

The comparative evaluation of cytotoxicity of the inventive compounds themselves and the formulation related to dilutions of their initial solutions in normal saline and saline with 2.3 mM $CaCl_2$ exhibited a surprising effect associate with the last vehicle. In the last case the means of cell growth inhibition were close to the results of activity of the compounds and the formulations after dilution their solutions by culture media. In this connection, it is necessary to emphasize that all culture media used in the examples disclosed herein contained $Ca^{2+}$ ions. The experimental results revealed an important role of $Ca^{2+}$ ions for the therapeutic activity, and in particular the antitumour activity of the inventive compounds. An aqueous medium having an abundance of sodium ions, but containing a small amount of calcium ions creates the most favourable conditions for the cytotoxic action of the inventive compounds.

The structures of the inventive compounds favour $Ca^{2+}$ binding. The sodium salts of compounds I-1, I-2, I-3 and II-1, II-2, II-3 contain sulfonate or sulfinate and carboxylate groups, existing primarily in conjugate base forms neutralized $Na^+$ ions in aqueous medium at about physiological pH. The sodium salts of compounds I-1f through I-1h, II-1f, I-3f contain sulfonate group neutralized $Na^+$ ion and carboxamide groups. The sodium salts of compounds I-1a through I-1e, II-1a through II-1e, I-3a and II-3b contain sulfonate group neutralized $Na^+$ ion and ester groups. In a medium having an abundance of sodium ions, a small amount of calcium ions can form calcium-helate complexes, comprising at least one and/or two molecules of the compounds according to the invention and the bound metal atom. Chelation refers to coordination of two or more donor's atoms from a ligand to a central metal atom. The resulting complex has stability derived in part from the favourable entropic factor accompanying the release molecules of water from the coordination sphere.

In order to be active in the central nervous system, the inventive compounds in the form of labile calcium-helate complexes will require the inclusion—in coordination with one metal atom—of the cis-trans isomers of each ligand, namely, all-trans-retinoyl-L-cysteic acid and 13-cis-retinoyl-L-cysteic acid; all-trans-retinoyl-L-cysteic acid methyl ester and 13-cis-retinoyl-L-cysteic acid methyl ester; all-trans-retinoyl-L-cysteic acid amide and 13-cis-retinoyl-L-cysteic acid amide and so forth. It is widely known that $Ca^{2+}$ ion favors high coordination numbers and irregular coordination geometry.

The inventive compounds in themselves have low toxicity. A single dose i.p. toxicity study in rats was carried out. The compounds (I-1, I-2, II-3, I-1a, II-1a, I-1f, I-1h, II-1f, I-3a, I-3f, II-3b) at the dose level of 100 mg/kg body weight did not produce mortality. The minimal lethal dose is thus above 100 mg/kg body weight for these compounds.

The compounds according to the invention can be used as such or as component in pharmaceutical compositions. The compounds can be given systemically or locally, for example topically. Suitable modes of administration of the compounds themselves and in pharmaceutical compositions include intravenous administration, intraperitoneal administration. The oral, rectal and transdermal administration of the compounds can be suitable and effective. The compounds can exhibit high activity in the central nervous system and oral, rectal and transdermal administration will require a low dose of the compound to receive a high response rate. To obtain optimal results in the treatment of patients the compounds themselves, and in the form of pharmaceutical preparations, need to be dissolved in an aqueous medium having an abundance of sodium ions and containing a small amount of calcium ions.

EXAMPLES

Materials and Methods all-trans-Retinoic, 13-cis-Retinoic and L-cysteic, L-cysteinesulfinic, L-homocysteic acids were purchased from Sigma Chemical Co., St. Louis, Mo., USA. All other chemical reagents and solvents were purchased from Aldrich Chemical Co.

$^1$H-NMR spectra were recorded at 400 MHz using a Varian Unity-400 spectrometer. DMSO-$d_6$ was used as a solvent.

Merck silica gel 60 pre-coated plates were used for thin-layer chromatography (TLC) and developed in a solvent system consisting of chloroform-methanol (4:1, v/v). Detection of the compounds on TLC plates was achieved by spraying with 10% $H_2SO_4$ in methanol followed by heating to 150° C., staining by iodine, and detection in UV-light (λ366 nm).

The determination of the concentrations of the compounds synthesized was performed by UV-spectra (Shimadzu UV-mini-1240 spectrophotometer, λ÷250–500 nm, EtOH) for the derivatives of all-trans-retinoic acid: $\lambda_{max}$ 348–350 nm, ε 45000; for the derivatives of 13-cis-retinoic acid: $\lambda_{max}$ 348–350 nm, ε 37000. The concentrations determined by UV-spectra were equal to the weights of the samples.

The compounds synthesized are soluble in chloroform, ethanol, methanol, and 70% aq ethanol. All steps of the synthesis were performed in dry nitrogen atmosphere.

The cells of four human tumor cell lines were purchased from the American Type Culture Collection (Rockville, Md., USA): Human Breast Adenocarcinoma Cell Line MDA-MB-231 (ATCC-HTB-26, Lot 1227150), Human Prostate Carcinoma Cell Line DU 145 (ATCC-HTB-81, Lot 1391494), Human Ovary Adenocarcinoma Cell Line SKOV-3 (ATCC-HTB-77, Lot 1658010) and Human Lung Carcinoma Cell Line A549 (ATCC-CCL-185, Lot 1388888).

MDA-MB-231 cells were propagated in MEM culture medium with 2 mM L-glutamine, 10% heat-inactivated fetal bovine serum (FBS) and antibiotics. DU 145 cells were cultured in MEM culture medium containing 2 mM L-glutamine, 1 mM sodium pyruvate, 10% FBS and antibiotics. SKOV-3 cells were cultured in McCoy's 5A culture medium, supplemented with 1,5 mM L-glutamine, 10% FBS and antibiotics. A549 cells were cultured in Ham's F-12 culture medium with 1 mM L-glutamine, 10% FBS and antibiotics. All media and supplements were purchased from Sigma-Aldrich (St. Louis, Mo., USA). Cell propagation of all lines was carried out in Falcon™ 25 cm$^2$ cultivation flasks (Becton Dickinson Labware).

Drug cytotoxicity testing was carried out with using Falcon™ 96-well cultivation plates for adherent cells (Becton Dickinson Labware). These plates were seeded by cells either at 12×10$^3$ MDA-MB-231 cells/well, or at 12×10$^3$ DU 145 cells/well, or at 14×10$^3$ SKOV-3 cells/well, or at 10×10$^3$ A549 cells/well in a volume of 200 μL/well.

Both flasks and cultivation plates were incubated for cell growth at 37° C. in a humidified atmosphere of 95% air and 5% $CO_2$.

The cell cultures in cultivation plates were allowed to adhere for 24 hour of incubation. On day 1 after cell seeding, 2 μL solutions of the drugs to be tested in medium with 5% FBS was added to the cultures. In the control cultures, 2 μL of medium with 5% FBS was added as solvent control. The cells were incubated for 2 consecutive days. At the end of the incubation period adherent cells were detached by trypsinization and the number of viable cells was counted using trypan blue exclusion test and a hemocytometer. All data were derived from an average of three determinations each in six replicates. The results were expressed as mean cell number±SE and the differences between control and test series evaluated by means of Student's t-test. The drug cytotoxicity was evaluated based on the extent of cell growth inhibition. The cell growth inhibition of the tested drugs was calculated as follows:

$$\text{Cell growth inhibition \%} = \frac{\text{Control} - \text{TestSeries}}{\text{Control}} \times 100$$

In the case of comparative evaluation of cytotoxicity of the inventive compounds themselves and the formulation related to consecutive dilutions of their initial solutions before adding to the cultures, 2 μL solutions of the drugs to be tested in medium with 5% FBS, in normal saline and in saline with 2,3 mM $CaCl_2$ were added to the cultures. In control cultures, 2 μL of medium with 5% FBS, normal saline and saline with 2,3 mM $CaCl_2$ were added as solvent controls (negative controls). The differences between these control series were insignificant. Therefore an average of negative controls was calculated. In other control cultures, 2 μL solutions of docetaxel, paclitaxel, doxorubicin in medium with 5% FBS, in normal saline and in saline with 2,3 mM $CaCl_2$ were added to the cultures (positive controls). The differences between these control series for each antibiotic were insignificant. Therefore an average of positive controls was calculated (for each antibiotic).

Example 1

Synthesis of N-retinoyl-L-cysteic acids esters and amides and N-retinoyl-L-homocysteic acids esters and amides Synthesis of esters of L-cysteic and L-homocysteic acids. Thionyl chloride (3 mmol, 0.219 ml) was added to the 50 ml of an appropriate alcohol while stirring followed by L-cysteic acid monohydrate (1 mmol, 187 mg) or L-homocysteic acid (1 mmol, 183 mg) after 15 min, whereupon the mixture was refluxed for 48 hrs. The alcohol was evaporated under reduced pressure and the residue recrystallized from ethanol. Yields in the interval of 85–95% were achieved for all esters.

Synthesis of amides of L-cysteic and L-homocysteic acids. 10 ml of aqueous solution of an appropriate amine (28% solution of $NH_3$ or 40% solution of methylamine or dimethylamine in water) was added to a solution of a methyl ester of the appropriate acid (1 mmol) in 5 ml of water and the resulted solution was allowed to stay for 2–7 days. The solvent and an excess of the amine were removed under reduced pressure and the residue was recrystallized from methanol. Yields in the interval of 30–85% were achieved for all amides.

Acylation of L-cysteic acid esters and amides and L-homocysteic acids esters and amides. all-trans- or 13-cis-retinoic acid (150 mg, 0.5 mmol) and triethylamine (0.083 ml, 0.6 mmol) were dissolved in 1 ml of anhydrous tetrahydrofuran, whereupon anhydrous acetonitrile (2 ml) was added, the mixture chilled to −20° C., and 0.07 ml (0.55 mmol) of butyl chloroformate added. After 30 min, the mixture, free of the precipitated triethylamine hydrochloride, was pipetted in a solution of an appropriate derivative of L-cysteic or L-homocysteic acids (0.75 mmol) in a mixture of 3 ml of saturated solution of $NaHCO_3$ (appr. 1.1 M), 10 ml of $H_2O$, 8 ml of methanol and 15 ml of THF. After stirring for 10 hours at room temperature, the mixture was partly evaporated under reduced pressure until the unreacted retinoic acid began to fall out (to a residual volume of about 10 ml). Then, 15 ml of $H_2O$ was added to the residue and the unreacted retinoic acid was extracted with ether (5×30 ml). 20 ml of saturated NaCl solution was added to the aqueous solution and the product extracted by ethyl acetate (3×30 ml). The solvent was evaporated under reduced pressure. The residue obtained was dissolved in 20 ml of ethanol and all insoluble impurities filtered off. The product was stored in the form of a clear solution of the pure product obtained.

In order to obtain the acidic form of the compound, a solution of its sodium salt was evaporated under reduced pressure, dissolved in water, carefully acidified with 0.1 M HCl to pH 3.5 and extracted with chloroform-ethanol (1:1, v/v). Chloroform was evaporated under reduced pressure to give the concentrated ethanol-water solution, which, when necessary, was diluted with ethanol and filtered. Then the solution of the compound obtained was immediately used.

Compound (I-1a):

Yield: 65%. $R_f$ 0.30–0.35. $^1$H-NMR ($CD_3SOCD_3$, 400 MHz) δ 1.00 [6H, s, C($CH_3$)$_2$], 1.43 and 1.56 [2H+2H, 2 m, $CH_2CH_2$C($CH_3$)$_2$], 1.68 [3H, s, $CH_3$C=CC($CH_3$)$_2$], 1.95 [3H, s, $CH_3$C=(CH)$_3$C($CH_3$)=CHCO], 1.99 (2H, m, C$H_2$C=), 2.24 (3H, s, $CH_3$C=CHCO), 2.81 (2H, d, J 6.0 Hz, SC$H_2$), 3.57 (3H, s, OC$H_3$), 4.47 (1H, m, NC$H$), 5.83 (1H, s, =C$H$CO), 6.12–6.26 [3H, m, C$H$=C$H$C($CH_3$)=C$H$CH=CH], 6.34 [1H, d, J 15.0 Hz, C$H$C($CH_3$)=CHCO], 6.92 [1H, dd, J 15.0, 11.5 Hz, C$H$=CHC($CH_3$)=CHCO], 8.16 (1H, d, J 6.4 Hz, N$H$).

Compound (I-1b):

Yield: 55%. R_f 0.35–0.40. ¹H-NMR (CD₃SOCD₃, 400 MHz) δ 1.00 [6H, s, C(CH₃)₂], 1.16 (3H, t, J 7.1 Hz, CH₃CH₂), 1.42 and 1.56 [2H+2H, 2 m, CH₂CH₂C(CH₃)₂], 1.67 [3H, s, CH₃C=CC(CH₃)₂], 1.95 [3H, s, CH₃C=(CH)₃C(CH₃)=CHCO], 1.99 (2H, m, CH₂C=), 2.24 (3H, s, CH₃C=CHCO), 2.81 (2H, d, J 6.1 Hz, SCH₂), 4.04 (2H, q, J 7.1 Hz, OCH₂), 4.44 (1H, m, NCH), 5.84 (1H, s, =CHCO), 6.11–6.26 [3H, m, CH=CHC(CH₃)=CHCH=CH], 6.34 [1H, d, J 15.0 Hz, CHC(CH₃)=CHCO], 6.91 [1H, dd, J 15.0, 11.5 Hz, CH=CHC(CH₃)=CHCO], 8.14 (1H, d, J 6.4 Hz, NH).

Compound (I-1c):

Yield: 57%. R_f 0.35–0.40. ¹H-NMR (CD₃SOCD₃, 400 MHz) δ 1.00 [6H, s, C(CH₃)₂], 1.14 and 1.17 [3H+3H, 2 d, J 6.2 Hz, (CH₃)₂CHO], 1.43 and 1.55 [2H+2H, 2 m, CH₂CH₂C(CH₃)₂], 1.68 [3H, s, CH₃C=CC(CH₃)₂], 1.95 [3H, s, CH₃C=(CH)₃C(CH₃)=CHCO], 1.99 (2H, m, CH₂C=), 2.24 (3H, s, CH₃C=CHCO), 2.79 (2H, d, J 6.0 Hz, SCH₂), 4.38 (1H, m, NCH), 4.84 (1H, m, OCH), 5.84 (1H, s, =CHCO), 6.11–6.26 [3H, m, CH=CHC(CH₃)=CHCH=CH], 6.34 [1H, d, J 15.0 Hz, CHC(CH₃)=CHCO], 6.91 [1H, dd, J 15.0, 11.5 Hz, CH=CHC(CH₃)=CHCO], 8.12 (1H, d, J 6.2 Hz, NH).

Compound (I-1d):

Yield: 58%. R_f 0.40–0.45. ¹H-NMR (CD₃SOCD₃, 400 MHz) δ 0.86 (3H, t, J 7.3 Hz, CH₃CH₂), 1.00 [6H, s, C(CH₃)₂], 1.43 and 1.55 [2H+2H, 2m, CH₂CH2C(CH₃)₂], 1.55 (2H, m, CH₂CH₃), 1.67 [3H, s, CH₃C=CC(CH₃)₂], 1.95 [3H, s, CH₃C=(CH)₃C(CH₃)=CHCO], 1.99 (2H, m, CH₂C=), 2.24 (3H, s, CH₃C=CHCO), 2.81 (2H, d, J6.0 Hz, SCH₂), 3.95 (2H, m, OCH₂), 4.44 (1H, m, NCH), 5.84 (1H, s, =CHCO), 6.12–6.26 [3H, m, CH=CHC(CH₃)=CHCH=CH], 6.34 [1H, d, J 15.2 Hz, CHC(CH₃)=CHCO], 6.91 [1H, dd, J 15.2, 11.3 Hz, CH=CHC(CH₃)=CHCO], 8.15 (1H, d, J 6.4 Hz, NH).

Compound (I-1e):

Yield: 60%. R_f 0.40–0.45. ¹H-NMR (CD₃SOCD₃, 400 MHz) δ 0.86 (3H, t, J 7.3 Hz, CH₃CH₂), 1.00 [6H, s, C(CH₃)₂], 1.31 (2H, m, CH₂CH₃), 1.43 and 1.55 [2H+2H, 2 m, CH₂CH₂C(CH₃)₂], 1.52 (2H, m, CH₂CH₂O), 1.68 [3H, s, CH₃C=CC(CH₃)₂], 1.95 [3H, s, CH₃C=(CH)₃C(CH₃)=CHCO], 1.99 (2H, m, CH₂C=), 2.24 (3H, s, CH₃C=CHCO), 2.81 (2H, d, J 6.0 Hz, SCH₂), 3.99 (2H, m, OCH₂), 4.43 (1H, m, NCH), 5.84 (1H, s, =CHCO), 6.11–6.26 [3H, m, CH=CHC(CH₃)=CHCH=CH], 6.34 [1H, d, J 15.0 Hz, CHC(CH₃)=CHCO], 6.91 [1H, dd, J 15.0, 11.5 Hz, CH=CHC(CH₃)=CHCO], 8.15 (1H, d, J6.4 Hz, NH).

Compound (I-1f):

Yield: 32%. R_f 0.10–0.15. ¹H-NMR (CD₃SOCD₃, 400 MHz) δ 1.00 [6H, s, C(CH₃)₂], 1.42 and 1.55 [2H+2H, 2 m, CH₂CH₂C(CH₃)₂], 1.67 [3H, s, CH₃C=CC(CH₃)₂], 1.95 [3H, s, CH₃C=(CH)₃C(CH₃)=CHCO], 1.99 (2H, m, CH₂C=), 2.25 (3H, s, CH₃C=CHCO), 2.73 (1H, dd, J 13.9, 7.7 Hz, SCH$^a$H$^b$), 2.83 (1H, dd, J 13.9, 4.8 Hz, SCH$^a$H$^b$), 4.36 (1H, m, NCH), 5.83 (1H, s, =CHCO), 6.11–6.27 [3H, m, CH=CHC(CH₃)=CHCH=CH], 6.33 [1H, d, J 15.2 Hz, CHC(CH₃)=CHCO], 6.90 [1H, dd, J 15.2, 11.5 Hz, CH=CHC(CH₃)=CHCO], 6.93 (1H, br s, NH$^a$H$^b$), 7.34 (1H, br s, NH$^a$H$^b$), 8.02 (1H, d, J6.4 Hz, NHCH).

Compound (I-1g):

Yield: 30%. R_f 0.20–0.25. ¹H-NMR (CD₃SOCD₃, 400 MHz) δ 0.99 [6H, s, C(CH₃)₂], 1.42 and 1.56 [2H+2H, 2 m, CH₂CH₂C(CH₃)₂], 1.67 [3H, s, CH₃C=CC(CH₃)₂], 1.94 [3H, s, CH₃C=(CH)₃C(CH₃)=CHCO], 1.99 (2H, m, CH₂C=), 2.27 (3H, s, CH₃C=CHCO), 2.53 (3H, d, J 4.6 Hz, CH₃NH), 2.73 (1H, dd, J 13.7, 7.9 Hz, SCH$^a$H$^b$), 2.83 (1H, dd, J 13.7, 4.8 Hz, SCH$^a$H$^b$), 4.40 (1H, m, NCH), 5.84 (1H, s, =CHCO), 6.10–6.27 [3H, m, CH=CHC(CH₃)=CHCH=CH], 6.32 [1H, d, J 15.0 Hz, CHC(CH₃)=CHCO], 6.90 [1H, dd, J 15.0, 11.4 Hz, CH=CHC(CH₃)=CHCO], 7.77 (1H, m, NHCH₃), 8.04 (1H, d, J 6.4 Hz, NHCH).

Compound (I-1h):

Yield: 21%. R_f 0.20–0.25. ¹H-NMR (CD₃SOCD₃, 400 MHz) δ 1.00 [6H, s, C(CH₃)₂], 1.42 and 1.56 [2H+2H, 2 m, CH₂CH₂C(CH₃)₂], 1.67 [3H, s, CH₃C=CC(CH₃)₂], 1.94 [3H, s, CH₃C=(CH)₃C(CH₃)=CHCO], 1.99 (2H, m, CH₂C=), 2.25 (3H, s, CH₃C=CHCO), 2.59 (1H, dd, J 13.5, 6.4 Hz, SCH$^a$H$^b$), 2.77 [3H, s, (CH₃)$^a$N(CH₃)$^b$], 2.82 (1H, dd, J 13.5, 6.2 Hz, SCH$^a$H$^b$), 3.11 [3H, s, (CH₃)$^a$N(CH₃)$^b$], 5.00 (1H, m, NCH), 5.84 (1H, s, =CHCO), 6.10–6.32 [4H, m, CH=CHC(CH₃)=CHCH=CH], 6.89 [1H, dd, J 15.2, 11.5 Hz, CH=CHC(CH₃)=CHCO], 8.13 (1H, d,J 7.1 Hz, NH).

Compound (I-3a):

Yield: 58%. R_f 0.30–0.35. ¹H-NMR (CD₃SOCD₃, 400 MHz) δ 1.00 [6H, s, C(CH₃)₂], 1.42 and 1.55 [2H+2H, 2 m, CH₂CH₂C(CH₃)₂], 1.67 [3H, s, CH₃C=CC(CH₃)₂], 1.86–2.07 (2H, br m, CH₂CH₂S), 1.95 [3H, s, CH₃C=(CH)₃C(CH₃)=CHCO], 1.99 (2H, m, CH₂C=), 2.25 (3H, s, CH₃C=CHCO), 2.47 (2H, m, SCH₂), 3.61 (3H, s, OCH₃), 4.31 (1H, m, NCH), 5.90 (1H, s, =CHCO), 6.11–6.29 [3H, m, CH=CHC(CH₃)=CHCH=CH], 6.29 [1H, d, J 15.0 Hz, CHC(CH₃)=CHCO], 6.91 [1H, dd, J 15.0, 11.5 Hz, CH=CHC(CH₃)=CHCO], 8.46 (1H, d, J 6.9 Hz, NH).

Compound (I-3f):

Yield: 35%. R_f 0.10–0.15. ¹H-NMR (CD₃SOCD₃, 400 MHz) δ 1.00 [6H, s, C(CH₃)₂], 1.42 and 1.55 [2H+2H, 2 m, CH₂CH₂C(CH₃)₂], 1.67 [3H, s, CH₃C=CC(CH₃)₂], 1.80–2.00 (2H, br m, CH₂CH₂S), 1.94 [3H, S, CH₃C=(CH)₃C(CH₃)=CHCO], 1.98 (2H, m, CH₂C=), 2.26 (3H, s, CH₃C=CHCO), 2.45 (2H, m, SCH₂), 4.26 (1H, m, NCH), 5.96 (1H, s, =CHCO), 6.10–6.31 [4H, m, CH=CHC(CH₃)=CHCH=CH], 6.89 [1H, dd, J 15.0, 11.3 Hz, CH=CHC(CH₃)=CHCO], 7.00 (1H, br s, NH$^a$H$^b$), 7.41 (1H, br s, NH$^a$H$^b$), 8.12 (1H, d, J 8.1 Hz, NHCH).

Compound (II-1a):

Yield: 63%. R_f 0.25–0.30. ¹H-NMR (CD₃SOCD₃, 400 MHz) δ 1.00 [6H, s, C(CH₃)₂], 1.42 and 1.56 [2H+2H, 2 m, CH₂CH₂C(CH₃)₂], 1.67 [3H, s, CH₃C=CC(CH₃)₂], 1.95 and 198 (3H+3H, 2 s, CH₃C=(CH)₃C(CH₃)=CHCO], 1.99 (2H, m, CH₂C=), 2.82 (2H, d, J6.0 Hz, SCH₂), 3.57 (3H, s, OCH₃), 4.46 (1H, m, NCH), 5.70 (1H, s, =CHCO), 6.13–6.26 [3H, m, CH=CHC(CH₃)=CHCH=CH], 6.88 [1H, dd, J 15.4, 11.4 Hz, CH=CHC(CH₃)=CHCO], 7.84 [1H, d, J 15.4 Hz, CHC(CH₃)=CHCO], 8.16 (1H, d, J 6.4 Hz, NH).

Compound (II-1b):

Yield: 60%. R_f 0.30–0.35. ¹H-NMR (CD₃SOCD₃, 400 MHz) δ 1.00 [6H, s, C(CH₃)₂], 1.16 (3H, t, J 7.1 Hz, CH₃CH₂), 1.42 and 1.56 [2H+2H, 2 m, CH₂CH₂C(CH₃)₂], 1.67 [3H, s, CH₃C=CC(CH₃)₂]1, 1.95 and 1.98 (3H+3H, 2 s, CH₃C=(CH)₃C(CHH₃)=CHCO], 2.00 (2H, m, CH₂C=), 2.80 (2H, d, J 6.2 Hz, SCH₂), 4.04 (2H, q, J 7.1 Hz, OCH₂), 4.41 (1H, m, NCH), 5.86 (1H, s, =CHCO), 6.13–6.26 [3H, m, CH=CHC(CH₃)=CHCH=CH], 6.88 [1H, dd, J 15.4 11.5 Hz, CH=CHC(CH₃)=CHCO], 7.83 [1H, d, J 15.4 Hz, CHC(CH₃)=CHCO], 8.12 (1H, d, J 6.2 Hz, NH).

Compound (II-1c):

Yield: 55%. R_f 0.35–0.40. ¹H-NMR (CD₃SOCD₃, 400 MHz) δ 1.00 [6H, s, C(CH₃)₂], 1.14 and 1.17 [3H+3H, 2 d, J 6.2 Hz, (C$\underline{H}_3$)$_2$CHO], 1.42 and 1.56 [2H+2H, 2m, C$\underline{H}_2$C$\underline{H}_2$C(CH$_3$)$_2$], 1.67 [3H, s, C$\underline{H}_3$C=CC(CH$_3$)$_2$], 1.95 and 1.98 (3H+3H, 2 s, C$\underline{H}_3$C=(CH)$_3$C(C$\underline{H}_3$)=CHCO], 1.99 (2H, m, C$\underline{H}_2$C=), 2.78 (2H, d, J 6.0 Hz, SC$\underline{H}_2$), 4.36 (1H, m, NC$\underline{H}$), 4.84 (1H, m, OC$\underline{H}$) 5.68 (1H, s, =C$\underline{H}$CO), 6.13–6.26 [3H, m, C$\underline{H}$=C$\underline{H}$C(CH$_3$)=C$\underline{H}$CH=CH], 6.87 [1H, dd, J 15.2, 11.4 Hz, C$\underline{H}$=CHC(CH$_3$)=CHCO], 7.82 [1H, d, J 15.2 Hz, C$\underline{H}$C(CH$_3$)=CHCO], 8.08 (1H, d, J 6.0 Hz, N$\underline{H}$).

Compound (II-1d):

Yield: 58%. R$_f$ 0.40–0.45. $^1$H-NMR (CD$_3$SOCD$_3$, 400 MHz) δ 0.86 (3H, t, J 7.3 Hz, C$\underline{H}_3$CH$_2$), 1.00 [6H, s, C(C$\underline{H}_3$)$_2$], 1.42 and 1.56 [2H+2H, 2 m, C$\underline{H}_2$C$\underline{H}_2$C(CH$_3$)$_2$], 1.55 (2H, m, C$\underline{H}_2$CH$_3$), 1.67 [3H, s, C$\underline{H}_3$C=CC(CH$_3$)$_2$], 1.95 and 1.98 (3H+3H, 2 s, C$\underline{H}_3$C=(CH)$_3$C(C$\underline{H}_3$)=CHCO], 1.99 (2H, m, C$\underline{H}_2$C=), 2.81 (2H, d, J6.0 Hz, SC$\underline{H}_2$), 3.95 (2H, m, OC$\underline{H}_2$), 4.42 (1H, m, NC$\underline{H}$), 5.69 (1H, s, =C$\underline{H}$CO), 6.13–6.27 [3H, m, C$\underline{H}$=C$\underline{H}$C(CH$_3$)=C$\underline{H}$CH=CH], 6.87 [1H, dd, J 15.4, 11.4 Hz, C$\underline{H}$=CHC(CH$_3$)=CHCO], 7.83 [1H d, J 15.4 Hz, C$\underline{H}$C(CH$_3$)=CHCO], 8.13 (1H, d, J 6.2 Hz, N$\underline{H}$).

Compound (II-1e):

Yield: 59%. R$_f$ 0.35–0.40. $^1$H-NMR (CD$_3$SOCD$_3$, 400 MHz) δ 0.86 (3H, t, J 7.4 Hz, C$\underline{H}_3$CH$_2$), 1.00 [6H, s, C(C$\underline{H}_3$)$_2$], 1.30 (2H, m, C$\underline{H}_2$CH$_3$), 1.43 and 1.55 [2H+2H, 2 m, C$\underline{H}_2$C$\underline{H}_2$C(CH$_3$)$_2$], 1.52 (2H, m, C$\underline{H}_2$CH$_2$O), 1.67 [3H, s, C$\underline{H}_3$C=CC(CH$_3$)$_2$], 1.95 and 1.98 (3H+3H, 2 s, C$\underline{H}_3$C=(CH)$_3$C(C$\underline{H}_3$)=CHCO], 1.99 (2H, m, C$\underline{H}_2$C=), 2.80 (2H, d, J 6.1 Hz, SC$\underline{H}_2$), 3.98 (2H, m, OC$\underline{H}_2$), 4.41 (1H, m, NC$\underline{H}$), 5.68 (1H, s, =C$\underline{H}$CO), 6.13–6.26 [3H, m, C$\underline{H}$=C$\underline{H}$C(CH$_3$)=C$\underline{H}$CH=CH], 6.87 [1H, dd, J 15.4, 11.4 Hz, C$\underline{H}$=CHC(CH$_3$)=CHCO], 7.82 [1H, d, J 15.4 Hz, C$\underline{H}$C(CH$_3$)=CHCO], 8.13 (1H, d, J 6.2 Hz, N$\underline{H}$).

Compound (II-1f):

Yield: 34%. R$_f$ 0.10–0.15. $^1$H-NMR (CD$_3$SOCD$_3$, 400 MHz) δ 1.00 [6H, s, C(CH$_3$)$_2$], 1.43 and 1.56 [2H+2H, 2 m, C$\underline{H}_2$C$\underline{H}_2$C(CH$_3$)$_2$], 1.67 [3H, s, C$\underline{H}_3$C=CC(CH$_3$)$_2$], 1.95 and 1.97 [3H+3H, 2 s, C$\underline{H}_3$C=(CH)$_3$C(C$\underline{H}_3$)=CHCO], 1.99 (2H, m, C$\underline{H}_2$C=), 2.71 (1H, dd, J 13.9, 7.9 Hz, SC$\underline{H}^a$H$^b$), 2.82 (1H, dd, J 13.9, 4.9 Hz, SCH$^a$$\underline{H}^b$), 4.33 (1H, m, NC$\underline{H}$), 5.68 (1H, s, =C$\underline{H}$CO), 6.12–6.26 [3H, m, C$\underline{H}$=C$\underline{H}$C(CH$_3$)=C$\underline{H}$CH=CH], 6.87 [1H, dd, J 15.6, 11.3 Hz, C$\underline{H}$=CHC(CH$_3$)=CHCO], 6.90 (1H, br s, N$\underline{H}^a$H$^b$), 7.33 (1H, br s, NH$^a$$\underline{H}^b$), 7.88 [1H, d, J 15.6 Hz, C$\underline{H}$C(CH$_3$)=CHCO], 7.96 (1H, d, J 6.2 Hz, N$\underline{H}$CH).

Compound (II-3b):

Yield: 54%. R$_f$ 0.30–0.35. $^1$H-NMR (CD$_3$SOCD$_3$, 400 MHz) δ 1.00 [6H, s, C(CH$_3$)$_2$], 1.17 (3H, t, J 7.1 Hz, C$\underline{H}_3$CH$_2$), 1.42 and 1.56 [2H+2H, 2 m, C$\underline{H}_2$C$\underline{H}_2$C(CH$_3$)$_2$], 1.67 [3H, s, C$\underline{H}_3$C=CC(CH$_3$)$_2$], 1.84–2.11 (2H, br m, C$\underline{H}_2$CH$_2$S), 1.95 and 1.97 (3H+3H, 2 s, C$\underline{H}_3$C=(CH)$_3$C(C$\underline{H}_3$)=CHCO], 1.99 (2H, m, C$\underline{H}_2$C=), 2.46 (2H, m, SC$\underline{H}_2$), 4.07 (2H, m, OC$\underline{H}_2$), 4.24 (1H, m, NC$\underline{H}$), 5.75 (1H, s, =C$\underline{H}$CO), 6.12–6.26 [3H, m, C$\underline{H}$=C$\underline{H}$C(CH$_3$)=C$\underline{H}$CH=CH], 6.87 [1H, dd, J 15.4, 11.4 Hz, C$\underline{H}$=CHC(CH$_3$)=CHCO], 7.86 [1H, d, J 15.4 Hz, C$\underline{H}$C(CH$_3$)=CHCO], 8.41 (1H, d, J 7.0 Hz, N$\underline{H}$).

Example 2

Evaluation of the Cytotoxicity of Compound I-1a in Cultures of Human Breast Adenocarcinoma MDA-MB-231 Cell Line Related to the Final Concentration of Compound I-1a in the Cultures An initial solution of compound I-1a (1 mg/ml) was prepared by dissolving the dry substance in saline. From this solution, the working solutions of compound I-1a in MEM with 5% FBS were prepared in different concentrations by means of consecutive dilutions for adding to the cultures.

Cultures of MDA-MB-231 cells were treated with drug solutions on day 1 after seeding. Aliquots of the working solutions (2 μL) in different concentrations of compound I-1a were added to 200 μL cultures to a final concentration of compound I-1a from $10^{-9}$ to $10^{-7}$ mol/L in the cultures. In the control cultures, 2 μL medium with 5% FBS was added as solvent control. After cultivation for two consecutive days, the number of viable cells in the cultures was counted and the extent of growth inhibition of MDA-MB-231 cells calculated in order to evaluate the cytotoxicity of the tested solutions of compound I-1a.

After three days of cultivation, the control cultures contained $(57.2\pm3.00)\times10^3$ cells.

The cultures, treated by solutions of compound I-1a had the following number of viable cells:

| | |
|---|---|
| $10^{-9}$ mol/L: | $(34.3 \pm 2.27) \times 10^3$, cell growth inhibition was 40.0% ($p < 0.001$); |
| $10^{-8}$ mol/L: | $(31.1 \pm 1.90) \times 10^3$, cell growth inhibition was 45.6% ($p < 0.001$); |
| $10^{-7}$ mol/L: | $(29.8 \pm 2.44) \times 10^3$, cell growth inhibition was 47.9% ($p < 0.001$). |

Thus compound I-1a was shown to exert a significant cytotoxic action against human breast adenocarcinoma cells. The extent of cell growth inhibition increased by 47.9% ($p<0.001$) when increasing the concentration of compound I-1a.

Example 3

Evaluation of the Cytotoxicity of Compound I-1b in Cultures of Human Breast Adenocarcinoma MDA-MB-231 Cell Line Related to the Final Concentration of Compound I-1b in Cultures An initial solution of compound I-1b (1 mg/ml) was prepared by dissolving the dry substance in saline. From this solution, the working solutions of compound I-1b in MEM with 5% FBS were prepared in different concentrations by means of consecutive dilutions for adding to the cultures.

Cultures of MDA-MB-231 cells were treated with drug solutions on day 1 after seeding. Aliquots of working solutions (2 μL) in different concentrations of compound I-1b were added to 200 μL cultures to a final concentration of compound I-1b from $10^{-9}$ to $10^{-7}$ mol/L in the cultures. In the control cultures, 2 μL of medium with 5% FBS was added as solvent control. After cultivation for two consecutive days, the number of viable cells in cultures was counted and the extent of growth inhibition of MDA-MB-231 cells calculated in order to evaluate the cytotoxicity of the tested solutions of compound I-1b.

After three days of cultivation, the control cultures contained $(57.2\pm3.00)\times10^3$ cells.

The cultures, treated by solutions of compound I-1b had the following number of viable cells:

| | |
|---|---|
| $10^{-9}$ mol/L: | $(34.8 \pm 2.41) \times 10^3$, cell growth inhibition was 39.2% ($p < 0.001$); |
| $10^{-8}$ mol/L: | $(31.9 \pm 2.16) \times 10^3$, cell growth inhibition was 44.2% ($p < 0.001$); |
| $10^{-7}$ mol/L: | $(30.5 \pm 1.82) \times 10^3$, cell growth inhibition was 46.7% ($p < 0.001$). |

Thus compound I-1b was shown to exert a significant cytotoxic action against human breast adenocarcinoma cells. The extent of cell growth inhibition increased by 46.7% (p<0.001) when increasing the concentration of compound I-1b.

Example 4

Evaluation of the Cytotoxicity of Compound I-1c in Cultures of Human Breast Adenocarcinoma MDA-MB-231 Cell Line Related to the Final Concentration of Compound I-1c in Cultures An initial solution of compound I-1c (1 mg/ml) was prepared by dissolving the dry substance in saline. From this solution, the working solutions of compound I-1c in MEM with 5% FBS were prepared in different concentrations by means of consecutive dilutions for adding to the cultures.

Cultures of MDA-MB-231 cells were treated with drug solutions on day 1 after seeding. Aliquots of working solutions (2 µL) in different concentrations of compound I-1c were added to 200 µL cultures to a final concentration of compound I-1c from $10^{-9}$ to $10^{-7}$ mol/L in the cultures. In the control cultures, 2 µL of medium with 5% FBS was added as solvent control. After cultivation for two consecutive days, the number of viable cells in cultures was counted and the extent of growth inhibition of MDA-MB-231 cells calculated in order to evaluate the cytotoxicity of the tested solutions of compound I-1c.

After three days of cultivation, the control cultures contained $(57.2\pm3.00)\times10^3$ cells.

The cultures, treated by solutions of compound I-1c had the following number of viable cells:

| | |
|---|---|
| $10^{-9}$ mol/L: | $(34.0 \pm 2.13) \times 10^3$, cell growth inhibition was 40.6% (p < 0.001); |
| $10^{-8}$ mol/L: | $(30.4 \pm 1.79) \times 10^3$, cell growth inhibition was 46.9% (p < 0.001); |
| $10^{-7}$ mol/L: | $(28.9 \pm 1.52) \times 10^3$, cell growth inhibition was 49.5% (p < 0.001). |

Thus compound I-1c was shown to exert a significant cytotoxic action against human breast adenocarcinoma cells. The extent of cell growth inhibition increased by 49.5% (p<0.001) when increasing the concentration of compound I-1c.

Example 5

Evaluation of the Cytotoxicity of Compound I-1d in Cultures of Human Breast Adenocarcinoma MDA-MB-231 Cell Line Related to the Final Concentration of Compound I-1d in Cultures An initial solution of compound I-1d (1 mg/ml) was prepared by dissolving the dry substance in saline. From this solution, the working solutions of compound I-1d in MEM with 5% FBS were prepared in different concentrations by means of consecutive dilutions for adding to the cultures.

Cultures of MDA-MB-231 cells were treated with drug solutions on day 1 after seeding. Aliquots of working solutions (2 µL) with different concentrations of compound I-1d were added to 200 µL cultures to a final concentration of compound I-1d from $10^{-9}$ to $10^{-7}$ mol/L in the cultures. In the control cultures, 2 µL of medium with 5% FBS was added as solvent control. After cultivation for two consecutive days, the number of viable cells in cultures was counted and the extent of growth inhibition of MDA-MB-231 cells calculated in order to evaluate the cytotoxicity of the tested solutions of compound I-1d.

After three days of cultivation, the control cultures contained $(53.3\pm2.66)\times10^3$ cells.

The cultures, treated by solutions of compound I-1d had the following number of viable cells:

| | |
|---|---|
| $10^{-9}$ mol/L: | $(29.2 \pm 1.89) \times 10^3$, cell growth inhibition was 45.2% (p < 0.001); |
| $10^{-8}$ mol/L: | $(26.3 \pm 1.67) \times 10^3$, cell growth inhibition was 50.7% (p < 0.001); |
| $10^{-7}$ mol/L: | $(24.1 \pm 1.46) \times 10^3$, cell growth inhibition was 54.8% (p < 0.001). |

Thus compound I-1d was shown to exert a significant cytotoxic action against human breast adenocarcinoma cells. The extent of cell growth inhibition increased by 54.8% (p<0.001) when increasing the concentration of compound I-1d.

Example 6

Evaluation of the Cytotoxicity of Compound I-1e in Cultures of Human Breast Adenocarcinoma MDA-MB-231 Cell Line Related to the Final Concentration of Compound I-1e in Cultures An initial solution of compound I-1e (1 mg/ml) was prepared by dissolving the dry substance in saline. From this solution, the working solutions of compound I-1e in MEM with 5% FBS were prepared in different concentrations by means of consecutive dilutions for adding to the cultures.

Cultures of MDA-MB-231 cells were treated with-drug solutions on day 1 after seeding. Aliquots of working solutions (2 µL) in different concentrations of compound I-1e were added to 200 µL cultures to a final concentration of compound I-1e from $10^{-9}$ to $10^{-7}$ mol/L in the cultures. In the control cultures, 2 µL of medium with 5% FBS was added as solvent control. After cultivation for two consecutive days, the number of viable cells in cultures was counted and the extent of growth inhibition of MDA-MB-231 cells calculated in order to evaluate the cytotoxicity of the tested solutions of compound I-1e.

After three days of cultivation, the control cultures contained $(53.3\pm2.66)\times10^3$ cells.

The cultures, treated by solutions of compound I-1e had the following number of viable cells:

| | |
|---|---|
| $10^{-9}$ mol/L: | $(29.5 \pm 2.18) \times 10^3$, cell growth inhibition was 44.7% (p < 0.001); |
| $10^{-8}$ mol/L: | $(27.1 \pm 1.75) \times 10^3$, cell growth inhibition was 49.2% (p < 0.001); |
| $10^{-7}$ mol/L: | $(24.8 \pm 1.34) \times 10^3$, cell growth inhibition was 53.5% (p < 0.001). |

Thus compound I-1e was shown to exert a significant cytotoxic action against human breast adenocarcinoma cells. The extent of cell growth inhibition increased by 53.5% (p<0.001) when increasing the concentration of compound I-1e.

Example 7

Evaluation of the Cytotoxicity of Compound I-1f in Cultures of Human Breast Adenocarcinoma MDA-MB-231 Cell Line Related to the Final Concentration of Compound I-1f in Cultures An initial solution of compound I-1f (1 mg/ml) was prepared by dissolving the dry substance in saline. From this solution, the working solutions of compound I-1f in MEM with 5% FBS were prepared in different concentrations by means of consecutive dilutions for adding to the cultures.

Cultures of MDA-MB-231 cells were treated with drug solutions on day 1 after seeding. Aliquots of the working solutions (2 µL) with different concentrations of compound I-1f were added to 200 µL cultures to a final concentration of compound I-1f from $10^{-9}$ to $10^{-7}$ mol/L in cultures. In the control cultures, 2 µL of medium with 5% FBS was added as solvent control. After cultivation for two consecutive days, the number of viable cells in cultures was counted and the extent of growth inhibition of MDA-MB-231 cells calculated in order to evaluate the cytotoxicity of the tested solutions of compound I-1f.

After three days of cultivation, the control cultures contained $(53.3\pm2.66)\times10^3$ cells.

The cultures, treated by solutions of compound I-1f had the following number of viable cells:

| | |
|---|---|
| $10^{-9}$ mol/L: | $(29.4 \pm 2.15) \times 10^3$, cell growth inhibition was 44.8% ($p < 0.001$); |
| $10^{-8}$ mol/L: | $(27.4 \pm 1.42) \times 10^3$, cell growth inhibition was 48.6% ($p < 0.001$); |
| $10^{-7}$ mol/L: | $(25.3 \pm 1.11) \times 10^3$, cell growth inhibition was 52.5% ($p < 0.001$). |

Thus compound I-1f was shown to exert a significant cytotoxic action against human breast adenocarcinoma cells. The extent of cell growth inhibition increased by 52.5% ($p<0.001$) when increasing the concentration of compound I-1f.

Example 8

Evaluation of the Cytotoxicity of Compound II-1a in Cultures of Human Breast Adenocarcinoma MDA-MB-231 Cell Line Related to the Final Concentration of Compound II-1a in Cultures An initial solution of compound II-1a (1 mg/ml) was prepared by dissolving the dry substance in saline. From this solution, the working solutions of compound II-1a in MEM with 5% FBS were prepared in different concentrations by means of consecutive dilutions for adding to the cultures.

Cultures of MDA-MB-231 cells were treated with drug solutions on day 1 after seeding. Aliquots of working solutions (2 µL) in different concentrations of compound II-1a were added to 200 µL cultures to a final concentration of compound II-1a from $10^{-9}$ to $10^{-7}$ mol/L in cultures. In the control cultures, 2 µL of medium with 5% FBS was added as solvent control. After cultivation for two consecutive days, the number of viable cells in cultures was counted and the extent of growth inhibition of MDA-MB-231 cells calculated in order to evaluate the cytotoxicity of the tested solutions of compound II-1a.

After three days of cultivation, the control cultures contained $(58.5\pm3.35)\times10^3$ cells.

The cultures, treated by solutions of compound II-1a had the following number of viable cells:

| | |
|---|---|
| $10^{-9}$ mol/L: | $(35.8 \pm 2.50) \times 10^3$, cell growth inhibition was 38.8% ($p < 0.001$); |
| $10^{-8}$ mol/L: | $(32.7 \pm 2.06) \times 10^3$, cell growth inhibition was 44.1% ($p < 0.001$); |
| $10^{-7}$ mol/L: | $(31.3 \pm 2.15) \times 10^3$, cell growth inhibition was 46.5% ($p < 0.001$). |

Thus compound II-1a was shown to exert a significant cytotoxic action against human breast adenocarcinoma cells. The extent of cell growth inhibition increased by 46.5% ($p<0.001$) when increasing the concentration of compound II-1a.

Example 9

Evaluation of the Cytotoxicity of Compound II-1b in Cultures of Human Breast Adenocarcinoma MDA-MB-231 Cell Line Related to the Final Concentration of Compound I-I1b in Cultures An initial solution of compound II-1b (1 mg/ml) was prepared by dissolving the dry substance in saline. From this solution, the working solutions of compound II-1b in MEM with 5% FBS were prepared in different concentrations by means of consecutive dilutions for adding to the cultures.

Cultures of MDA-MB-231 cells were treated with drug solutions on day 1 after seeding. Aliquots of working solutions (2 µL) in different concentrations of compound II-1b were added to 200 µL cultures to a final concentration of compound II-1b from $10^{-9}$ to $10^{-7}$ mol/L in cultures. In the control cultures, 2 µL of medium with 5% FBS was added as solvent control. After cultivation for two consecutive days, the number of viable cells in cultures was counted and the extent of growth inhibition of MDA-MB-231 cells calculated in order to evaluate the cytotoxicity of the tested solutions of compound II-1b.

After three days of cultivation, the control cultures contained $(58.5\pm3.35)\times10^3$ cells.

The cultures, treated by solutions of compound II-1b had the following number of viable cells:

| | |
|---|---|
| $10^{-9}$ mol/L: | $(34.3 \pm 1.88) \times 10^3$, cell growth inhibition was 41.4% ($p < 0.001$); |
| $10^{-8}$ mol/L: | $(31.4 \pm 1.94) \times 10^3$, cell growth inhibition was 46.3% ($p < 0.001$); |
| $10^{-7}$ mol/L: | $(29.8 \pm 1.70) \times 10^3$, cell growth inhibition was 49.1% ($p < 0.001$). |

Thus compound II-1b was shown to exert a significant cytotoxic action against human breast adenocarcinoma cells. The extent of cell growth inhibition increased by 49.1% ($p<0.001$) when increasing the concentration of compound II-1b.

Example 10

Evaluation of the Cytotoxicity of Compound II-1c in Cultures of Human Breast Adenocarcinoma MDA-MB-231 Cell Line Related to the Final Concentration of compound II-1c in Cultures An initial solution of compound II-1c (1 mg/ml) was prepared by dissolving the dry substance in saline. From this solution, the working solutions of compound II-1c in MEM with 5% FBS were prepared in different concentrations by means of consecutive dilutions for adding to the cultures.

Cultures of MDA-MB-231 cells were treated with drug solutions on day 1 after seeding. Aliquots of working solutions (2 µL) in different concentrations of compound II-1c were added to 200 µL cultures to a final concentration of compound II-1c from $10^{-9}$ to $10^{-7}$ mol/L in cultures. In the control cultures, 2 µL of medium with 5% FBS was added as solvent control. After cultivation for two consecutive days, the number of viable cells in cultures was counted and the extent of growth inhibition of MDA-MB-231 cells calculated in order to evaluate the cytotoxicity of the tested solutions of compound II-1c.

After three days of cultivation, the control cultures contained $(58.5 \pm 3.35) \times 10^3$ cells.

The cultures, treated by solutions of compound II-1c had the following number of viable cells:

| | |
|---|---|
| $10^{-9}$ mol/L: | $(33.6 \pm 2.75) \times 10^3$, cell growth inhibition was 42.6% ($p < 0.001$); |
| $10^{-8}$ mol/L: | $(31.0 \pm 2.05) \times 10^3$, cell growth inhibition was 47.0% ($p < 0.001$); |
| $10^{-7}$ mol/L: | $(29.0 \pm 1.26) \times 10^3$, cell growth inhibition was 50.4% ($p < 0.001$). |

Thus compound II-1c was shown to exert a significant cytotoxic action against human breast adenocarcinoma cells. The extent of cell growth inhibition increased by 50.4% ($p<0.001$) when increasing the concentration of compound II-1c.

Example 11

Evaluation of the Cytotoxicity of Compound II-1d in Cultures of Human Breast Adenocarcinoma MDA-MB-231 Cell Line Related to the Final Concentration of Compound II-1d in Cultures An initial solution of compound II-1d (1 mg/ml) was prepared by dissolving the dry substance in saline. From this solution, the working solutions of compound II-1d in MEM with 5% FBS were prepared in different concentrations by means of consecutive dilutions for adding to the cultures.

Cultures of MDA-MB-231 cells were treated with drug solutions on day 1 after seeding. Aliquots of working solutions (2 µL) in different concentrations of compound II-1d were added to 200 µL cultures to a final concentration of compound II-1d from $10^{-9}$ to $10^{-7}$ mol/L in cultures. In the control cultures, 2 µL of medium with 5% FBS was added as solvent control. After cultivation for two consecutive days, the number of viable cells in cultures was counted and the extent of growth inhibition of MDA-MB-231 cells calculated in order to evaluate the cytotoxicity of the tested solutions of compound II-1d.

After three days of cultivation, the control cultures contained $(56.8 \pm 3.16) \times 10^3$ cells.

The cultures, treated by solutions of compound II-1d had the following number of viable cells:

| | |
|---|---|
| $10^{-9}$ mol/L: | $(31.3 \pm 2.68) \times 10^3$, cell growth inhibition was 44.9% ($p < 0.001$); |
| $10^{-8}$ mol/L: | $(28.2 \pm 1.29) \times 10^3$, cell growth inhibition was 50.4% ($p < 0.001$); |
| $10^{-7}$ mol/L: | $(26.3 \pm 1.86) \times 10^3$, cell growth inhibition was 53.7% ($p < 0.001$). |

Thus compound II-1d was shown to exert a significant cytotoxic action against human breast adenocarcinoma cells. The extent of cell growth inhibition increased by 53.7% ($p<0.001$) when increasing the concentration of compound II-1d.

Example 12

Evaluation of the Cytotoxicity of Compound II-1e in Cultures of Human Breast Adenocarcinoma MDA-MB-231 Cell Line Related to the Final Concentration of Compound II-1e in Cultures An initial solution of compound II-1e (1 mg/ml) was prepared by dissolving the dry substance in saline. From this solution, the working solutions of compound II-1e in MEM with 5% FBS were prepared in different concentrations by means of consecutive dilutions for adding to the cultures.

Cultures of MDA-MB-231 cells were treated with drug solutions on day 1 after seeding. Aliquots of working solutions (2 µL) in different concentrations of compound II-1e were added to 200 µL cultures to a final concentration of compound II-1e from $10^{-9}$ to $10^{-7}$ mol/L in cultures. In control cultures 2 µL of medium with 5% FBS was added as solvent control. After cultivation for two consecutive days, the number of viable cells in cultures was counted and the extent of growth inhibition of MDA-MB-231 cells calculated in order to evaluate the cytotoxicity of the tested solutions of compound II-1e.

After three days of cultivation, the control cultures contained $(56.8 \pm 3.16) \times 10^3$ cells.

The cultures, treated by solutions of compound II-1e had the following number of viable cells:

| | |
|---|---|
| $10^{-9}$ mol/L: | $(30.9 \pm 1.82) \times 10^3$, cell growth inhibition was 45.6% ($p < 0.001$); |
| $10^{-8}$ mol/L: | $(28.0 \pm 1.34) \times 10^3$, cell growth inhibition was 50.7% ($p < 0.001$); |
| $10^{-7}$ mol/L: | $(26.0 \pm 1.27) \times 10^3$, cell growth inhibition was 54.2% ($p < 0.001$). |

Thus compound II-1e was shown to exert a significant cytotoxic action against human breast adenocarcinoma cells. The extent of cell growth inhibition increased by 54.2% ($p<0.001$) when increasing the concentration of compound II-1e.

Example 13

Evaluation of the Cytotoxicity of Compound II-1f in Cultures of Human Breast Adenocarcinoma MDA-MB-231 Cell Line Related to the Final Concentration of Compound II-1f in Cultures An initial solution of compound II-1f (1 mg/ml) was prepared by dissolving the dry substance in saline. From this solution, the working solutions of compound II-1f in MEM with 5% FBS were prepared in different concentrations by means of consecutive dilutions for adding to the cultures.

Cultures of MDA-MB-231 cells were treated with drug solutions on day 1 after seeding. Aliquots of working solutions (2 µL) in different concentrations of compound II-1f were added to 200 µL cultures to a final concentration of compound II-1f from $10^{-9}$ to $10^{-7}$ mol/L in cultures. In control cultures 2 µL of medium with 5% FBS was added as solvent control. After cultivation for two consecutive days, the number of viable cells in cultures was counted and the extent of growth inhibition of MDA-MB-231 cells calculated in order to evaluate the cytotoxicity of the tested solutions of compound II-1f.

After three days of cultivation the control cultures contained $(56.8\pm3.16)\times10^3$ cells.

The cultures, treated by solutions of compound II-1f had the following number of viable cells:

| | |
|---|---|
| $10^{-9}$ mol/L: | $(31.2 \pm 2.42) \times 10^3$, cell growth inhibition was 45.1% (p < 0.001); |
| $10^{-8}$ mol/L: | $(28.5 \pm 2.13) \times 10^3$, cell growth inhibition was 49.8% (p < 0.001); |
| $10^{-7}$ mol/L: | $(26.6 \pm 1.83) \times 10^3$, cell growth inhibition was 53.2% (p < 0.001). |

Thus compound II-1f was shown to exert a significant cytotoxic action against human breast adenocarcinoma cells. The extent of cell growth inhibition increased by 53.2% (p<0.001) when increasing the concentration of compound II-1f.

Example 14

Evaluation of the Cytotoxicity of the Formulation Docetaxel/Compound I-1 in Cultures of Human Breast Adenocarcinoma MDA-MB-231 Cell Line, Related to Molar Ratios Docetaxel:compound I-1

The sodium salt of compound I-1 was converted into the acidic form of compound I-1 and dissolved in methanol. A solution of docetaxel in methanol was mixed with a solution of compound I-1 in methanol. After stirring, the organic solvent was evaporated. The resulting dried film was dissolved in saline.

Initial solutions of the formulation in saline at the molar ratios docetaxel:compound I-1 equal to 1:3, 1:6 and 1:10 were prepared. From these solutions the working solutions in medium with 5% FBS for adding to cultures were prepared. The concentration of docetaxel was equal to $10^{-5}$ M.

Cultures of MDA-MB-231 cells were treated with drug solutions on day 1 after seeding. Aliquots of the working solutions (2 µL) were added to 200 µL cultures to a final concentration of docetaxel in cultures equal to $10^{-7}$ M. In the control cultures 2 µL of medium with 5% FBS was added as solvent control. After cultivation for two consecutive days, the number of viable cells in cultures was counted in order to evaluate the cytotoxicity of the tested solutions of the formulation.

After three days of cultivation the control cultures of contained $(57.6\pm3.04)\times10^3$ cells.

The cultures, treated by docetaxel in a concentration of 100 nM, contained $(15.4\pm1.02)\times10^3$ cells, cell growth inhibition was 73.3% (p<0.001).

The cultures of MDA-MB-231 cells, treated by solutions of the formulation at the molar ratio docetaxel/compound I-1 equal to 1:3, 1:6, and 1:10 in medium with 5% FBS, had the following number of viable cells:

1:3: $(9.3\pm0.75)\times10^3$, cell growth inhibition was 83.9% (p<0.001), cell growth inhibition compared to that of docetaxel was increased by 39.6% (p<0.001);

1:6: $(8.4\pm0.53)\times10^3$, cell growth inhibition was 85.4% (p<0.001), cell growth inhibition compared to that of docetaxel was increased by 45.5% (p<0.001);

1:10: $(7.8\pm0.61)\times10^3$, cell growth inhibition was 86.5% (p<0.001), cell growth inhibition compared to that of docetaxel was increased by 49.4% (p<0.001)

Example 15

Evaluation of the Cytotoxicity of the Formulation Docetaxel/Compound I-1 in Cultures of Human Breast Adenocarcinoma MDA-MB-231 Cell Line at Molar Ratio Docetaxel:Compound I-1 (1:6) Related to the Final Concentration of Docetaxel/Compound I-1 in Cultures The sodium salt of compound I-1 was converted into the acidic form of compound I-1 and dissolved in methanol. A solution of docetaxel in methanol was mixed with a solution of compound I-1 in methanol. After stirring the organic solvent was evaporated. The resulting dried film was dissolved in saline.

From this initial solution the working solutions in medium with 5% FBS for adding to cultures were prepared. Cultures of MDA-MB-231 cells were treated with drug solutions on day 1 after seeding. Aliquots of working solutions (2 µL) with different concentrations of formulation were added to 200 µL cultures to a final concentration of docetaxel $1\times10^{-9}$, $1\times10^{-8}$ and $1\times10^{-7}$ mol/L in the cultures. In control cultures 2 µL of medium with 5% FBS was added as solvent control. After cultivation for two consecutive days, the number of viable cells in cultures was counted in order to evaluate the cytotoxicity of the tested solutions of the formulation (Table 1).

TABLE 1

Evaluation of the cytotoxicity of the formulation
docetaxel/compound I-1 in cultures of human breast
adenocarcinoma MDA-MB-231 cell line at molar ratio
docetaxel:compound I-1 (1:6) related to the final concentration
of docetaxel/compound I-1 in cultures

| Drug | Formulation | | Tumor Cell Number, × $10^3$ | Cell growth Inhibition, % | Positive Effect, % | $IC_{50}$ mol/L (a) |
|---|---|---|---|---|---|---|
| | Docetaxel, mol/L | Compound I-1, mol/L | | | | |
| Control | 0 | 0 | 55.8 ± 1.99 | — | — | — |
| Docetaxel | $10^{-9}$ | 0 | 34.2 ± 2.28 | 38.7* | — | $3.6 \times 10^{-9}$ |
| | $10^{-8}$ | 0 | 23.4 ± 2.15 | 58.1* | — | |
| | $10^{-7}$ | 0 | 13.7 ± 1.03 | 75.4* | — | |
| Formulation | $10^{-9}$ | $6 \times 10^{-9}$ | 25.6 ± 1.34 | 54.1* | +25.1** | $6.3 \times 10^{-10}$ (b) |
| | $10^{-8}$ | $6 \times 10^{-8}$ | 14.9 ± 1.09 | 73.3* | +36.3** | |
| | $10^{-7}$ | $6 \times 10^{-7}$ | 7.2 ± 0.65 | 87.1* | +47.4* | |

(a) Cell growth inhibition data, determined at three different concentrations, were used to calculate the drug concentrations that inhibited cell growth by 50% as compared to untreated control cultures. All data are the means of three determinations each in six replicates.
(b) Extrapolated.
*p < 0.001
**p < 0.01

Example 16

Evaluation of the Cytotoxicity of the Formulation Docetaxel/Compound I-1a in Cultures of Human Prostate Carcinoma DU 145 Cell Line Related to Molar Ratios docetaxel:Compound I-1a An aliquot of a stock solution of the sodium salt of compound I-1a (2 mg) in ethanol-water (2:1, v/v) was evaporated on a rotary evaporator under reduced pressure. The resulting dried film was dissolved in methanol. A solution of docetaxel in methanol and the solution of compound I-1a in methanol was mixed. After stirring the organic solvent was evaporated. The resulting dried film was dissolved in saline.

Initial solutions of the formulation in saline at the molar ratios docetaxel:compound I-1a equal to 1:3, 1:6 and 1:10 were prepared. From these solutions the working solutions in medium with 5% FBS for adding to cultures were prepared. The concentration of docetaxel was equal to $10^{-5}$ M.

Cultures of DU 145 cells were treated with drug solutions on day 1 after seeding. Aliquots of the working solutions (2 μL) were added to 200 μL cultures to a final concentration of docetaxel in the cultures equal to $10^{-7}$ M. In the control cultures, 2 μL of medium with 5% FBS was added as solvent control. After cultivation for two consecutive days, the number of viable cells in cultures was counted in order to evaluate the cytotoxicity of the tested solutions of the formulation.

After three days of cultivation, the control cultures contained (55.7±2.69)×$10^3$ cells.

The cultures, treated by docetaxel in a concentration of 100 nM, contained (14.2±0.85)×$10^3$ cells, cell growth inhibition was 74.5% (p<0.001).

The cultures of DU 145 cells, treated by solutions of the formulation at the molar ratio docetaxel/compound I-1a equal to 1:3, 1:6, and 1:10 in medium with 5% FBS, had the following number of viable cells:

1:3: (8.0±0.69)×$10^3$, cell growth inhibition was 85.6% (p<0.001), cell growth inhibition compared to that of docetaxel was increased by 43.7% (p<0.001);

1:6: (7.2±0.66)×$10^3$, cell growth inhibition was 87.1% (p<0.001), cell growth inhibition compared to that of docetaxel was increased by 49.3% (p<0.001);

1:10: (6.4±0.52)×$10^3$, cell growth inhibition was 88.5% (p<0.001), cell growth inhibition compared to that of docetaxel was increased by 54.9% (p<0.001).

Example 17

Evaluation of the Cytotoxicity of the Formulation Docetaxel/Compound I-1a in Cultures of Human Prostate Carcinoma DU 145 Cell Line at Molar Ratio Docetaxel:Compound I-1a (1:6) Related to the Final Concentration of Docetaxel/Compound I-1a in Cultures An aliquot of a stock solution of the sodium salt of compound I-1a (2 mg) in ethanol-water (2:1, v/v) was evaporated on a rotary evaporator under reduced pressure. The resulting dried film was dissolved in methanol. A solution of docetaxel in methanol and the solution of compound I-1a in methanol was mixed. After stirring the organic solvent was evaporated. The resulting dried film was dissolved in saline.

From this initial solution the working solutions in medium with 5% FBS for adding to cultures were prepared. Cultures of DU 145 cells were treated with drug solutions on day 1 after seeding. Aliquots of working solutions (2 μL) with different concentrations of formulation were added to 200 μL cultures to a final concentration of docetaxel $1 \times 10^{-9}$, $1 \times 10^{-8}$ and $1 \times 10^{-7}$ mol/L in the cultures. In the control cultures, 2 μL of medium with 5% FBS was added as solvent control. After cultivation for two consecutive days, the number of viable cells in cultures was counted in order to evaluate the cytotoxicity of the tested solutions of the formulation (Table 2).

TABLE 2

Evaluation of the cytotoxicity of the formulation docetaxel/compound I-1a in cultures of human prostate carcinoma DU 145 cell line at molar ratio docetaxel:compound I-1a (1:6) related to the final concentration of docetaxel/compound I-1a in cultures

| Drug | Formulation | | Tumor Cell Number, × $10^3$ | Cell growth Inhibition, % | Positive Effect, % | $IC_{50}$ mol/L (a) |
|---|---|---|---|---|---|---|
| | Docetaxel, mol/L | Compound I-1a, mol/L | | | | |
| Control | 0 | 0 | 41.5 ± 2.93 | — | — | — |
| Docetaxel | $10^{-9}$ | 0 | 27.1 ± 1.07 | 34.7* | — | $8.0 \times 10^{-9}$ |
| | $10^{-8}$ | 0 | 20.0 ± 1.16 | 51.8* | — | |
| | $10^{-7}$ | 0 | 10.8 ± 0.94 | 74.0* | — | |
| Formulation | $10^{-9}$ | $6 \times 10^{-9}$ | 22.2 ± 0.88 | 46.5* | +18.1** | $1.5 \times 10^{-9}$ |
| | $10^{-8}$ | $6 \times 10^{-8}$ | 14.8 ± 1.11 | 64.3* | +26.0** | |
| | $10^{-7}$ | $6 \times 10^{-7}$ | 5.9 ± 0.45 | 85.8* | +45.4* | |

(a) Cell growth inhibition data, determined at three different concentrations, were used to calculate the drug concentrations that inhibited cell growth by 50% as compared to untreated control cultures. All data are the means of three determinations each in six replicates.
*p < 0.001
**p < 0.01

Example 18

Evaluation of the Cytotoxicity of the Formulation Docetaxel/Compound I-1b in Cultures of Human Ovary Adenocarcinoma SKOV-3 Cell Line Related to Molar Ratios Docetaxel:Compound I-1b An aliquot of a stock solution of the sodium salt of compound I-1b (2 mg) in ethanol-water (2:1, v/v) was evaporated on a rotary evaporator under reduced pressure. The resulting dried film was dissolved in methanol. A solution of docetaxel in methanol and the solution of compound I-1b in methanol was mixed. After stirring the organic solvent was evaporated. The resulting dried film was dissolved in saline.

Initial solutions of the formulation in saline at the molar ratios docetaxel:compound I-1b equal to 1:3, 1:6 and 1:10 were prepared. From these solutions the working solutions in medium with 5% FBS for adding to cultures were prepared. Concentration of docetaxel was equal to $10^{-5}$ M.

Cultures of SKOV-3 cells were treated with drug solutions on day 1 after seeding. Aliquots of the working solutions (2 µL) were added to 200 µL cultures to a final concentration of docetaxel in cultures equal to $10^{-7}$ M.

In the control cultures, 2 µL of medium with 5% FBS was added as solvent control. After cultivation for two consecutive days, the number of viable cells in cultures was counted in order to evaluate the cytotoxicity of the tested solutions of the formulation.

After three days of cultivation, the control cultures contained (51.5±2.84)×$10^3$ cells.

The cultures, treated by docetaxel in a concentration of 100 nM, contained (16.1±0.94)×$10^3$ cells, cell growth inhibition was 68.7% (p<0.001).

The cultures of SKOV-3 cells, treated by solutions of the formulation at the molar ratio docetaxel/compound I-1b equal to 1:3, 1:6, and 1:10 in medium with 5% FBS, had the following number of viable cells:

1:3: (9.2±0.82)×$10^3$, cell growth inhibition was 82.1% (p<0.001), cell growth inhibition compared to that of docetaxel was increased by 42.9% (p<0.001);

1:6: (8.4±0.75)×$10^3$, cell growth inhibition was 83.7% (p<0.001), cell growth inhibition compared to that of docetaxel was increased by 47.8% (p<0.001);

1:10: (7.6±0.69)×$10^3$, cell growth inhibition was 85.2% (p<0.001), cell growth inhibition compared to that of docetaxel was increased by 52.8% (p<0.001).

Example 19

Evaluation of the Cytotoxicity of the Formulation Docetaxel/Compound I-1b in Cultures of Human Ovary Adenocarcinoma SKOV-3 Cell Line at Molar Ratio Docetaxel:Compound I-1b (1:6) Related to the Final Concentration of Docetaxel/Compound I-1b in Cultures An aliquot of a stock solution of the sodium salt of compound I-1b (2 mg) in ethanol-water (2:1, v/v) was evaporated on a rotary evaporator under reduced pressure. The resulting dried film was dissolved in methanol. A solution of docetaxel in methanol and the solution of compound I-1b in methanol was mixed. After stirring the organic solvent was evaporated. The resulting dried film was dissolved in saline.

From this initial solution the working solutions in medium with 5% FBS for adding to cultures were prepared. Cultures of SKOV-3 cells were treated with drug solutions on day 1 after seeding. Aliquots of working solutions (2 µL) with different concentrations of formulation were added to 200 µL cultures to a final concentration of docetaxel 1×$10^{-9}$, 1×$10^{-8}$ and 1×$10^{-7}$ mol/L in the cultures.

In the control cultures, 2 µL of medium with 5% FBS was added as solvent control. After cultivation for two consecutive days, the number of viable cells in cultures was counted in order to evaluate the cytotoxicity of the tested solutions of the formulation (Table 3).

TABLE 3

Evaluation of the cytotoxicity of the formulation docetaxel/compound I-1b in cultures of human ovary adenocarcinoma SKOV-3 cell line at molar ratio docetaxel:compound I-1b (1:6) related to the final concentration of docetaxel/compound I-1b in cultures

| Drug | Formulation | | Tumor Cell Number, × $10^3$ | Cell growth Inhibition, % | Positive Effect, % | $IC_{50}$ mol/L (a) |
|---|---|---|---|---|---|---|
| | Docetaxel, mol/L | Compound I-1b, mol/L | | | | |
| Control | 0 | 0 | 52.1 ± 2.96 | — | — | — |
| Docetaxel | $10^{-9}$ | 0 | 34.3 ± 2.01 | 34.2* | — | $5.2 \times 10^{-9}$ |
| | $10^{-8}$ | 0 | 23.2 ± 2.19 | 55.5* | — | |
| | $10^{-7}$ | 0 | 16.8 ± 0.80 | 67.8* | — | |
| Formulation | $10^{-9}$ | $6 \times 10^{-9}$ | 26.5 ± 1.29 | 49.1* | +22.7** | $1.2 \times 10^{-9}$ |
| | $10^{-8}$ | $6 \times 10^{-8}$ | 15.3 ± 0.85 | 70.6* | +34.1** | |
| | $10^{-7}$ | $6 \times 10^{-7}$ | 8.7 ± 0.80 | 83.3* | +48.2* | |

(a) Cell growth inhibition data, determined at three different concentrations, were used to calculate the drug concentrations that inhibited cell growth by 50% as compared to untreated control cultures. All data are the means of three determinations each in six replicates.
*p < 0.001
**p < 0.01

Example 20

Evaluation of the Cytotoxicity of the Formulation Docetaxel/Compound I-1c in Cultures of Human Lung Carcinoma A549 Cell Line Related to Molar Ratios Docetaxel:Compound I-1c An aliquot of a stock solution of the sodium salt of compound I-1c (2 mg) in ethanol-water (2:1, v/v) was evaporated on a rotary evaporator under reduced pressure. The resulting dried film was dissolved in methanol. A solution of docetaxel in methanol and the solution of compound I-1c in methanol was mixed. After stirring the organic solvent was evaporated. The resulting dried film was dissolved in saline.

Initial solutions of the formulation in saline at the molar ratios docetaxel:compound I-1c equal to 1:3, 1:6 and 1:10 were prepared. From these solutions the working solutions in medium with 5% FBS for adding to cultures were prepared. Concentration of docetaxel was equal to $10^{-5}$ M.

Cultures of A549 cells were treated with drug solutions on day 1 after seeding. Aliquots of the working solutions (2 μL) were added to 200 μL cultures to a final concentration of docetaxel in cultures equal to $10^{-7}$ M. In control cultures 2 μL of medium with 5% FBS was added as solvent control. After cultivation for two consecutive days, the number of viable cells in cultures was counted in order to evaluate the cytotoxicity of the tested solutions of the formulation.

After three days of cultivation, the control cultures contained (53.7±2.59)×$10^3$ cells.

The cultures, treated by docetaxel in a concentration of 100 nM, contained (10.6±0.72)×$10^3$ cells, cell growth inhibition was 80.3% (p<0.001).

The cultures of A549 cells, treated by solutions of the formulation at the molar ratio docetaxel/compound I-1c equal to 1:3, 1:6, and 1:10 in medium with 5% FBS, had the following number of viable cells:

1:3: (7.0±0.53)×$10^3$, cell growth inhibition was 87.0% (p<0.001), cell growth inhibition compared to that of docetaxel was increased by 34.0% (p<0.002);

1:6: (6.6±0.58)×$10^3$, cell growth inhibition was 87.7% (p<0.001), cell growth inhibition compared to that of docetaxel was increased by 37.7% (p<0.002);

1:10: (6.3 1 0.42)×$10^3$, cell growth inhibition was 88.3% (p<0.001), cell growth inhibition compared to that of docetaxel was increased by 40.6% (p<0.001).

Example 21

Evaluation of the Cytotoxicity of the Formulation Docetaxel/Compound I-1c in Cultures of Human Lung Carcinoma A549 Cell Line at Molar Ratio Docetaxel:Compound I-1c (1:6) Related to the Final Concentration of Docetaxel/Compound I-1c in Cultures An aliquot of a stock solution of the sodium salt of compound I-1c (2 mg) in ethanol-water (2:1, v/v) was evaporated on a rotary evaporator under reduced pressure. The resulting dried film was dissolved in methanol. A solution of docetaxel in methanol and the solution of compound I-1c in methanol was mixed. After stirring the organic solvent was evaporated. The resulting dried film was dissolved in saline.

From this initial solution the working solutions in medium with 5% FBS for adding to cultures were prepared. Cultures of A549 cells were treated with drug solutions on day 1 after seeding. Aliquots of working solutions (2 μL) with different concentrations of formulation were added to 200 μL cultures to a final concentration of docetaxel $1\times10^{-9}$, $1\times10^{-8}$ and $1\times^{-7}$ mol/L in the cultures.

In the control cultures, 2 μL of medium with 5% FBS was added as solvent control. After cultivation for two consecutive days, the number of viable cells in cultures was counted in order to evaluate the cytotoxicity of the tested solutions of the formulation (Table 4).

TABLE 4

Evaluation of the cytotoxicity of the formulation docetaxel/compound I-1c in cultures of human lung carcinoma A549 cell line at molar ratio docetaxel: compound I-1c (1:6) related to the final concentration of docetaxel/compound I-1c in cultures

| Drug | Formulation Docetaxel, mol/L | Compound I-1c, mol/L | Tumor Cell Number, × $10^3$ | Cell growth Inhibition, % | Positive Effect, % | $IC_{50}$ mol/L (a) |
|---|---|---|---|---|---|---|
| Control | 0 | 0 | 54.6 ± 2.79 | — | — | — |
| Docetaxel | $10^{-9}$ | 0 | 34.1 ± 2.07 | 37.5* | — | $2.2 \times 10^{-9}$ |
|  | $10^{-8}$ | 0 | 15.6 ± 0.49 | 71.4* | — |  |
|  | $10^{-7}$ | 0 | 10.5 ± 0.97 | 80.8* | — |  |
| Formulation | $10^{-9}$ | $6 \times 10^{-9}$ | 27.4 ± 1.83 | 49.8* | +19.6• | $1.0 \times 10^{-9}$ |
|  | $10^{-8}$ | $6 \times 10^{-8}$ | 9.7 ± 0.46 | 82.2* | +37.8* |  |
|  | $10^{-7}$ | $6 \times 10^{-7}$ | 6.5 ± 0.43 | 88.1* | +38.1** |  | a) Cell growth inhibition data, determined at three different concentrations, were used to calculate the drug concentrations that inhibited cell growth by 50% as compared to untreated control cultures. All data are the means of three determinations each in six replicates.
*p < 0.001
**p < 0.01
•p < 0.05

Example 22

Evaluation of the Cytotoxicity of the Formulation Docetaxel/Compound II-1 in Cultures of Human Breast Adenocarcinoma MDA-MB-231 Cell Line, Related to Molar Ratios Docetaxel:Compound II-1

The sodium salt of compound II-1 was converted into acidic form of compound II-1 and dissolved in methanol. A solution of docetaxel in methanol and the solution of compound II-1 in methanol was mixed. After stirring the organic solvent was evaporated. The resulting dried film was dissolved in saline.

Initial solutions of the formulation in saline at the molar ratios docetaxel:compound II-1 equal to 1:3, 1:6 and 1:10 were prepared. From these solutions the working solutions in medium with 5% FBS for adding to cultures were prepared. Concentration of docetaxel was equal to $10^{-5}$ M.

Cultures of MDA-MB-231 cells were treated with drug solutions on day 1 after seeding. Aliquots of the working solutions (2 μL) were added to 200 μL cultures to a final concentration of docetaxel in cultures equal to $10^{-7}$ M. In control cultures 2 μL of medium with 5% FBS was added as solvent control. After cultivation for two consecutive days, the number of viable cells in cultures was counted in order to evaluate the cytotoxicity of the tested solutions of the formulation.

After three days of cultivation, the control cultures contained (57.6±3.04)×$10^3$ cells.

The cultures, treated by docetaxel in a concentration of 100 nM, contained (15.4±1.02)×$10^3$ cells, cell growth inhibition was 73.3% (p<0.001).

The cultures of MDA-MB-231 cells, treated by solutions of the formulation at the molar ratio docetaxel/compound II-1 equal to 1:3, 1:6 and 1:10 in medium with 5% FBS, had the following number of viable cells:

1:3: (9.5±0.62)×$10^3$, cell growth inhibition was 83.5% (p<0.001), cell growth inhibition compared to that of docetaxel was increased by 38.3% (p<0.001);

1:6: (8.6±0.57)×$10^3$, cell growth inhibition was 85.1% (p<0.001), cell growth inhibition compared to that of docetaxel was increased by 44.2% (p<0.001);

1:10: (8.1±0.59)×$10^3$, cell growth inhibition was 85.9% (p<0.001), cell growth inhibition compared to that of docetaxel was increased by 47.4% (p<0.001).

Example 23

Evaluation of the Cytotoxicity of the Formulation Docetaxel/Compound II-1 in Cultures of Human Breast Adenocarcinoma MDA-MB-231 Cell Line at Molar Ratio Docetaxel:Compound II-1 (1:6) Related to the Final Concentration of Docetaxel/Compound II-1 in Cultures The sodium salt of compound II-1 was converted into the acidic form of compound II-1 and dissolved in methanol. A solution of docetaxel in methanol and the solution of compound II-1 in methanol was mixed. After stirring the organic solvent was evaporated. The resulting dried film was dissolved in saline.

From this initial solution the working solutions in medium with 5% FBS for adding to cultures were prepared. Cultures of MDA-MB-231 cells were treated with drug solutions on day 1 after seeding. Aliquots of working solutions (2 μL) with different concentrations of formulation were added to 200 μL cultures to a final concentration of docetaxel 1×$10^{-9}$, 1×$10^{-8}$ and 1×$10^{-7}$ mol/L in the cultures.

In the control cultures, 2 μL of medium with 5% FBS was added as solvent control. After cultivation for two consecutive days, the number of viable cells in cultures was counted in order to evaluate the cytotoxicity of the tested solutions of the formulation (Table 5).

TABLE 5

Evaluation of the cytotoxicity of the formulation docetaxel/compound II-1 in cultures of human breast adenocarcinoma MDA-MB-231 cell line at molar ratio docetaxel:compound II-1 (1:6) related to the final concentration of docetaxel/compound II-1 in cultures

| Drug | Formulation | | Tumor Cell Number, $\times 10^3$ | Cell growth Inhibition, % | Positive Effect, % | $IC_{50}$ mol/L (a) |
| --- | --- | --- | --- | --- | --- | --- |
| | Docetaxel, mol/L | Compound II-1, mol/L | | | | |
| Negative Control | 0 | 0 | 55.8 ± 1.99 | — | — | — |
| Docetaxel | $10^{-9}$ | 0 | 34.2 ± 2.28 | 38.7* | — | $3.6 \times 10^{-9}$ |
| | $10^{-8}$ | 0 | 23.4 ± 2.15 | 58.1* | — | |
| | $10^{-7}$ | 0 | 13.7 ± 1.03 | 75.4* | — | |
| Formulation | $10^{-9}$ | $6 \times 10^{-9}$ | 26.3 ± 1.49 | 52.9* | +23.1• | $7.0 \times 10^{-10}$ (b) |
| | $10^{-8}$ | $6 \times 10^{-8}$ | 15.6 ± 1.22 | 72.0* | +33.3** | |
| | $10^{-7}$ | $6 \times 10^{-7}$ | 7.7 ± 0.64 | 86.2* | +43.8* | |

(a) Cell growth inhibition data, determined at three different concentrations, were used to calculate the drug concentrations that inhibited cell growth by 50% as compared to untreated control cultures. All data are the means of three determinations each in six replicates.
(b) Extrapolated.
*p < 0.001
**p < 0.01
•p < 0.02

Example 24

Evaluation of the Cytotoxicity of the Formulation Docetaxel/Compound II-1a in Cultures of Human Prostate Carcinoma DU 145 Cell Line Related to Molar Ratios Docetaxel:Compound II-1a An aliquot of a stock solution of the sodium salt of compound II-1a (2 mg) in ethanol-water (2:1, v/v) was evaporated on a rotary evaporator under reduced pressure. The resulting dried film was dissolved in methanol. A solution of docetaxel in methanol and the solution of compound II-1a in methanol was mixed. After stirring the organic solvent was evaporated. The resulting dried film was dissolved in saline.

Initial solutions of the formulation in saline at the molar ratios docetaxel:compound II-1a equal to 1:3, 1:6 and 1:10 were prepared. From these solutions the working solutions in medium with 5% FBS for adding to cultures were prepared. Concentration of docetaxel was equal to $10^{-5}$ M.

Cultures of DU 145 cells were treated with drug solutions on day 1 after seeding. Aliquots of the working solutions (2 µL) were added to 200 µL cultures to a final concentration of docetaxel in cultures equal to $10^{-7}$ M. In control cultures 2 µL of medium with 5% FBS was added as solvent control. After cultivation for two consecutive days, the number of viable cells in cultures was counted in order to evaluate the cytotoxicity of the tested solutions of the formulation.

After three days of cultivation, the control cultures contained (55.7±2.69)×10³ cells.

The cultures, treated by docetaxel in a concentration of 100 nM, contained (14.2±0.85)×10³ cells, cell growth inhibition was 74.5% (p<0.001).

The cultures of DU 145 cells, treated by solutions of the formulation at the molar ratio docetaxel/compound II-1a equal to 1:3, 1:6, and 1:10 in medium with 5% FBS, had the following number of viable cells:

1:3: (7.9±0.73)×10³, cell growth inhibition was 85.8% (p<0.001), cell growth inhibition compared to that of docetaxel was increased by 44.4% (p<0.001);

1:6: (7.5±0.59)×10³, cell growth inhibition was 86.5% (p<0.001), cell growth inhibition compared to that of docetaxel was increased by 47.2% (p<0.001);

1:10: (6.8±0.58)×10³, cell growth inhibition was 87.8% (p<0.001), cell growth inhibition compared to that of docetaxel was increased by 52.1% (p<0.001).

Example 25

Evaluation of the Cytotoxicity of the Formulation Docetaxel/Compound II-1a in Cultures of Human Prostate Carcinoma DU 145 Cell Line at Molar Ratio Docetaxel:Compound II-1a (1:6) Related to the Final Concentration of Docetaxel/Compound II-1a in Cultures An aliquot of a stock solution of the sodium salt of compound II-1a (2 mg) in ethanol-water (2:1, v/v) was evaporated on a rotary evaporator under reduced pressure. The resulting dried film was dissolved in methanol. A solution of docetaxel in methanol and the solution of compound II-1a in methanol was mixed. After stirring the organic solvent was evaporated. The resulting dried film was dissolved in saline.

From this initial solution the working solutions in medium with 5% FBS for adding to cultures were prepared. Cultures of DU 145 cells were treated with drug solutions on day 1 after seeding. Aliquots of working solutions (2 µL) with different concentrations of formulation were added to 200 µL cultures to a final concentration of docetaxel $1\times10^{-9}$, $1\times10^{-8}$ and $1\times10^{-7}$ mol/L in the cultures. In control cultures 2 µL of medium with 5% FBS was added as solvent control. After cultivation for two consecutive days, the number of viable cells in cultures was counted in order to evaluate the cytotoxicity of the tested solutions of the formulation (Table 6).

TABLE 6

Evaluation of the cytotoxicity of the formulation docetaxel/compound II-1a in cultures of human prostate carcinoma DU 145 cell line at molar ratio docetaxel:compound II-1a (1:6) related to the final concentration of docetaxel/compound II-1a in cultures

| Drug | Formulation | | Tumor Cell Number, × $10^3$ | Cell growth Inhibition, % | Positive Effect, % | $IC_{50}$ mol/L (a) |
|---|---|---|---|---|---|---|
| | Docetaxel, mol/L | Compound II-1a, mol/L | | | | |
| Control | 0 | 0 | 41.5 ± 2.93 | — | — | — |
| Docetaxel | $10^{-9}$ | 0 | 27.1 ± 1.07 | 34.7* | — | $8.0 \times 10^{-9}$ |
| | $10^{-8}$ | 0 | 20.0 ± 1.16 | 51.8* | — | |
| | $10^{-7}$ | 0 | 10.8 ± 0.94 | 74.0* | — | |
| Formulation | $10^{-9}$ | $6 \times 10^{-9}$ | 23.1 ± 1.52 | 44.3* | +14.8•• | $2.2 \times 10^{-9}$ |
| | $10^{-8}$ | $6 \times 10^{-8}$ | 15.8 ± 1.27 | 61.9* | +21.0• | |
| | $10^{-7}$ | $6 \times 10^{-7}$ | 6.4 ± 0.54 | 84.6* | +40.7** | |

(a) Cell growth inhibition data, determined at three different concentrations, were used to calculate the drug concentrations that inhibited cell growth by 50% as compared to untreated control cultures. All data are the means of three determinations each in six replicates.
*p < 0.001
**p < 0.002
•p < 0.5
••p > 0.05

Example 26

Evaluation of the Cytotoxicity of the Formulation Docetaxel/Compound II-1b in Cultures of Human Ovary Adenocarcinoma SKOV-3 Cell Line Related to Molar Ratios Docetaxel:Compound II-1b An aliquot of a stock solution of the sodium salt of compound II-1b (2 mg) in ethanol-water (2:1, v/v) was evaporated on a rotary evaporator under reduced pressure. The resulting dried film was dissolved in methanol. A solution of docetaxel in methanol and the solution of compound II-1b in methanol was mixed. After stirring the organic solvent was evaporated. The resulting dried film was dissolved in saline.

Initial solutions of the formulation in saline at the molar ratios docetaxel:compound II-1b equal to 1:3, 1:6 and 1:10 were prepared. From these solutions the working solutions in medium with 5% FBS for adding to cultures were prepared. Concentration of docetaxel was equal to $10^{-5}$ M.

Cultures of SKOV-3 cells were treated with drug solutions on day 1 after seeding. Aliquots of the working solutions (2 μL) were added to 200 μL cultures to a final concentration of docetaxel in cultures equal to $10^{-7}$ M. In control cultures 2 μL of medium with 5% FBS was added as solvent control. After cultivation for two consecutive days, the number of viable cells in cultures was counted in order to evaluate the cytotoxicity of the tested solutions of the formulation.

After three days of cultivation, the control cultures contained (51.5±2.84)×$10^3$ cells.

The cultures, treated by docetaxel in a concentration of 100 nM, contained (16.1±0.94)×$10^3$ cells, cell growth inhibition was 68.7% (p<0.001).

The cultures of SKOV-3 cells, treated by solutions of the formulation at the molar ratio docetaxel/compound II-1b equal to 1:3, 1:6, and 1:10 in medium with 5% FBS, had the following number of viable cells:

1:3: (9.6±0.86)×$10^3$, cell growth inhibition was 81.4% (p<0.001), cell growth inhibition compared to that of docetaxel was increased by 40.4% (p<0.001);

1:6: (8.8±0.72)×$10^3$, cell growth inhibition was 82.9% (p<0.001), cell growth inhibition compared to that of docetaxel was increased by 45.3% (p<0.001);

1:10: (8.1±0.70)×$10^3$, cell growth inhibition was 84.3% (p<0.001), cell growth inhibition compared to that of docetaxel was increased by 49.7% (p<0.001).

Example 27

Evaluation of the Cytotoxicity of the Formulation Docetaxel/Compound II-1b in Cultures of Human Ovary Adenocarcinoma SKOV-3 Cell Line at Molar Ratio Docetaxel:Compound II-1b (1:6) Related to the Final Concentration of Docetaxel/Compound II-1b in Cultures An aliquot of a stock solution of the sodium salt of compound II-1b (2 mg) in ethanol-water (2:1, v/v) was evaporated on a rotary evaporator under reduced pressure. The resulting dried film was dissolved in methanol. A solution of docetaxel in methanol and the solution of compound II-1b in methanol was mixed. After stirring the organic solvent was evaporated. The resulting dried film was dissolved in saline.

From this initial solution the working solutions in medium with 5% FBS for adding to cultures were prepared. Cultures of SKOV-3 cells were treated with drug solutions on day 1 after seeding. Aliquots of working solutions (2 μL) with different concentrations of formulation were added to 200 μL cultures to a final concentration of docetaxel 1×$10^{-9}$, 1×$10^{-8}$ and 1×$10^{-7}$ mol/L in the cultures.

In the control cultures, 2 μL of medium with 5% FBS was added as solvent control. After cultivation for two consecutive days, the number of viable cells in cultures was counted in order to evaluate the cytotoxicity of the tested solutions of the formulation (Table 7).

TABLE 7

Evaluation of the cytotoxicity of the formulation docetaxel/compound II-1b in cultures of human ovary adenocarcinoma SKOV-3 cell line at molar ratio docetaxel: compound II-1b (1:6) related to the final concentration of docetaxel/compound II-1b in cultures

| Drug | Formulation | | Tumor Cell Number, × 10³ | Cell growth Inhibition, % | Positive Effect, % | IC$_{50}$ mol/L (a) |
|---|---|---|---|---|---|---|
| | Docetaxel, mol/L | Compound II-1b, mol/L | | | | |
| Control | 0 | 0 | 52.1 ± 2.96 | — | — | — |
| Docetaxel | $10^{-9}$ | 0 | 34.3 ± 2.01 | 34.2* | — | $5.2 \times 10^{-9}$ |
| | $10^{-8}$ | 0 | 23.2 ± 2.19 | 55.5* | — | |
| | $10^{-7}$ | 0 | 16.8 ± 0.80 | 67.8* | — | |
| Formulation | $10^{-9}$ | $6 \times 10^{-9}$ | 27.4 ± 1.36 | 47.4* | +20.1** | $1.3 \times 10^{-9}$ |
| | $10^{-8}$ | $6 \times 10^{-8}$ | 15.9 ± 1.04 | 69.5* | +31.5** | |
| | $10^{-7}$ | $6 \times 10^{-7}$ | 9.2 ± 0.68 | 82.3* | +45.2* | |

(a) Cell growth inhibition data, determined at three different concentrations, were used to calculate the drug concentrations that inhibited cell growth by 50% as compared to untreated control cultures. All data are the means of three determinations each in six replicates.
*p < 0.001
**p < 0.02

Example 28

Evaluation of the Cytotoxicity of the Formulation Docetaxel/Compound II-1c in Cultures of Human Lung Carcinoma A549 Cell Line Related to Molar Ratios Docetaxel:Compound II-1c An aliquot of a stock solution of the sodium salt of compound II-1c (2 mg) in ethanol-water (2:1, v/v) was evaporated on a rotary evaporator under reduced pressure. The resulting dried film was dissolved in methanol. A solution of docetaxel in methanol and the solution of compound II-1c in methanol was mixed. After stirring the organic solvent was evaporated. The resulting dried film was dissolved in saline.

Initial solutions of the formulation in saline at the molar ratios docetaxel:compound II-1c equal to 1:3, 1:6 and 1:10 were prepared. From these solutions the working solutions in medium with 5% FBS for adding to cultures were prepared. The concentration of docetaxel was equal to $10^{-5}$ M.

Cultures of A549 cells were treated with drug solutions on day 1 after seeding. Aliquots of the working solutions (2 μL) were added to 200 μL cultures to a final concentration of docetaxel in cultures equal to $10^{-7}$ M. In control cultures 2 μL of medium with 5% FBS was added as solvent control. After cultivation for two consecutive days, the number of viable cells in cultures was counted in order to evaluate the cytotoxicity of the tested solutions of the formulation.

After three days of cultivation the control cultures contained $(53.7\pm2.59)\times10^3$ cells.

The cultures, treated by docetaxel in a concentration of 100 nM, contained $(10.6\pm0.72)\times10^3$ cells, cell growth inhibition was 80.3% (p<0.001).

The cultures of A549 cells, treated by solutions of the formulation at the molar ratio docetaxel/compound II-1c equal to 1:3, 1:6, and 1:10 in medium with 5% FBS, had the following number of viable cells:

1:3: $(7.2\pm0.61)\times10^3$, cell growth inhibition was 86.6% (p<0.001), cell growth inhibition compared to that of docetaxel was increased by 32.1% (p<0.01);

1:6: $(6.8\pm0.52)\times10^3$, cell growth inhibition was 87.3% (p<0.001), cell growth inhibition compared to that of docetaxel was increased by 35.8% (p<0.002);

1:10: $(6.5\pm0.50)\times10^3$, cell growth inhibition was 87.9% (p<0.001), cell growth inhibition compared to that of docetaxel was increased by 38.7% (p<0.001).

Example 29

Evaluation of the Cytotoxicity of the Formulation Docetaxel/Compound II-1c in Cultures of Human Lung Carcinoma A549 Cell Line at Molar Ratio Docetaxel:Compound II-1c (1:6) Related to the Final Concentration of Docetaxel/Compound II-1c in Cultures An aliquot of a stock solution of the sodium salt of compound II-1c (2 mg) in ethanol-water (2:1, v/v) was evaporated on a rotary evaporator under reduced pressure. The resulting dried film was dissolved in methanol. A solution of docetaxel in methanol and the solution of compound II-1c in methanol was mixed. After stirring the organic solvent was evaporated. The resulting dried film was dissolved in saline.

From this initial solution the working solutions in medium with 5% FBS for adding to cultures were prepared. Cultures of A549 cells were treated with drug solutions on day 1 after seeding. Aliquots of working solutions (2 μL) with different concentrations of formulation were added to 200 μL cultures to a final concentration of docetaxel $1\times10^{-9}$, $1\times10^{-8}$ and $1\times10^{-7}$ mol/L in the cultures.

In control cultures 2 μL of medium with 5% FBS was added as solvent control. After cultivation for two consecutive days, the number of viable cells in cultures was counted in order to evaluate the cytotoxicity of the tested solutions of the formulation (Table 8).

TABLE 8

Evaluation of the cytotoxicity of the formulation docetaxel/compound II-1c in cultures of human lung carcinoma A549 cell line at molar ratio docetaxel: compound II-1c (1:6) related to the final concentration of docetaxel/compound II-1c in cultures

| Drug | Formulation Docetaxel, mol/L | Compound II-1c, mol/L | Tumor Cell Number, × 10³ | Cell growth Inhibition, % | Positive Effect, % | IC$_{50}$ mol/L (a) |
|---|---|---|---|---|---|---|
| Control | 0 | 0 | 54.6 ± 2.79 | — | — | — |
| Docetaxel | $10^{-9}$ | 0 | 34.1 ± 2.07 | 37.5* | — | $2.2 \times 10^{-9}$ |
|  | $10^{-8}$ | 0 | 15.6 ± 0.49 | 71.4* | — |  |
|  | $10^{-7}$ | 0 | 10.5 ± 0.97 | 80.8* | — |  |
| Formulation | $10^{-9}$ | $6 \times 10^{-9}$ | 28.6 ± 1.39 | 47.6* | +16.1• | $1.2 \times 10^{-9}$ |
|  | $10^{-8}$ | $6 \times 10^{-8}$ | 10.4 ± 0.75 | 81.0* | +33.3* |  |
|  | $10^{-7}$ | $6 \times 10^{-7}$ | 6.9 ± 0.52 | 87.4* | +34.3** |  |

(a) Cell growth inhibition data, determined at three different concentrations, were used to calculate the drug concentrations that inhibited cell growth by 50% as compared to untreated control cultures. All data are the means of three determinations each in six replicates.

*p < 0.001
**p < 0.01
•p < 0.05

Example 30

Evaluation of the Cytotoxicity of the Formulation Paclitaxel/Compound II-1 in Cultures of Human Ovary Adenocarcinoma SKOV-3 Cell Line, Related to Molar Ratios Paclitaxel:Compound II-1

The sodium salt of compound II-1 was converted into the acidic form of compound II-1 and dissolved in methanol. A solution of paclitaxel in methanol and the solution of compound II-1 in methanol was mixed. After stirring the organic solvent was evaporated. The resulting dried film was dissolved in saline.

Initial solutions of the formulation in saline at the molar ratios paclitaxel:compound II-1 equal to 1:3, 1:6 and 1:10 were prepared. From these solutions the working solutions in medium with 5% FBS for adding to cultures were prepared. The concentration of paclitaxel was equal to $10^{-5}$ M.

Cultures of SKOV-3 cells were treated with drug solutions on day 1 after seeding. Aliquots of the working solutions (2 µL) were added to 200 µL cultures to a final concentration of paclitaxel in cultures equal to $10^{-7}$ M. In control cultures 2 µL of medium with 5% FBS was added as solvent control. After cultivation for two consecutive days, the number of viable cells in cultures was counted in order to evaluate the cytotoxicity of the tested solutions of the formulation.

After three days of cultivation the control cultures contained (50.5±2.58)×10³ cells.

The cultures, treated by paclitaxel in a concentration of 100 nM, contained (14.6±0.82)×10³ cells, cell growth inhibition was 71.1% (p<0.001).

The cultures of SKOV-3 cells, treated by solutions of the formulation at the molar ratio paclitaxel/compound II-1 equal to 1:3, 1:6, and 1:10 in medium with 5% FBS, had the following number of viable cells:

1:3: (9.6±0.68)×10³, cell growth inhibition was 81.0% (p<0.001), cell growth inhibition compared to that of paclitaxel was increased by 34.2% (p<0.001);

1:6: (8.7±0.63)×10³, cell growth inhibition was 82.8% (p<0.001), cell growth inhibition compared to that of paclitaxel was increased by 40.4% (p<0.001);

1:10: (8.2±0.70)×10³, cell growth inhibition was 83.8% (p<0.001), cell growth inhibition compared to that of paclitaxel was increased by 43.8% (p<0.001).

Example 31

Evaluation of the Cytotoxicity of the Formulation Paclitaxel/Compound II-1 in Cultures of Human Ovary Adenocarcinoma SKOV-3 Cell Line at Molar Ratio Paclitaxel:Compound II-1 (1:6) Related to the Final Concentration of Paclitaxel/Compound II-1 in Cultures The sodium salt of compound II-1 was converted into the acidic form of compound II-1 and dissolved in methanol. A solution of paclitaxel in methanol and the solution of compound II-1 in methanol was mixed. After stirring the organic solvent was evaporated. The resulting dried film was dissolved in saline.

From this initial solution the working solutions in medium with 5% FBS for adding to cultures were prepared. Cultures of SKOV-3 cells were treated with drug solutions on day 1 after seeding. Aliquots of working solutions (2 µL) with different concentrations of formulation were added to 200 µL cultures to a final concentration of paclitaxel $1 \times 10^{-9}$, $1 \times 10^{-8}$ and $1 \times 10^{-7}$ mol/L in the cultures.

In the control cultures, 2 µL of medium with 5% FBS was added as solvent control. After cultivation for two consecutive days, the number of viable cells in cultures was counted in order to evaluate the cytotoxicity of the tested solutions of the formulation (Table 9).

TABLE 9

Evaluation of the cytotoxicity of the formulation paclitaxel/compound II-1 in cultures of human ovary adenocarcinoma SKOV-3 cell line at molar ratio paclitaxel: compound II-1 (1:6) related to the final concentration of paclitaxel/compound II-1 in cultures

| Drug | Formulation | | Tumor Cell Number, × $10^3$ | Cell growth Inhibition, % | Positive Effect, % | $IC_{50}$ mol/L (a) |
|---|---|---|---|---|---|---|
| | Paclitaxel, mol/L | Compound II-1, mol/L | | | | |
| Control | 0 | 0 | 49.6 ± 3.13 | — | — | — |
| Paclitaxel | $10^{-9}$ | 0 | 37.3 ± 1.80 | 24.8** | — | $4.5 \times 10^{-9}$ |
| | $10^{-8}$ | 0 | 19.9 ± 1.45 | 59.9* | — | |
| | $10^{-7}$ | 0 | 14.1 ± 0.98 | 71.6* | — | |
| Formulation | $10^{-9}$ | $6 \times 10^{-9}$ | 27.6 ± 1.56 | 44.4* | +26.0• | $1.4 \times 10^{-9}$ |
| | $10^{-8}$ | $6 \times 10^{-8}$ | 13.3 ± 0.71 | 73.2* | +33.2• | |
| | $10^{-7}$ | $6 \times 10^{-7}$ | 8.3 ± 0.57 | 83.3* | +41.1* | |

(a) Cell growth inhibition data, determined at three different concentrations, were used to calculate the drug concentrations that inhibited cell growth by 50% as compared to untreated control cultures. All data are the means of three determinations each in six replicates.
*p < 0.001
**p < 0.01
•p < 0.002

Example 32

Evaluation of the Cytotoxicity of the Formulation Paclitaxel/Compound II-1a in Cultures of Human Ovary Adenocarcinoma SKOV-3 Cell Line Related to Molar Ratios Paclitaxel:Compound II-1a An aliquot of a stock solution of the sodium salt of compound II-1a (2 mg) in ethanol-water (2:1, v/v) was evaporated on a rotary evaporator under reduced pressure. The resulting dried film was dissolved in methanol. A solution of paclitaxel in methanol and the solution of compound II-1a in methanol was mixed. After stirring the organic solvent was evaporated. The resulting dried film was dissolved in saline.

Initial solutions of the formulation in saline at the molar ratios paclitaxel:compound II-1a equal to 1:3, 1:6 and 1:10 were prepared. From these solutions the working solutions in medium with 5% FBS for adding to cultures were prepared. The concentration of paclitaxel was equal to $10^{-5}$ M.

Cultures of SKOV-3 cells were treated with drug solutions on day 1 after seeding. Aliquots of the working solutions (2 μL) were added to 200 μL cultures to a final concentration of paclitaxel in cultures equal to $10^{-7}$ M. In control cultures 2 μL of medium with 5% FBS was added as solvent control. After cultivation for two consecutive days, the number of viable cells in cultures was counted in order to evaluate the cytotoxicity of the tested solutions of the formulation.

After three days of cultivation the control cultures contained (50.5±2.58)×$10^3$ cells.

The cultures, treated by paclitaxel in a concentration of 100 nM, contained (14.6±0.82)×$10^3$ cells, cell growth inhibition was 71.1% (p<0.001).

The cultures of SKOV-3 cells, treated by solutions of the formulation at the molar ratio paclitaxel/compound II-1a equal to 1:3, 1:6, and 1:10 in medium with 5% FBS, had the following number of viable cells:

1:3: (10.1±0.73)×$10^3$, cell growth inhibition was 80.0% (p<0.001), cell growth inhibition compared to that of paclitaxel was increased by 30.8% (p<0.002);

1:6: (9.4±0.80)×$10^3$, cell growth inhibition was 81.4% (p<0.001), cell growth inhibition compared to that of paclitaxel was increased by 35.6% (p<0.001);

1:10: (8.9±0.64)×$10^3$, cell growth inhibition was 82.4% (p<0.001), cell growth inhibition compared to that of paclitaxel was increased by 39.0% (p<0.001).

Example 33

Evaluation of the Cytotoxicity of the Formulation Paclitaxel/Compound II-1a in Cultures of Human Ovary Adenocarcinoma SKOV-3 Cell Line at Molar Ratio Paclitaxel:Compound II-1a (1:6) Related to the Final Concentration of Paclitaxel/Compound II-1a in Cultures An aliquot of a stock solution of the sodium salt of compound II-1a (2 mg) in ethanol-water (2:1, v/v) was evaporated on a rotary evaporator under reduced pressure. The resulting dried film was dissolved in methanol. A solution of paclitaxel in methanol and the solution of compound II-1a in methanol was mixed. After stirring the organic solvent was evaporated. The resulting dried film was dissolved in saline.

From this initial solution the working solutions in medium with 5% FBS for adding to cultures were prepared. Cultures of SKOV-3 cells were treated with drug solutions on day 1 after seeding. Aliquots of working solutions (2 μL) with different concentrations of formulation were added to 200 μL cultures to a final concentration of paclitaxel 1×$10^{-9}$, 1×$10^{-8}$ and 1×$10^{-7}$ mol/L in the cultures.

In control cultures 2 μL of medium with 5% FBS was added as solvent control. After cultivation for two consecutive days, the number of viable cells in cultures was counted in order to evaluate the cytotoxicity of the tested solutions of the formulation (Table 10).

TABLE 10

Evaluation of the cytotoxicity of the formulation paclitaxel/compound II-1a in cultures of human ovary adenocarcinoma SKOV-3 cell line at molar ratio paclitaxel: compound 11-1 a (1:6) related to the final concentration of paclitaxel/compound II-1a in cultures

| Drug | Formulation | | Tumor Cell Number, × $10^3$ | Cell growth Inhibition, % | Positive Effect, % | $IC_{50}$ mol/L (a) |
|---|---|---|---|---|---|---|
| | Paclitaxel, mol/L | Compound II-1a, mol/L | | | | |
| Control | 0 | 0 | 49.6 ± 3.13 | — | — | — |
| Paclitaxel | $10^{-9}$ | 0 | 37.3 ± 1.80 | 24.8** | — | $4.5 \times 10^{-9}$ |
| | $10^{-8}$ | 0 | 19.9 ± 1.45 | 59.9* | — | |
| | $10^{-7}$ | 0 | 14.1 ± 0.98 | 71.6* | — | |
| Formulation | $10^{-9}$ | $6 \times 10^{-9}$ | 28.4 ± 1.72 | 42.7* | +23.9** | $1.6 \times 10^{-9}$ |
| | $10^{-8}$ | $6 \times 10^{-8}$ | 14.2 ± 1.00 | 71.4* | +28.6** | |
| | $10^{-7}$ | $6 \times 10^{-7}$ | 9.3 ± 0.64 | 81.3* | +34.0• | |

(a) Cell growth inhibition data, determined at three different concentrations, were used to calculate the drug concentrations that inhibited cell growth by 50% as compared to untreated control cultures. All data are the means of three determinations each in six replicates.
*p < 0.001
**p < 0.01
•p < 0.002

Example 34

Evaluation of the Cytotoxicity of the Formulation Doxorubicin/Compound I-1d in Cultures of Human Breast Adenocarcinoma MDA-MB-231 Cell Line, Related to Molar Ratios Doxorubicin:Compound I-1d An aliquot of a stock solution of the sodium salt of compound I-1d (2 mg) in ethanol-water (2:1, v/v) was evaporated on a rotary evaporator under reduced pressure. The resulting dried film was dissolved in water. An aliquot of the obtained solution and an aliquot solution of doxorubicin in water was mixed.

Initial solutions of the formulation in water at the molar ratios doxorubicin:compound I-1d equal to 1:3, 1:6 and 1:10 were prepared. From these solutions the working solutions in medium with 5% FBS for adding to cultures were prepared. The concentration of doxorubicin was equal to $10^{-5}$ M.

Cultures of MDA-MB-231 cells were treated with drug solutions on day 1 after seeding. Aliquots of the working solutions (2 µL) were added to 200 µL cultures to a final concentration of doxorubicin in cultures equal to $10^{-7}$ M. In control cultures 2 µL of medium with 5% FBS was added as solvent control. After cultivation for two consecutive days, the number of viable cells in cultures was counted in order to evaluate the cytotoxicity of the tested solutions of the formulation.

After three days of cultivation the control cultures contained (50.9±2.07)×$10^3$ cells.

The cultures, treated by doxorubicin in a concentration of 100 nM, contained (23.6±1.02)×$10^3$ cells, cell growth inhibition was 53.6% (p<0.001).

The cultures of MDA-MB-231 cells, treated by solutions of the formulation at the molar ratio doxorubicin/compound I-1d equal to 1:3, 1:6 and 1:10 in medium with 5% FBS, had the following number of viable cells:

1:3: (12.2±0.62)×$10^3$, cell growth inhibition was 76.0% (p<0.001), cell growth inhibition compared to that of doxorubicin was increased by 48.3% (p<0.001);

1:6: (12.1±0.69)×$10^3$, cell growth inhibition was 76.2% (p<0.001), cell growth inhibition compared to that of doxorubicin was increased by 48.7% (p<0.001);

1:10: (11.9±0.74)×$10^3$, cell growth inhibition was 76.6% (p<0.001), cell growth inhibition compared to that of doxorubicin was increased by 49.6% (p<0.001).

Example 35

Evaluation of the Cytotoxicity of the Formulation Doxorubicin/Compound I-1d in Cultures of Human Breast Adenocarcinoma MDA-MB-231 Cell Line, at Molar Ratio Doxorubicin:Compound I-1d (1:6) Related to the Final Concentration of Doxorubicin/Compound I-1d in Cultures An aliquot of a stock solution of the sodium salt of compound I-1d (2 mg) in ethanol-water (2:1, v/v) was evaporated on a rotary evaporator under reduced pressure. The resulting dried film was dissolved in water. An aliquot of the obtained solution and the aliquot solution of doxorubicin in water was mixed.

From this initial solution the working solutions in medium with 5% FBS for adding to cultures were prepared. Cultures of MDA-MB-231 cells were treated with drug solutions on day 1 after seeding. Aliquots of working solutions (2 µL) with different concentrations of formulation were added to 200 µL cultures to a final concentration of doxorubicin $1\times10^{-9}$, $1\times10^{-8}$ and $1\times10^{-7}$ mol/L in the cultures. In control cultures 2 µL of medium with 5% FBS was added as solvent control. After cultivation for two consecutive days, the number of viable cells in cultures was counted in order to evaluate the cytotoxicity of the tested solutions of the formulation (Table 11).

TABLE 11

Evaluation of the cytotoxicity of the formulation doxorubicin/compound
I-1d in cultures of human breast adenocarcinoma MDA-MB-231
cell line, at molar ratio doxorubicin:compound I-1d (1:6) related to
the final concentration of doxorubicin/compound I-1d in cultures

| Drug | Formulation Doxorubicin, mol/L | Compound I-1d, mol/L | Tumor Cell Number, × $10^3$ | Cell Growth Inhibition, % | Positive Effect, % | $IC_{50}$ mol/L (a) |
|---|---|---|---|---|---|---|
| Control | 0 | 0 | 55.7 ± 2.49 | — | — | — |
| Doxorubicin | $10^{-9}$ | 0 | 48.0 ± 1.85 | 13.8** | — | $7.6 \times 10^{-8}$ |
|  | $10^{-8}$ | 0 | 41.0 ± 1.50 | 26.4* | — |  |
|  | $10^{-7}$ | 0 | 26.2 ± 1.29 | 53.0* | — |  |
| Formulation | $10^{-9}$ | $3 \times 10^{-9}$ | 37.7 ± 1.62 | 32.2* | +21.5• | $1.3 \times 10^{-8}$ |
|  | $10^{-8}$ | $3 \times 10^{-8}$ | 29.7 ± 1.48 | 46.7* | +27.6* |  |
|  | $10^{-7}$ | $3 \times 10^{-7}$ | 13.5 ± 0.74 | 75.8* | +48.5* |  |

(a) Cell growth inhibition data, determined at three different concentrations, were used to calculate the drug concentrations that inhibited cell growth by 50% as compared to untreated control cultures. All data are the means of three determinations each in six replicates.
*p < 0.001
**p < 0.05
•p < 0.002

Example 36

Evaluation of the Cytotoxicity of the Formulation Doxorubicin/Compound II-1d in Cultures of Human Breast Adenocarcinoma MDA-MB-231 Cell Line, Related to Molar Ratios Doxorubicin:Compound II-1d An aliquot of a stock solution of the sodium salt of compound II-1d (2 mg) in ethanol-water (2:1, v/v) was evaporated on a rotary evaporator under reduced pressure. The resulting dried film was dissolved in water. An aliquot of the obtained solution and the aliquot solution of doxorubicin in water was mixed.

Initial solutions of the formulation in water at the molar ratios doxorubicin:compound II-1d equal to 1:3, 1:6 and 1:10 were prepared. From these solutions the working solutions in medium with 5% FBS for adding to cultures were prepared. Concentration of doxorubicin was equal to $10^{-5}$ M.

Cultures of MDA-MB-231 cells were treated with drug solutions on day 1 after seeding. Aliquots of the working solutions (2 μL) were added to 200 μL cultures to a final concentration of doxorubicin in cultures equal to $10^{-7}$ M. In control cultures 2 μL of medium with 5% FBS was added as solvent control. After cultivation for two consecutive days, the number of viable cells in cultures was counted in order to evaluate the cytotoxicity of the tested solutions of the formulation.

After three days of cultivation the control culture contained (50.9±2.07)×$10^3$ cells.

The cultures, treated by doxorubicin in a concentration of 100 nM, contained (23.6±1.02)×$10^3$ cells, cell growth inhibition was 53.6% (p<0.001).

The cultures of MDA-MB-231 cells, treated by solutions of the formulation at the molar ratio doxorubicin/compound II-1d equal to 1:3, 1:6 and 1:10 in medium with 5% FBS, had the following number of viable cells:

1:3: (13.0±0.76)×$10^3$, cell growth inhibition was 74.5% (p<0.001), cell growth inhibition compared to that of doxorubicin was increased by 44.9% (p<0.001);

1:6: (12.8±0.60)×$10^3$, cell growth inhibition was 74.9% (p<0.001), cell growth inhibition compared to that of doxorubicin was increased by 45.8% (p<0.001);

1:10: (12.6±0.68)×$10^3$, cell growth inhibition was 75.2% (p<0.001), cell growth inhibition compared to that of doxorubicin was increased by 46.6% (p<0.001).

Example 37

Evaluation of the Cytotoxicity of the Formulation Doxorubicin/Compound II-1d in Cultures of Human Breast Adenocarcinoma MDA-MB-231 Cell Line, at Molar Ratio Doxorubicin:Compound II-1d (1:6) Related to the Final Concentration of Doxorubicin/Compound II-1d in Cultures An aliquot of a stock solution of the sodium salt of compound II-1d (2 mg) in ethanol-water (2:1, v/v) was evaporated on a rotary evaporator under reduced pressure. The resulting dried film was dissolved in water. An aliquot of the obtained solution and the aliquot solution of doxorubicin in water was mixed.

From this initial solution the working solutions in medium with 5% FBS for adding to cultures were prepared. Cultures of MDA-MB-231 cells were treated with drug solutions on day 1 after seeding. Aliquots of working solutions (2 μL) with different concentrations of formulation were added to 200 μL cultures to a final concentration of doxorubicin $1 \times 10^{-9}$, $1 \times 10^{-8}$ and $1 \times 10^{-7}$ mol/L in the cultures.

In control cultures 2 μL of medium with 5% FBS was added as solvent control. After cultivation for two consecutive days, the number of viable cells in cultures was counted in order to evaluate the cytotoxicity of the tested solutions of the formulation (Table 12).

TABLE 12

Evaluation of the cytotoxicity of the formulation doxorubicin/compound II-1d in cultures of human breast adenocarcinoma MDA-MB-231 cell line, at molar ratio doxorubicin:compound II-1d (1:6) related to the final concentration of doxorubicin/compound II-1d in cultures

| Drug | Formulation | | Tumor Cell Number, $\times 10^3$ | Cell Growth Inhibition, % | Positive Effect, % | $IC_{50}$ mol/L (a) |
|---|---|---|---|---|---|---|
| | Doxorubicin, mol/L | Compound II-1d, mol/L | | | | |
| Control | 0 | 0 | 55.7 ± 2.49 | — | — | — |
| Doxorubicin | $10^{-9}$ | 0 | 48.0 ± 1.85 | 13.8** | — | $7.6 \times 10^{-8}$ |
| | $10^{-8}$ | 0 | 41.0 ± 1.50 | 26.4* | — | |
| | $10^{-7}$ | 0 | 26.2 ± 1.29 | 53.0* | — | |
| Formulation | $10^{-9}$ | $3 \times 10^{-9}$ | 39.6 ± 1.76 | 28.9* | +17.5• | $1.6 \times 10^{-8}$ |
| | $10^{-8}$ | $3 \times 10^{-8}$ | 31.2 ± 1.53 | 44.0* | +23.9* | |
| | $10^{-7}$ | $3 \times 10^{-7}$ | 14.5 ± 0.81 | 74.0* | +44.7* | |

(a) Cell growth inhibition data, determined at three different concentrations, were used to calculate the drug concentrations that inhibited cell growth by 50% as compared to untreated control cultures. All data are the means of three determinations each in six replicates.
*p < 0.001
**p < 0.05
•p < 0.01

Example 38

Evaluation of the Cytotoxicity of the Formulation Mitoxantrone/Compound I-1e in Cultures of Human Breast Adenocarcinoma MDA-MB-231 Cell Line Related to Molar Ratios Mitoxantrone:Compound I-1e An aliquot of a stock solution of the sodium salt of compound I-1e (2 mg) in ethanol-water (2:1, v/v) was evaporated on a rotary evaporator under reduced pressure. The resulting dried film was dissolved in water. An aliquot of the obtained solution and the aliquot solution of mitoxantrone in water was mixed.

Initial solutions of the formulation in water at the molar ratios mitoxantrone:compound I-1e equal to 1:3, 1:6 and 1:10 were prepared. From these solutions the working solutions in medium with 5% FBS for adding to cultures were prepared. Concentration of mitoxantrone was equal to $10^{-5}$ M.

Cultures of MDA-MB-231 cells were treated with drug solutions on day 1 after seeding. Aliquots of the working solutions (2 μL) were added to 200 μL cultures to a final concentration of mitoxantrone in cultures equal to $10^{-7}$ M. In control cultures 2 μL of medium with 5% FBS was added as solvent control. After cultivation for two consecutive days, the number of viable cells in cultures was counted in order to evaluate the cytotoxicity of the tested solutions of the formulation.

After three days of cultivation the control cultures contained $(55.6\pm2.88)\times10^3$ cells.

The cultures, treated by mitoxantrone in a concentration of 100 nM, contained $(22.9\pm1.49)\times10^3$ cells, cell growth inhibition was 58.8% (p<0.001).

The cultures of MDA-MB-231 cells, treated by solutions of the formulation at the molar ratio mitoxantrone/compound I-1e equal to 1:3, 1:6 and 1:10 in medium with 5% FBS, had the following number of viable cells:

1:3: $(13.7\pm1.05)\times10^3$, cell growth inhibition was 75.4% (p<0.001), cell growth inhibition compared to that of mitoxantrone was increased by 40.2% (p<0.001);

1:6: $(12.5\pm0.98)\times10^3$, cell growth inhibition was 77.5% (p<0.001), cell growth inhibition compared to that of mitoxantrone was increased by 45.4% (p<0.001);

1:10: $(11.9\pm0.82)\times10^3$, cell growth inhibition was 78.6% (p<0.001), cell growth inhibition compared to that of mitoxantrone was increased by 48.0% (p<0.001).

Example 39

Evaluation of the Cytotoxicity of the Formulation Mitoxantrone/Compound I-1e in Cultures of Human Breast Adenocarcinoma MDA-MB-231 Cell Line at Molar Ratio Mitoxantrone:Compound I-1e (1:6) Related to the Final Concentration of Mitoxantrone/Compound I-1e in Cultures An aliquot of a stock solution of the sodium salt of compound I-1e (2 mg) in ethanol-water (2:1, v/v) was evaporated on a rotary evaporator under reduced pressure. The resulting dried film was dissolved in water. An aliquot of the obtained solution and aliquot solution of mitoxantrone in water was mixed.

From this initial solution the working solutions in medium with 5% FBS for adding to cultures were prepared. Cultures of MDA-MB-231 cells were treated with drug solutions on day 1 after seeding. Aliquots of working solutions (2 μL) with different concentrations of formulation were added to 200 μL cultures to a final concentration of mitoxantrone $1\times10^{-9}$, $1\times10^{-8}$ and $1\times10^{-7}$ mol/L in the cultures.

In the control cultures, 2 μL of medium with 5% FBS was added as solvent control. After cultivation for two consecutive days, the number of viable cells in cultures was counted in order to evaluate the cytotoxicity of the tested solutions of the formulation (Table 13).

TABLE 13

Evaluation of the cytotoxicity of the formulation mitoxantrone/compound I-1e in cultures of human breast adenocarcinoma MDA-MB-231 cell line at molar ratio mitoxantrone:compound I-1e (1:6) related to the final concentration of mitoxantrone/compound I-1e in cultures

| Drug | Formulation | | Tumor Cell Number, × $10^3$ | Cell Growth Inhibition, % | Positive Effect, % | $IC_{50}$ mol/L (a) |
|---|---|---|---|---|---|---|
| | Mitoxantrone, mol/L | Compound I-1e, mol/L | | | | |
| Control | 0 | 0 | 57.8 ± 1.97 | — | — | — |
| Mitoxantrone | $10^{-9}$ | 0 | 32.6 ± 1.99 | 43.6* | — | $5.0 \times 10^{-9}$ |
| | $10^{-8}$ | 0 | 27.4 ± 1.90 | 52.6* | — | |
| | $10^{-7}$ | 0 | 22.5 ± 1.63 | 61.1* | — | |
| Formulation | $10^{-9}$ | $6 \times 10^{-9}$ | 25.1 ± 1.88 | 56.6* | +23.0• | $2.5 \times 10^{-10}$ (b) |
| | $10^{-8}$ | $6 \times 10^{-8}$ | 18.3 ± 0.55 | 68.3* | +33.2* | |
| | $10^{-7}$ | $6 \times 10^{-7}$ | 11.6 ± 0.86 | 79.9* | +48.4* | |

(a) Cell growth inhibition data, determined at three different concentrations, were used to calculate the drug concentrations that inhibited cell growth by 50% as compared to untreated control cultures. All data are the means of three determinations each in six replicates.
(b) Extrapolated.
*$p < 0.001$
**$p < 0.01$
•$p < 0.02$

Example 40

Evaluation of the Cytotoxicity of the Formulation Mitoxantrone/Compound II-1e in Cultures of Human Breast Adenocarcinoma MDA-MB-231 Cell Line Related to Molar Ratios Mitoxantrone:Compound II-1e An aliquot of a stock solution of the sodium salt of compound II-1e (2 mg) in ethanol-water (2:1, v/v) was evaporated on a rotary evaporator under reduced pressure. The resulting dried film was dissolved in water. An aliquot of the obtained solution and the aliquot solution of mitoxantrone in water was mixed.

Initial solutions of the formulation in water at the molar ratios mitoxantrone:compound II-1e equal to 1:3, 1:6 and 1:10 were prepared. From these solutions the working solutions in medium with 5% FBS for adding to cultures were prepared. The concentration of mitoxantrone was equal to $10^{-5}$ M.

Cultures of MDA-MB-231 cells were treated with drug solutions on day 1 after seeding. Aliquots of the working solutions (2 µL) were added to 200 µL cultures to a final concentration of mitoxantrone in cultures equal to $10^{-7}$ M. In control cultures 2 µL of medium with 5% FBS was added as solvent control. After cultivation for two consecutive days, the number of viable cells in cultures was counted in order to evaluate the cytotoxicity of the tested solutions of the formulation.

After three days of cultivation the control cultures contained (55.6±2.88)×$10^3$ cells.

The cultures, treated by mitoxantrone in a concentration of 100 nM, contained (22.9±1.49)×$10^3$ cells, cell growth inhibition was 58.8% ($p<0.001$).

The cultures of MDA-MB-231 cells, treated by solutions of the formulation at the molar ratio mitoxantrone/compound II-1e equal to 1:3, 1:6 and 1:10 in medium with 5% FBS, had the following number of viable cells:

1:3: (14.0±1.23)×$10^3$, cell growth inhibition was 74.8% ($p<0.001$), cell growth inhibition compared to that of mitoxantrone was increased by 38.9% ($p<0.001$);

1:6: (12.9±0.62)×$10^3$, cell growth inhibition was 76.8% ($p<0.001$), cell growth inhibition compared to that of mitoxantrone was increased by 43.7% ($p<0.001$);

1:10: (12.3±1.01)×$10^3$, cell growth inhibition was 77.9% ($p<0.001$), cell growth inhibition compared to that of mitoxantrone was increased by 46.3% ($p<0.001$).

Example 41

Evaluation of the Cytotoxicity of the Formulation Mitoxantrone/Compound II-1e in Cultures of Human Breast Adenocarcinoma MDA-MB-231 Cell Line at Molar Ratio Mitoxantrone:Compound II-1e (1:6) Related to the Final Concentration of Mitoxantrone/Compound II-1e in Cultures An aliquot of a stock solution of the sodium salt of compound II-1e (2 mg) in ethanol-water (2:1, v/v) was evaporated on a rotary evaporator under reduced pressure. The resulting dried film was dissolved in water. An aliquot of the obtained solution and the aliquot solution of mitoxantrone in water was mixed.

From this initial solution the working solutions in medium with 5% FBS for adding to cultures were prepared. Cultures of MDA-MB-231 cells were treated with drug solutions on day 1 after seeding. Aliquots of working solutions (2 µL) with different concentrations of formulation were added to 200 µL cultures to a final concentration of mitoxantrone $1\times10^{-9}$, $1\times10^{-8}$ and $1\times10^{-7}$ mol/L in the cultures.

In control cultures 2 µL of medium with 5% FBS was added as solvent control. After cultivation for two consecutive days, the number of viable cells in cultures was counted in order to evaluate the cytotoxicity of the tested solutions of the formulation (Table 14).

TABLE 14

Evaluation of the cytotoxicity of the formulation mitoxantrone/compound
II-Ie in cultures of human breast adenocarcinoma MDA-MB-231 cell line
at molar ratio mitoxantrone:compound II-1e (1:6) related to the final
concentration of mitoxantrone/compound II-1e in cultures

| Drug | Formulation | | Tumor Cell Number, $\times 10^3$ | Cell Growth Inhibition, % | Positive Effect, % | $IC_{50}$ mol/L (a) |
|---|---|---|---|---|---|---|
| | Mitoxantrone, mol/L | Compound II-1e, mol/L | | | | |
| Control | 0 | 0 | 57.8 ± 1.97 | — | — | — |
| Mitoxantrone | $10^{-9}$ | 0 | 32.6 ± 1.99 | 43.6* | — | $5.0 \times 10^{-9}$ |
| | $10^{-8}$ | 0 | 27.4 ± 1.90 | 52.6* | — | |
| | $10^{-7}$ | 0 | 22.5 ± 1.63 | 61.1* | — | |
| Formulation | $10^{-9}$ | $6 \times 10^{-9}$ | 26.2 ± 1.43 | 54.7 | +19.6• | $4.0 \times 10^{-10}$ (b) |
| | $10^{-8}$ | $6 \times 10^{-8}$ | 19.5 ± 1.12 | 66.3 | +28.8** | |
| | $10^{-7}$ | $6 \times 10^{-7}$ | 13.0 ± 0.91 | 77.5 | +42.2* | |

(a) Cell growth inhibition data, determined at three different concentrations, were used to calculate the drug concentrations that inhibited cell growth by 50% as compared to untreated control cultures. All data are the means of three determinations each in six replicates.
(b) Extrapolated.
*$p < 0.001$
**$p < 0.01$
•$p < 0.05$ Example 42

Evaluation of the Cytotoxicity of the Formulation Mitoxantrone/Compound I-1f in Cultures of Human Prostate Carcinoma DU 145 Cell Line Related to Molar Ratios Mitoxantrone:Compound I-1f An aliquot of a stock solution of the sodium salt of compound I-1f (2 mg) in ethanol-water (2:1, v/v) was evaporated on a rotary evaporator under reduced pressure. The resulting dried film was dissolved in water. An aliquot of the obtained solution and the aliquot solution of mitoxantrone in water was mixed.

Initial solutions of the formulation in water at the molar ratios mitoxantrone:compound I-1f equal to 1:3, 1:6 and 1:10 were prepared. From these solutions the working solutions in medium with 5% FBS for adding to cultures were prepared. The concentration of mitoxantrone was equal to $10^{-5}$ M.

Cultures of DU 145 cells were treated with drug solutions on day 1 after seeding. Aliquots of the working solutions (2 µL) were added to 200 µL cultures to a final concentration of mitoxantrone in cultures equal to $10^{-7}$ M. In control cultures 2 µL of medium with 5% FBS was added as solvent control. After cultivation for two consecutive days, the number of viable cells in cultures was counted in order to evaluate the cytotoxicity of the tested solutions of the formulation.

After three days of cultivation the control cultures contained $(48.2 \pm 3.14) \times 10^3$ cells.

The cultures, treated by mitoxantrone in a concentration of 100 nM, contained $(19.2 \pm 1.16) \times 10^3$ cells, cell growth inhibition was 60.2% ($p < 0.001$).

The cultures of DU 145 cells, treated by solutions of the formulation at the molar ratio mitoxantrone/compound I-1f equal to 1:3, 1:6 and 1:10 in medium with 5% FBS, had the following number of viable cells:

1:3: $(9.9 \pm 0.48) \times 10^3$, cell growth inhibition was 79.5% ($p < 0.001$), cell growth inhibition compared to that of mitoxantrone was increased by 48.4% ($p < 0.001$);

1:6: $(9.3 \pm 0.54) \times 10^3$, cell growth inhibition was 80.7% ($p < 0.001$), cell growth inhibition compared to that of mitoxantrone was increased by 51.6% ($p < 0.001$);

1:10: $(8.8 \pm 0.65) \times 10^3$, cell growth inhibition was 81.7% ($p < 0.001$), cell growth inhibition compared to that of mitoxantrone was increased by 54.2% ($p < 0.001$).

Example 43

Evaluation of the Cytotoxicity of the Formulation Mitoxantrone/Compound I-1f in Cultures of Human Prostate Carcinoma DU 145 Cell Line at Molar Ratio Mitoxantrone:Compound I-1f (1:6) Related to the Final Concentration of Mitoxantrone/Compound I-1f in Cultures An aliquot of a stock solution of the sodium salt of compound I-1f (2 mg) in ethanol-water (2: 1, v/v) was evaporated on a rotary evaporator under reduced pressure. The resulting dried film was dissolved in water. An aliquot of the obtained solution and the aliquot solution of mitoxantrone in water was mixed.

From this initial solution the working solutions in medium with 5% FBS for adding to cultures were prepared. Cultures of DU 145 cells were treated with drug solutions on day 1 after seeding. Aliquots of working solutions (2 µL) with different concentrations of formulation were added to 200 µL cultures to a final concentration of mitoxantrone $1 \times 10^{-9}$, $1 \times 10^{-8}$ and $1 \times 10^{-7}$ mol/L in the cultures. In control cultures 2 µL of medium with 5% FBS was added as solvent control. After cultivation for two consecutive days, the number of viable cells in cultures was counted in order to evaluate the cytotoxicity of the tested solutions of the formulation (Table 15).

TABLE 15

Evaluation of the cytotoxicity of the formulation mitoxantrone/compound
I-1f in cultures of human prostate carcinoma DU 145 cell line at molar
ratio mitoxantrone:compound I-1f (1:6) related to the final
concentration of mitoxantrone/compound I-1f in cultures

| Drug | Formulation Mitoxantrone, mol/L | Compound I-1f, mol/L | Tumor Cell Number, × $10^3$ | Cell Growth Inhibition, % | Positive Effect, % | $IC_{50}$ mol/L (a) |
|---|---|---|---|---|---|---|
| Control | 0 | 0 | 57.5 ± 3.03 | — | — | — |
| Mitoxantrone | $10^{-9}$ | 0 | 46.5 ± 2.32 | 19.1• | — | $3.2 \times 10^{-8}$ |
|  | $10^{-8}$ | 0 | 35.0 ± 1.70 | 39.1* | — |  |
|  | $10^{-7}$ | 0 | 23.1 ± 1.34 | 59.8* | — |  |
| Formulation | $10^{-9}$ | $6 \times 10^{-9}$ | 37.9 ± 2.86 | 34.1* | +18.5•• | $5.2 \times 10^{-9}$ |
|  | $10^{-8}$ | $6 \times 10^{-8}$ | 25.2 ± 0.93 | 56.2* | +28.0* |  |
|  | $10^{-7}$ | $6 \times 10^{-7}$ | 11.4 ± 0.74 | 80.2* | +50.6* |  |

(a) Cell growth inhibition data, determined at three different concentrations, were used to calculate the drug concentrations that inhibited cell growth by 50% as cornpared to untreated control cultures. All data are the means of three determinations each in six replicates.
*$p < 0.001$
**$p < 0.01$
•$p < 0.02$
••$p < 0.05$ Example 44

Evaluation of the Cytotoxicity of the Formulation Mitoxantrone/Compound II-1f in Cultures of Human Prostate Carcinoma DU 145 Cell Line Related to Molar Ratios Mitoxantrone:Compound II-1f An aliquot of a stock solution of the sodium salt of compound II-1f (2 mg) in ethanol-water (2:1, v/v) was evaporated on a rotary evaporator under reduced pressure. The resulting dried film was dissolved in water. An aliquot of the obtained solution and the aliquot solution of mitoxantrone in water was mixed.

Initial solutions of the formulation in water at the molar ratios mitoxantrone:compound II-1f equal to 1:3, 1:6 and 1:10 were prepared. From these solutions the working solutions in medium with 5% FBS for adding to cultures were prepared. The concentration of mitoxantrone was equal to $10^{-5}$ M.

Cultures of DU 145 cells were treated with drug solutions on day 1 after seeding. Aliquots of the working solutions (2 μL) were added to 200 μL cultures to a final concentration of mitoxantrone in cultures equal to $10^{-7}$ M. In control cultures 2 μL of medium with 5% FBS was added as solvent control. After cultivation for two consecutive days, the number of viable cells in cultures was counted in order to evaluate the cytotoxicity of the tested solutions of the formulation.

After three days of cultivation the control cultures contained (48.2±3.14)×$10^3$ cells.

The cultures, treated by mitoxantrone in a concentration of 100 nM, contained (19.2±1.16)×$10^3$ cells, cell growth inhibition was 60.2% ($p<0.001$).

The cultures of DU 145 cells, treated by solutions of the formulation at the molar ratio mitoxantrone/compound II-1f equal to 1:3, 1:6 and 1:10 in medium with 5% FBS, had the following number of viable cells:

1:3: (10.9±0.83)×$10^3$, cell growth inhibition was 77.4% ($p<0.001$), cell growth inhibition compared to that of mitoxantrone was increased by 43.2% ($p<0.001$);

1:6: (10.4±0.70)×$10^3$, cell growth inhibition was 78.4% ($p<0.001$), cell growth inhibition compared to that of mitoxantrone was increased by 45.8% ($p<0.001$);

1:10: (9.7±0.53)×$10^3$, cell growth inhibition was 79.9% ($p<0.001$), cell growth inhibition compared to that of mitoxantrone was increased by 49.5% ($p<0.001$).

Example 45

Evaluation of the Cytotoxicity of the Formulation Mitoxantrone/Compound II-1f in Cultures of Human Prostate Carcinoma DU 145 Cell Line at Molar Ratio Mitoxantrone:Compound II-1f (1:6) Related to the Final Concentration of Mitoxantrone/Compound II-1f in Cultures An aliquot of a stock solution of the sodium salt of compound II-1f (2 mg) in ethanol-water (2:1, v/v) was evaporated on a rotary evaporator under reduced pressure. The resulting dried film was dissolved in water. An aliquot of the obtained solution and the aliquot solution of mitoxantrone in water was mixed.

From this initial solution the working solutions in medium with 5% FBS for adding to cultures were prepared. Cultures of DU 145 cells were treated with drug solutions on day 1 after seeding. Aliquots of working solutions (2 μL) with different concentrations of formulation were added to 200 μL cultures to a final concentration of mitoxantrone 1×$10^{-9}$, 1×$10^{-8}$ and 1×$10^{-7}$ mol/L in the cultures.

In control cultures 2 μL of medium with 5% FBS was added as solvent control. After cultivation for two consecutive days, the number of viable cells in cultures was counted in order to evaluate the cytotoxicity of the tested solutions of the formulation (Table 16).

TABLE 16

Evaluation of the cytotoxicity of the formulation mitoxantrone/compound
II-1f in cultures of human prostate carcinoma DU 145 cell line at molar
ratio mitoxantrone:compound II-1f (1:6) related to the final concentration
of mitoxantrone/compound II-1f in cultures

| Drug | Formulation Mitoxantrone, mol/L | Compound II-1f, mol/L | Tumor Cell Number, × $10^3$ | Cell Growth Inhibition, % | Positive Effect, % | $IC_{50}$ mol/L (a) |
|---|---|---|---|---|---|---|
| Control | 0 | 0 | 57.5 ± 3.03 | — | — | — |
| Mitoxantrone | $10^{-9}$ | 0 | 46.5 ± 2.32 | 19.1• | — | $3.2 \times 10^{-8}$ |
|  | $10^{-8}$ | 0 | 35.0 ± 1.70 | 39.1* | — |  |
|  | $10^{-7}$ | 0 | 23.1 ± 1.34 | 59.8* | — |  |
| Formulation | $10^{-9}$ | $6 \times 10^{-9}$ | 39.3 ± 2.15 | 31.7* | +15.5•• | $7.2 \times 10^{-9}$ |
|  | $10^{-8}$ | $6 \times 10^{-8}$ | 27.1 ± 1.57 | 52.9* | +22.6** |  |
|  | $10^{-7}$ | $6 \times 10^{-7}$ | 13.7 ± 0.88 | 76.2* | +40.7* |  |

(a) Cell growth inhibition data, determined at three different concentrations, were used to calculate the drug concentrations that inhibited cell growth by 50% as compared to untreated control cultures. All data are the means of three determinations each in six replicates.
*$p < 0.001$
**$p < 0.01$
•$p < 0.02$
••$p < 0.05$ Example 46

Evaluation of the Cytotoxicity of Compound I-1g in Cultures of Human Breast Adenocarcinoma MDA-MB-231 Cell Line Related to the Final Concentration of Compound I-1g in the Cultures.

An initial solution of compound I-1g (1 mg/ml) was prepared by dissolving of the dry substance in saline. From this solution, the working solutions of compound I-1g in MEM with 5% FBS were prepared in different concentrations by means of consecutive dilutions for adding to the cultures.

Cultures of MDA-MB-231 cells were treated with drug solutions on day 1 after seeding. Aliquots of working solutions (2 μL) in different concentrations of compound I-1g were added to 200 μL cultures to final concentrations of compound I-1g from $10^{-9}$ to $10^{-7}$ mol/L in the cultures. In the control cultures, 2 μL of medium with 5% FBS was added as solvent control. After cultivation for two consecutive days, the number of viable cells in cultures was counted and the extent of growth inhibition of MDA-MB-231 cells calculated in order to evaluate the cytotoxicity of the tested solutions of compound I-1g.

After three days of cultivation, the control cultures contained (56.5±2.35)×$10^3$ cells.

The cultures, treated by solutions of compound I-1g had the following number of viable cells:

| | |
|---|---|
| $10^{-9}$ mol/L: | (40.8 ± 2.14) × $10^3$, cell growth inhibition was 27.8% ($p < 0.001$); |
| $10^{-8}$ mol/L: | (36.2 ± 1.95) × $10^3$, cell growth inhibition was 35.9% ($p < 0.001$); |
| $10^{-7}$ mol/L: | (32.1 ± 1.72) × $10^3$, cell growth inhibition was 43.2% ($p < 0.001$). |

Thus compound I-1g was shown to exert a significant cytotoxic action against human breast adenocarcinoma cells. The extent of cell growth inhibition increased by 43.2% (p<0.001) when increasing the concentration of compound I-1g.

Example 47

Evaluation of the Cytotoxicity of Compound I-1h in Cultures of Human Breast Adenocarcinoma MDA-MB-231 Cell Line Related to the Final Concentration of Compound I-1h in the Cultures.

An initial solution of compound I-1h (1 mg/ml) was prepared by dissolving of the dry substance in saline. From this solution, the working solutions of compound I-1h in MEM with 5% FBS were prepared in different concentrations by means of consecutive dilutions for adding to the cultures.

Cultures of MDA-MB-231 cells were treated with drug solutions on day 1 after seeding. Aliquots of working solutions (2 μL) in different concentrations of compound I-1h were added to 200 μL cultures to final concentrations of compound I-1h from $10^{-9}$ to $10^{-7}$ mol/L in the cultures. In the control cultures, 2 μL of medium with 5% FBS was added as solvent control. After cultivation for two consecutive days, the number of viable cells in cultures was counted and the extent of growth inhibition of MDA-MB-231 cells calculated in order to evaluate the cytotoxicity of the tested solutions of compound I-1h.

After three days of cultivation, the control cultures contained (56.5±2.35)×$10^3$ cells.

The cultures, treated by solutions of compound I-1h had the following number of viable cells:

| | |
|---|---|
| $10^{-9}$ mol/L: | (38.4 ± 2.11) × $10^3$, cell growth inhibition was 32.0% ($p < 0.001$); |
| $10^{-8}$ mol/L: | (34.1 ± 1.89) × $10^3$, cell growth inhibition was 39.6% ($p < 0.001$); |
| $10^{-7}$ mol/L: | (30.3 ± 1.55) × $10^3$, cell growth inhibition was 46.4% ($p < 0.001$). |

Thus compound I-1h was shown to exert a significant cytotoxic action against human breast adenocarcinoma cells. The extent of cell growth inhibition increased by 46.4% (p<0.001) when increasing the concentration of compound I-1h.

Example 48

Evaluation of the Cytotoxicity of Compound I-3a in Cultures of Human Breast Adenocarcinoma MDA-MB-231 Cell Line Related to the Final Concentration of Compound I-3a in the Cultures.

An initial solution of compound I-3a (1 mg/ml) was prepared by dissolving of the dry substance in saline. From this solution, the working solutions of compound I-3a in MEM with 5% FBS were prepared in different concentrations by means of consecutive dilutions for adding to the cultures.

Cultures of MDA-MB-231 cells were treated with drug solutions on day 1 after seeding. Aliquots of working solutions (2 µL) in different concentrations of compound I-3a were added to 200 µL cultures to final concentrations of compound I-3a from $10^{-9}$ to $10^{-7}$ mol/L in the cultures. In the control cultures, 2 µL of medium with 5% FBS was added as solvent control. After cultivation for two consecutive days, the number of viable cells in cultures was counted and the extent of growth inhibition of MDA-MB-231 cells calculated in order to evaluate the cytotoxicity of the tested solutions of compound I-3a.

After three days of cultivation, the control cultures contained $(56.5 \pm 2.35) \times 10^3$ cells.

The cultures, treated by solutions of compound I-3a had the following number of viable cells:

| | |
|---|---|
| $10^{-9}$ mol/L: | $(40.0 \pm 2.06) \times 10^3$, cell growth inhibition was 29.2% (p < 0.001); |
| $10^{-8}$ mol/L: | $(34.9 \pm 1.64) \times 10^3$, cell growth inhibition was 38.2% (p < 0.001); |
| $10^{-7}$ mol/L: | $(28.8 \pm 1.15) \times 10^3$, cell growth inhibition was 49.0% (p < 0.001). |

Thus compound I-3a was shown to exert a significant cytotoxic action against human breast adenocarcinoma cells. The extent of cell growth inhibition increased by 49.0% (p<0.001) when increasing the concentration of compound I-3a.

Example 49

Evaluation of the Cytotoxicity of Compound I-3f in Cultures of Human Breast Adenocarcinoma MDA-MB-231 Cell Line related to the Final Concentration of Compound I-3f in the Cultures.

An initial solution of compound I-3f (1 mg/ml) was prepared by dissolving of the dry substance in saline. From this solution, the working solutions of compound I-3f in MEM with 5% FBS were prepared in different concentrations by means of consecutive dilutions for adding to the cultures.

Cultures of MDA-MB-231 cells were treated with drug solutions on day 1 after seeding. Aliquots of working solutions (2 µL) in different concentrations of compound I-3f were added to 200 µL cultures to final concentrations of compound I-3f from $10^{-9}$ to $10^{-7}$ mol/L in the cultures. In the control cultures, 2 µL of medium with 5% FBS was added as solvent control. After cultivation for two consecutive days, the number of viable cells in cultures was counted and the extent of growth inhibition of MDA-MB-231 cells calculated in order to evaluate the cytotoxicity of the tested solutions of compound I-3f.

After three days of cultivation, the control cultures contained $(56.5 \pm 2.35) \times 10^3$ cells.

The cultures, treated by solutions of compound I-3f had the following number of viable cells:

| | |
|---|---|
| $10^{-9}$ mol/L: | $(33.1 \pm 1.90) \times 10^3$, cell growth inhibition was 41.4% (p < 0.001); |
| $10^{-8}$ mol/L: | $(29.0 \pm 1.32) \times 10^3$, cell growth inhibition was 48.7% (p < 0.001); |
| $10^{-7}$ mol/L: | $(25.3 \pm 0.76) \times 10^3$, cell growth inhibition was 55.2% (p < 0.001). |

Thus compound I-3f was shown to exert a significant cytotoxic action against human breast adenocarcinoma cells. The extent of cell growth inhibition increased by 55.2% (p<0.001) when increasing the concentration of compound I-3f.

Example 50

Evaluation of the Cytotoxicity of Compound II-3b in Cultures of Human Breast Adenocarcinoma MDA-MB-231 Cell Line Related to the Final Concentration of Compound II-3b in the Cultures.

An initial solution of compound II-3b (1 mg/ml) was prepared by dissolving of the dry substance in saline. From this solution, the working solutions of compound II-3b in MEM with 5% FBS were prepared in different concentrations by means of consecutive dilutions for adding to the cultures.

Cultures of MDA-MB-231 cells were treated with drug solutions on day 1 after seeding. Aliquots of working solutions (2 µL) in different concentrations of compound II-3b were added to 200 µL cultures to final concentrations of compound II-3b from $10^{-9}$ to $10^{-7}$ mol/L in the cultures. In the control cultures, 2 µL of medium with 5% FBS was added as solvent control. After cultivation for two consecutive days, the number of viable cells in cultures was counted and the extent of growth inhibition of MDA-MB-231 cells calculated in order to evaluate the cytotoxicity of the tested solutions of compound II-3b.

After three days of cultivation, the control cultures contained $(56.5 \pm 2.35) \times 10^3$ cells.

The cultures, treated by solutions of compound II-3b had the following number of viable cells:

| | |
|---|---|
| $10^{-9}$ mol/L: | $(29.5 \pm 1.21) \times 10^3$, cell growth inhibition was 47.8% (p < 0.001); |
| $10^{-8}$ mol/L: | $(25.2 \pm 1.27) \times 10^3$, cell growth inhibition was 55.4% (p < 0.001); |
| $10^{-7}$ mol/L: | $(21.4 \pm 0.88) \times 10^3$, cell growth inhibition was 62.1% (p < 0.001). |

Thus compound II-3b was shown to exert a significant cytotoxic action against human breast adenocarcinoma cells. The extent of cell growth inhibition increased by 62.1% (p<0.001) when increasing the concentration of compound II-3b.

Example 51

Comparative Evaluation of the Cytotoxicity of Compound I-1 in Cultures of Human Breast Adenocarcinoma MDA-MB-231 Cell Line Related to Dilutions of its Initial Solutions in Saline with 2.3 mM $CaCl_2$ (A) and Normal Saline (B).

Aliquots of a stock solution of the sodium salt of compound I-1 in ethanol-water (2:1, v/v) were evaporated on the rotary evaporator under reduced pressure. The one resulting dried film was dissolved in saline with 2.3 mM $CaCl_2$ and other dissolved in normal saline to form initial solutions of compound I-1 in a concentration of $10^{-3}$ M. The two working solutions of compound I-1 in saline with 2.3 mM $CaCl_2$ (A) and normal saline (B) in a concentration of $10^{-5}$ M were prepared from these initial solutions.

Cultures of MDA-MB-231 cells were treated with drug solutions on day 1 after seeding. Aliquots of working solutions (2 μL) with different concentrations of compound I-1 in saline with 2.3 mM $CaCl_2$ (A) and normal saline (B) were added to 200 μL cultures to a final concentrations of compound I-1 from $1\times10^{-9}$ to $1\times10^{-7}$ mol/L in the cultures. After cultivation for two consecutive days, the number of viable cells in cultures was counted and the extent of growth inhibition of MDA-MB-231 cells calculated in order to evaluate the cytotoxicity of the tested solutions of compound I-1.

After three days of cultivation, the control cultures contained $(56.9\pm3.30)\times10^3$ cells.

The cultures, treated by solutions of compound I-1 in A and in B had the following number of viable cells:

$10^{-9}$ mol/L: A $(35.9\pm1.38)\times10^3$, cell growth inhibition was 36.9% ($p<0.001$)

B $(42.8\pm1.56)\times10^3$, cell growth inhibition was 24.8% ($p<0.01$)

Cell growth inhibition by I-1 in A compared to that in B was increased by 16.1% ($p<0.01$);

$10^{-8}$ mol/L: A $(34.0\pm1.32)\times10^3$, cell growth inhibition was 40.2% ($p<0.001$)

B $(40.0\pm1.35)\times10^3$, cell growth inhibition was 29.7% ($p<0.001$)

Cell growth inhibition by I-1 in A compared to that in B was increased by 15.0% ($p<0.01$);

$10^{-7}$ mol/L: A $(33.3\pm1.17)\times10^3$, cell growth inhibition was 41.5% ($p<0.001$)

B $(39.1\pm1.41)\times10^3$, cell growth inhibition was 31.3% ($p<0.001$)

Cell growth inhibition by I-1 in A compared to that in B was increased by 14.8% ($p<0.01$).

Example 52

Comparative Evaluation of the Cytotoxicity of Compound II-1 in Cultures of Human Breast Adenocarcinoma MDA-MB-231 Cell Line Related to Dilutions of its Initial Solution in Saline with 2.3 mM $CaCl_2$ (A) and Normal Saline (B).

Aliquots of a stock solution of the sodium salt of compound II-1 in ethanol-water (2:1, v/v) were evaporated on the rotary evaporator under reduced pressure. The one resulting dried film was dissolved in saline with 2.3 mM $CaCl_2$ and other dissolved in normal saline to form initial solutions of compound II-1 in a concentration of $10^{-3}$ M. The two working solutions of compound II-1 in saline with 2.3 mM $CaCl_2$ (A) and normal saline (B) in a concentration of $10^{-5}$ M were prepared from these initial solutions.

Cultures of MDA-MB-231 cells were treated with drug solutions on day 1 after seeding. Aliquots of working solutions (2 μL) with different concentrations of compound II-1 in saline with 2.3 mM $CaCl_2$ (A) and normal saline (B) were added to 200 μL cultures to a final concentrations of compound II-1 from $1\times10^{-9}$ to $1\times10^{-7}$ mol/L in the cultures. After cultivation for two consecutive days, the number of viable cells in cultures was counted and the extent of growth inhibition of MDA-MB-231 cells calculated in order to evaluate the cytotoxicity of the tested solutions of compound II-1.

After three days of cultivation, the control cultures contained $(56.9\pm3.30)\times10^3$ cells.

The cultures, treated by solutions of compound II-1 in A and in B had the following number of viable cells:

$10^{-9}$ mol/L: A $(35.6\pm1.29)\times10^3$, cell growth inhibition was 37.4% ($p<0.001$)

B $(42.4\pm1.63)\times10^3$, cell growth inhibition was 25.5% ($p<0.01$)

Cell growth inhibition by II-1 in A compared to that in B was increased by 16.0% ($p<0.01$);

$10^{-8}$ mol/L: A $(33.4\pm1.20)\times10^3$, cell growth inhibition was 41.3% ($p<0.001$)

B $(39.5\pm1.46)\times10^3$, cell growth inhibition was 30.6% ($p<0.001$)

Cell growth inhibition by II-1 in A compared to that in B was increased by 15.4% ($p<0.01$);

$10^{-7}$ mol/L: A $(32.6\pm1.09)\times10^3$, cell growth inhibition was 42.7% ($p<0.001$)

B $(38.6\pm1.25)\times10^3$, cell growth inhibition was 32.2% ($p<0.001$)

Cell growth inhibition by II-1 in A compared to that in B was increased by 15.5% ($p<0.01$).

Example 53

Comparative Evaluation of the Cytotoxicity of Compound I-1a in Cultures of Human Breast Adenocarcinoma MDA-MB-231 Cell Line Related to Dilutions of its Initial Solution in Saline with 2.3 mM $CaCl_2$ (A) and Normal Saline (B).

Aliquots of a stock solution of the sodium salt of compound II-1a in ethanol-water (2:1, v/v) were evaporated on the rotary evaporator under reduced pressure. The one resulting dried film was dissolved in saline with 2.3 mM $CaCl_2$ and other dissolved in normal saline to form initial solutions of compound II-1a in a concentration of $10^{-3}$ M. The two working solutions of compound II-1a in saline with 2.3 mM $CaCl_2$ (A) and normal saline (B) in a concentration of $10^{-5}$ M were prepared from these initial solutions.

Cultures of MDA-MB-231 cells were treated with drug solutions on day 1 after seeding. Aliquots of working solutions (2 μL) with different concentrations of compound II-1a in saline with 2.3 mM $CaCl_2$ (A) and normal saline (B) were added to 200 μL cultures to a final concentrations of compound II-1a from $1\times10^{-9}$ to $1\times10^{-7}$ mol/L in the cultures. After cultivation for two consecutive days, the number of viable cells in cultures was counted and the extent of growth inhibition of MDA-MB-231 cells calculated in order to evaluate the cytotoxicity of the tested solutions of compound II-1a.

After three days of cultivation, the control cultures contained $(57.3\pm1.70)\times10^3$ cells.

The cultures, treated by solutions of compound II-1a in A and in B had the following number of viable cells:

$10^{-9}$ mol/L: A $(36.8\pm1.74)\times10^3$, cell growth inhibition was 35.8% ($p<0.001$)

B $(44.1\pm2.24)\times10^3$, cell growth inhibition was 23.0% ($p<0.001$)

Cell growth inhibition by II-1a in A compared to that in B was increased by 16.6% ($p<0.05$);

$10^{-8}$ mol/L: A $(33.4\pm1.25)\times10^3$, cell growth inhibition was 41.7% ($p<0.001$)

B $(39.4\pm2.28)\times10^3$, cell growth inhibition was 31.2% ($p<0.001$)

Cell growth inhibition by II-1a in A compared to that in B was increased by 15.2% ($p<0.05$);

$10^{-7}$ mol/L: A $(29.3\pm0.76)\times10^3$, cell growth inhibition was 48.9% ($p<0.001$)

B $(34.1\pm1.97)\times10^3$, cell growth inhibition was 40.5% ($p<0.001$)

Cell growth inhibition by II-1a in A compared to that in B was increased by 14.1% ($p<0.05$).

Example 54

Comparative Evaluation of the Cytotoxicity of Compound I-1f in Cultures of Human Breast Adenocarcinoma MDA-MB-231 Cell Line Related to Dilutions of its Initial Solution in Saline with 2.3 mM $CaCl_2$ (A) and Normal Saline (B).

Aliquots of a stock solution of the sodium salt of compound I-1f in ethanol-water (2:1, v/v) were evaporated on the rotary evaporator under reduced pressure. The one resulting dried film was dissolved in saline with 2.3 mM $CaCl_2$ and other dissolved in normal saline to form initial solutions of compound I-1f in a concentration of $10^{-3}$ M. The two working solutions of compound I-1f in saline with 2.3 mM $CaCl_2$ (A) and normal saline (B) in a concentration of $10^{-5}$ M were prepared from these initial solutions.

Cultures of MDA-MB-231 cells were treated with drug solutions on day 1 after seeding. Aliquots of working solutions (2 μL) with different concentrations of compound I-1f in saline with 2.3 mM $CaCl_2$ (A) and normal saline (B) were added to 200 μL cultures to a final concentrations of compound I-1f from $1\times10^{-9}$ to $1\times10^{-7}$ mol/L in the cultures. After cultivation for two consecutive days, the number of viable cells in cultures was counted and the extent of growth inhibition of MDA-MB-231 cells calculated in order to evaluate the cytotoxicity of the tested solutions of compound I-1f.

After three days of cultivation, the control cultures contained $(57.4\pm3.10)\times10^3$ cells.

The cultures, treated by solutions of compound I-1f in A and in B had the following number of viable cells:

$10^{-9}$ mol/L: A $(35.3\pm1.34)\times10^3$, cell growth inhibition was 38.6% ($p<0.001$)

B $(42.6\pm0.80)\times10^3$, cell growth inhibition was 25.8% ($p<0.001$)

Cell growth inhibition by I-1f in A compared to that in B was increased by 17.1% ($p<0.001$);

$10^{-8}$ mol/L: A $(30.8\pm1.23)\times10^3$, cell growth inhibition was 46.3% ($p<0.001$)

B $(36.7\pm0.75)\times10^3$, cell growth inhibition was 36.1% ($p<0.001$)

Cell growth inhibition by I-1f in A compared to that in B was increased by 16.1% ($p<0.01$);

$10^{-7}$ mol/L: A $(26.8\pm0.63)\times10^3$, cell growth inhibition was 53.3% ($p<0.001$)

B $(31.6\pm0.89)\times10^3$, cell growth inhibition was 44.9% ($p<0.001$)

Cell growth inhibition by I-1f in A compared to that in B was increased by 15.2% ($p<0.002$).

Example 55

Comparative Evaluation of the Cytotoxicity of Compound II-1f in Cultures of Human Breast Adenocarcinoma MDA-MB-231 Cell Line Related to Dilutions of its Initial Solution in Saline with 2.3 mM $CaCl_2$ (A) and Normal Saline (B).

Aliquots of a stock solution of the sodium salt of compound II-1f in ethanol-water (2:1, v/v) were evaporated on the rotary evaporator under reduced pressure. The one resulting dried film was dissolved in saline with 2.3 mM $CaCl_2$ and other dissolved in normal saline to form initial solutions of compound II-1f in a concentration of $10^{-3}$ M. The two working solutions of compound II-1f in saline with 2.3 mM $CaCl_2$ (A) and normal saline (B) in a concentration of $10^{-5}$ M were prepared from these initial solutions.

Cultures of MDA-MB-231 cells were treated with drug solutions on day 1 after seeding. Aliquots of working solutions (2 μL) with different concentrations of compound II-1f in saline with 2.3 mM $CaCl_2$ (A) and normal saline (B) were added to 200 μL cultures to a final concentrations of compound II-1f from $1\times10^{-9}$ to $1\times10^{-7}$ mol/L in the cultures. After cultivation for two consecutive days, the number of viable cells in cultures was counted and the extent of growth inhibition of MDA-MB-231 cells calculated in order to evaluate the cytotoxicity of the tested solutions of compound II-1f.

After three days of cultivation, the control cultures contained $(57.4\pm3.10)\times10^3$ cells.

The cultures, treated by solutions of compound II-1f in A and in B had the following number of viable cells:

$10^{-9}$ mol/L: A $(34.4\pm1.20)\times10^3$, cell growth inhibition was 40.1% ($p<0.001$)

B $(41.8\pm1.46)\times10^3$, cell growth inhibition was 27.2% ($p<0.001$)

Cell growth inhibition by II-1f in A compared to that in B was increased by 17.7% ($p<0.01$);

$10^{-8}$ mol/L: A $(30.2\pm0.75)\times10^3$, cell growth inhibition was 47.4% ($p<0.001$)

B $(36.0\pm1.28)\times10^3$, cell growth inhibition was 37.3% ($p<0.001$)

Cell growth inhibition by II-1f in A compared to that in B was increased by 16.1% ($p<0.01$);

$10^{-7}$ mol/L: A $(26.3\pm0.68)\times10^3$, cell growth inhibition was 54.2% ($p<0.001$)

B $(31.1\pm0.96)\times10^3$, cell growth inhibition was 45.8% ($p<0.001$)

Cell growth inhibition by II-1f in A compared to that in B was increased by 15.4% ($p<0.002$).

Example 56

Comparative Evaluation of the Cytotoxicity of Compound I-1g in Cultures of Human Breast Adenocarcinoma MDA-MB-231 Cell Line Related to Dilutions of its Initial Solution in Saline with 2.3 mM $CaCl_2$ (A) and Normal Saline (B).

Aliquots of a stock solution of the sodium salt of compound I-1g in ethanol-water (2:1, v/v) were evaporated on the rotary evaporator under reduced pressure. The one resulting dried film was dissolved in saline with 2.3 mM $CaCl_2$ and other dissolved in normal saline to form initial solutions of compound I-1g in a concentration of $10^{-3}$ M. The two working solutions of compound I-1g in saline with 2.3 mM $CaCl_2$ (A) and normal saline (B) in a concentration of $10^{-5}$ M were prepared from these initial solutions.

Cultures of MDA-MB-231 cells were treated with drug solutions on day 1 after seeding. Aliquots of working solutions (2 μL) with different concentrations of compound I-1g in saline with 2.3 mM $CaCl_2$ (A) and normal saline (B) were added to 200 μL cultures to a final concentrations of compound I-1g from $1\times10^{-9}$ to $1\times10^{-7}$ mol/L in the cultures. After cultivation for two consecutive days, the number of viable cells in cultures was counted and the extent of growth inhibition of MDA-MB-231 cells calculated in order to evaluate the cytotoxicity of the tested solutions of compound I-1g.

After three days of cultivation, the control cultures contained $(55.8\pm1.37)\times10^3$ cells.

The cultures, treated by solutions of compound I-1g in A and in B had the following number of viable cells:

$10^{-9}$ mol/L: A $(39.9\pm1.76)\times10^3$, cell growth inhibition was 28.5% (p<0.001)

B $(53.5\pm3.21)\times10^3$, cell growth inhibition was 4.2% (p>0.05)

Cell growth inhibition by I-1g in A compared to that in B was increased by 25.4% (p<0.01);

$10^{-8}$ mol/L: A $(35.3\pm1.94)\times10^3$, cell growth inhibition was 36.7% (p<0.001)

B $(47.9\pm2.86)\times10^3$, cell growth inhibition was 14.2% (p<0.05)

Cell growth inhibition by I-1g in A compared to that in B was increased by 26.3% (p<0.01);

$10^{-7}$ mol/L: A $(31.7\pm2.13)\times10^3$, cell growth inhibition was 43.2% (p<0.001)

B $(43.1\pm2.03)\times10^3$, cell growth inhibition was 22.8% (p<0.001)

Cell growth inhibition by I-1g in A compared to that in B was increased by 26.5% (p<0.01).

Example 57

Comparative Evaluation of the Cytotoxicity of Compound I-1h in Cultures of Human Breast Adenocarcinoma MDA-MB-231 Cell Line Related to Dilutions of its Initial Solution in Saline with 2.3 mM $CaCl_2$ (A) and Normal Saline (B).

Aliquots of a stock solution of the sodium salt of compound I-1h in ethanol-water (2:1, v/v) were evaporated on the rotary evaporator under reduced pressure. The one resulting dried film was dissolved in saline with 2.3 mM $CaCl_2$ and other dissolved in normal saline to form initial solutions of compound I-1h in a concentration of $10^{-3}$ M. The two working solutions of compound I-1h in saline with 2.3 mM $CaCl_2$ (A) and normal saline (B) in a concentration of $10^{-5}$ M were prepared from these initial solutions.

Cultures of MDA-MB-231 cells were treated with drug solutions on day 1 after seeding. Aliquots of working solutions (2 μL) with different concentrations of compound I-1h in saline with 2.3 mM $CaCl_2$ (A) and normal saline (B) were added to 200 μL cultures to a final concentrations of compound I-1h from $1\times10^{-9}$ to $1\times10^{-7}$ mol/L in the cultures. After cultivation for two consecutive days, the number of viable cells in cultures was counted and the extent of growth inhibition of MDA-MB-231 cells calculated in order to evaluate the cytotoxicity of the tested solutions of compound I-1h.

After three days of cultivation, the control cultures contained $(55.8\pm1.37)\times10^3$ cells.

The cultures, treated by solutions of compound I-1h in A and in B had the following number of viable cells:

$10^{-9}$ mol/L: A $(40.9\pm2.47)\times10^3$, cell growth inhibition was 26.7% (p<0.001)

B $(51.9\pm3.46)\times10^3$, cell growth inhibition was 7.0% (p>0.05)

Cell growth inhibition by I-1h in A compared to that in B was increased by 21.1% (p<0.05);

$10^{-8}$ mol/L: A $(36.7\pm2.04)\times10^3$, cell growth inhibition was 34.2% (p<0.001)

B $(46.1\pm2.65)\times10^3$, cell growth inhibition was 17.4% (p<0.02)

Cell growth inhibition by I-1h in A compared to that in B was increased by 20.4% (p<0.02);

$10^{-7}$ mol/L: A $(32.5\pm1.26)\times10^3$, cell growth inhibition was 41.8% (p<0.001)

B $(41.3\pm0.99)\times10^3$, cell growth inhibition was 26.0% (p<0.001)

Cell growth inhibition by I-1h in A compared to that in B was increased by 21.3% (p<0.001).

Example 58

Comparative Evaluation of the Cytotoxicity of Compound I-3f in Cultures of Human Breast Adenocarcinoma MDA-MB-231 Cell Line Related to Dilutions of its Initial Solution in Saline with 2.3 mM $CaCl_2$ (A) and Normal Saline (B).

Aliquots of a stock solution of the sodium salt of compound I-3f in ethanol-water (2:1, v/v) were evaporated on the rotary evaporator under reduced pressure. The one resulting dried film was dissolved in saline with 2.3 mM $CaCl_2$ and other dissolved in normal saline to form initial solutions of compound I-3f in a concentration of $10^{-3}$ M. The two working solutions of compound I-3f in saline with 2.3 mM $CaCl_2$ (A) and normal saline (B) in a concentration of $10^{-5}$ M were prepared from these initial solutions.

Cultures of MDA-MB-231 cells were treated with drug solutions on day 1 after seeding. Aliquots of working solutions (2 μL) with different concentrations of compound I-3f in saline with 2.3 mM $CaCl_2$ (A) and normal saline (B) were added to 200 μL cultures to a final concentrations of compound I-3f from $1\times10^{-9}$ to $1\times10^{-7}$ mol/L in the cultures. After cultivation for two consecutive days, the number of viable cells in cultures was counted and the extent of growth inhibition of MDA-MB-231 cells calculated in order to evaluate the cytotoxicity of the tested solutions of compound I-3f.

After three days of cultivation, the control cultures contained $(55.4\pm1.76)\times10^3$ cells.

The cultures, treated by solutions of compound I-3f in A and in B had the following number of viable cells:

$10^{-9}$ mol/L: A $(33.8\pm2.36)\times10^3$, cell growth inhibition was 39.0% (p<0.001)

B $(43.3\pm2.88)\times10^3$, cell growth inhibition was 21.8% (p<0.01)

Cell growth inhibition by I-3f in A compared to that in B was increased by 21.9% (p<0.05);

$10^{-8}$ mol/L: A $(29.5\pm1.14)\times10^3$, cell growth inhibition was 46.8% (p<0.001)

B $(37.6\pm1.52)\times10^3$, cell growth inhibition was 32.1% (p<0.001)

Cell growth inhibition by I-3f in A compared to that in B was increased by 21.5% (p<0.002);

$10^{-7}$ mol/L: A $(25.7\pm0.90)\times10^3$, cell growth inhibition was 53.6% (p<0.001)

B $(32.8\pm0.99)\times10^3$, cell growth inhibition was 40.8% (p<0.001)

Cell growth inhibition by I-3f in A compared to that in B was increased by 21.6% (p<0.001).

Example 59

Comparative Evaluation of the Cytotoxicity of Compound II-3b in Cultures of Human Breast Adenocarcinoma MDA-MB-231 Cell Line Related to Dilutions of its Initial Solution in Saline with 2.3 mM $CaCl_2$ (A) and Normal Saline (B).

Aliquots of a stock solution of the sodium salt of compound II-3b in ethanol-water (2:1, v/v) were evaporated on the rotary evaporator under reduced pressure. The one resulting dried film was dissolved in saline with 2.3 mM $CaCl_2$ and other dissolved in normal saline to form initial solutions of compound II-3b in a concentration of $10^{-3}$ M. The two working solutions of compound II-3b in saline with 2.3 mM $CaCl_2$ (A) and normal saline (B) in a concentration of $10^{-5}$ M were prepared from these initial solutions.

Cultures of MDA-MB-231 cells were treated with drug solutions on day 1 after seeding. Aliquots of working solutions (2 μL) with different concentrations of compound II-3b in saline with 2.3 mM $CaCl_2$ (A) and normal saline (B) were added to 200 μL cultures to a final concentrations of compound II-3b from $1\times10^{-9}$ to $1\times10^{-7}$ mol/L in the cultures. After cultivation for two consecutive days, the number of viable cells in cultures was counted and the extent of growth inhibition of MDA-MB-231 cells calculated in order to evaluate the cytotoxicity of the tested solutions of compound II-3b.

After three days of cultivation, the control cultures contained $(55.4\pm1.76)\times10^3$ cells.

The cultures, treated by solutions of compound II-3b in A and in B had the following number of viable cells:

$10^{-9}$ mol/L: A $(29.9\pm1.23)\times10^3$, cell growth inhibition was 46.0% ($p<0.001$)

B $(41.4\pm2.15)\times10^3$, cell growth inhibition was 25.3% ($p<0.001$)

Cell growth inhibition by II-3b in A compared to that in B was increased by 27.8% ($p<0.001$);

$10^{-8}$ mol/L: A $(25.7\pm1.13)\times10^3$, cell growth inhibition was 53.6% ($p<0.001$)

B $(35.6\pm1.97)\times10^3$, cell growth inhibition was 35.7% ($p<0.001$)

Cell growth inhibition by II-3b in A compared to that in B was increased by 27.8% ($p<0.002$);

$10^{-7}$ mol/L: A $(21.9\pm0.98)\times10^3$, cell growth inhibition was 60.5% ($p<0.001$)

B $(30.8\pm1.60)\times10^3$, cell growth inhibition was 44.4% ($p<0.001$)

Cell growth inhibition by II-3b in A compared to that in B was increased by 28.9% ($p<0.001$).

Example 60

Comparative Evaluation of the Cytotoxicity of Compound II-1a in Cultures of Human Lung Carcinoma A549 Cell Line Related to Dilutions of its Initial Solution in Saline with 2.3 mM $CaCl_2$ (A) and Normal Saline (B).

Aliquots of a stock solution of the sodium salt of compound II-1a in ethanol-water (2:1, v/v) were evaporated on the rotary evaporator under reduced pressure. The one resulting dried film was dissolved in saline with 2.3 mM $CaCl_2$ and other dissolved in normal saline to form initial solutions of compound II-1a in a concentration of $10^{-3}$ M. The two working solutions of compound II-1a in saline with 2.3 mM $CaCl_2$ (A) and normal saline (B) in a concentration of $10^{-5}$ M were prepared from these initial solutions.

Cultures of A549 cells were treated with drug solutions on day 1 after seeding. Aliquots of working solutions (2 μL) with different concentrations of compound II-1a in saline with 2.3 mM $CaCl_2$ (A) and normal saline (B) were added to 200 μL cultures to a final concentrations of compound II-1a from $1\times10^{-9}$ to $1\times10^{-7}$ mol/L in the cultures. After cultivation for two consecutive days, the number of viable cells in cultures was counted and the extent of growth inhibition of A549 cells calculated in order to evaluate the cytotoxicity of the tested solutions of compound II-1a.

After three days of cultivation, the control cultures contained $(55.8\pm1.90)\times10^3$ cells.

The cultures, treated by solutions of compound II-1a in A and in B had the following number of viable cells:

$10^{-9}$ mol/L: A $(44.4\pm2.03)\times10^3$, cell growth inhibition was 20.4% ($p<0.002$)

B $(51.8\pm2.48)\times10^3$, cell growth inhibition was 7.2% ($p>0.05$)

Cell growth inhibition by II-1a in A compared to that in B was increased by 14.3% ($p<0.05$);

$10^{-8}$ mol/L: A $(40.8\pm1.14)\times10^3$, cell growth inhibition was 26.9% ($p<0.001$)

B $(47.1\pm1.43)\times10^3$, cell growth inhibition was 15.6% ($p<0.01$)

Cell growth inhibition by II-1a in A compared to that in B was increased by 13.4% ($p<0.01$);

$10^{-7}$ mol/L: A $(36.6\pm1.13)\times10^3$, cell growth inhibition was 34.4% ($p<0.001$)

B $(41.5\pm1.80)\times10^3$, cell growth inhibition was 25.6% ($p<0.001$)

Cell growth inhibition by II-1a in A compared to that in B was increased by 11.8% ($p<0.05$).

Example 61

Comparative Evaluation of the Cytotoxicity of the Formulation Docetaxel/Compound I-1a+Compound II-1a in Cultures of Human Breast Adenocarcinoma MDA-MB-231 Cell Line at Molar Ratio of Docetaxel:(Compound I-1a+Compound II-1a) of 1: (2.5+2.5) Related to Dilutions of its Initial Solution in Saline with 2.3 mM $CaCl_2$ (A), Normal Saline (B) and Culture Medium with 5% FBS (C).

Aliquots of a stock solutions of the sodium salt of compound I-1a and the sodium salt of compound II-1a in ethanol-water (2:1, v/v) were mixed and evaporated on the rotary evaporator under reduced pressure. The resulting dried films were dissolved in methanol. An equal aliquots of solution of docetaxel in methanol were added to three identical solutions, containing compound I-1a and compound II-1a in methanol to form a solutions with the desired molar ratio of docetaxel:(compound I-1a+ compound II-1a) of 1: (2.5+2.5). After stirring the organic solvent was evaporated. One of the resulting dried films was dissolved in saline with 2.3 mM $CaCl_2$ and the others dissolved in normal saline. The concentration of docetaxel was equal to $10^{-3}$ M in three initial solutions of the formulation. The three working solutions of formulation in saline with 2.3 mM $CaCl_2$ (A), normal saline (B) and medium with 5% FBS (C) were prepared from these initial solutions for adding to cultures. The concentration of docetaxel was equal to $10^{-5}$ M in three working solutions.

Cultures of MDA-MB-231 cells were treated with drug solutions on day 1 after seeding. Aliquots of working solutions (2 μL) with different concentrations of formulation in saline with 2.3 mM $CaCl_2$ (A), normal saline (B) and medium with 5% FBS (C) were added to 200 μL cultures to a final concentration of docetaxel $1\times10^{-9}$, $1\times10^{-8}$ and $1\times10^{-7}$ mol/L in the cultures.

After cultivation for two consecutive days, the number of viable cells in cultures was counted in order to evaluate the cytotoxicity of the tested solutions of the formulation (Table 17)

TABLE 17

| Drug | Docetaxel, mol/L | Tumor Cell Number, × $10^3$ | Cell Growth Inhibition, % | Positive Effect, % | $IC_{50}$ mol/L (a) |
|---|---|---|---|---|---|
| Negative Control | 0 | 57.9 ± 2.14 | | | |
| Docetaxel | $10^{-9}$ | 36.8 ± 1.70 | 36.4* | | 4.6 × $10^{-9}$ |
| | $10^{-8}$ | 25.3 ± 1.18 | 56.3* | | |
| | $10^{-7}$ | 13.6 ± 0.72 | 76.5* | | |
| Formulation in (A) | $10^{-9}$ | 26.6 ± 0.98 | 54.1* | +27.7* | 8.0 × $10^{-10}$ (b) |
| | $10^{-8}$ | 15.1 ± 0.74 | 73.9* | +40.3* | |
| | $10^{-7}$ | 8.0 ± 0.41 | 86.2* | +41.2* | |
| Formulation in (B) | $10^{-9}$ | 31.1 ± 1.56 | 46.3* | +15.5** | 1.4 × $10^{-9}$ |
| | $10^{-8}$ | 18.9 ± 0.86 | 67.4* | +25.3• | |
| | $10^{-7}$ | 11.2 ± 0.65 | 80.7* | +17.6** | |
| Formulation in (C) | $10^{-9}$ | 26.0 ± 1.31 | 55.1* | +29.3* | 6.0 × $10^{-10}$ (b) |
| | $10^{-8}$ | 13.9 ± 0.62 | 76.0* | +45.1* | |
| | $10^{-7}$ | 7.8 ± 0.53 | 86.5* | +42.6* | |

(a) Cell growth inhibition data, determined at three different concentrations, were used to calculate the drug concentrations that inhibited cell growth by 50% as compared to untreated control cultures. All data are the means of three determinations each in six replicates.
(b) Extrapolated
*$p < 0.001$
**$p < 0.05$
•$p < 0.002$

Example 62

Comparative Evaluation of the Cytotoxicity of the Formulation Doxorubicin/Compound I-1a+Compound II-1a in Cultures of Human Breast Adenocarcinoma MDA-MB-231 Cell Line at Molar Ratio of Doxorubicin:(Compound I-1a+Compound II-1a) of 1:(1.5+1.5) Related to Dilutions of its Initial Solution in Saline with 2.3 mM CaCl$_2$ (A), Normal Saline (B) and Culture Medium with 5% FBS (C).

Aliquots of a stock solutions of the sodium salt of compound I-1a and the sodium salt of compound II-1a in ethanol-water (2:1, v/v) were mixed and evaporated on the rotary evaporator under reduced pressure. The resulting dried films were dissolved in water. An equal aliquots of solution of doxorubicin in water were added to three identical solutions, containing compound I-1a and compound II-1a in water to form an initial solutions of the formulation with the desired molar ratio of doxorubicin:(compound I-1a+compound II-1a) of 1:(1.5+1.5). The concentration of doxorubicin was equal to $10^{-3}$ M in three initial solutions of the formulation.

The three working solutions of formulation in saline with 2.3 mM CaCl$_2$ (A), normal saline (B) and medium with 5% FBS (C) were prepared from these initial solutions for adding to cultures. The concentration of doxorubicin was equal to $10^{-5}$ M in three working solutions.

Cultures of MDA-MB-231 cells were treated with drug solutions on day 1 after seeding. Aliquots of working solutions (2 µL) with different concentrations of formulation in saline with 2.3 mM CaCl$_2$ (A), normal saline (B) and medium with 5% FBS (C) were added to 200 µL cultures to a final concentration of doxorubicin $1\times10^{-9}$, $1\times10^{-8}$ and $1\times10^{-7}$ mol/L in the culture After cultivation for two consecutive days, the number of viable cells in cultures was counted in order to evaluate the cytotoxicity of the tested solutions of the formulation (Table 18).

TABLE 18

| Drug | Doxorubicin, mol/L | Tumor Cell Number, × $10^3$ | Cell Growth Inhibition, % | Positive Effect, % | $IC_{50}$ mol/L (a) |
|---|---|---|---|---|---|
| Negative Control | 0 | 57.2 ± 1.60 | | | |
| Doxorubicin | $10^{-9}$ | 46.1 ± 2.07 | 19.4• | | 6.2 × $10^{-8}$ |
| | $10^{-8}$ | 40.4 ± 1.65 | 29.4* | | |
| | $10^{-7}$ | 25.5 ± 0.71 | 55.4* | | |
| Formulation in (A) | $10^{-9}$ | 30.3 ± 1.87 | 47.0* | +34.3* | 3.4 × $10^{-9}$ |
| | $10^{-8}$ | 26.0 ± 1.08 | 54.5* | +35.6* | |
| | $10^{-7}$ | 13.2 ± 0.25 | 76.9* | +48.2* | |
| Formulation in (B) | $10^{-9}$ | 38.3 ± 1.34 | 33.0* | +16.9** | 2.2 × $10^{-8}$ |
| | $10^{-8}$ | 33.1 ± 1.31 | 42.1* | +18.1** | |
| | $10^{-7}$ | 19.2 ± 1.14 | 66.4* | +24.7* | |
| Formulation in (C) | $10^{-9}$ | 29.5 ± 1.26 | 48.4* | +36.0* | 1.8 × $10^{-9}$ |
| | $10^{-8}$ | 25.3 ± 0.24 | 55.8* | +37.4* | |
| | $10^{-7}$ | 12.5 ± 0.69 | 78.1* | +51.0* | |

(a) Cell growth inhibition data, determined at three different concentrations, were used to calculate the drug concentrations that inhibited cell growth by 50% as compared to untreated control cultures. All data are the means of three determinations each in six replicates.
*$p < 0.001$
**$p < 0.01$
•$p < 0.002$

Example 63

Comparative Evaluation of the Cytotoxicity of the Formulation Doxorubicin/Compound I-1f in Cultures of Human Breast Adenocarcinoma MDA-MB-231 Cell Line at Molar Ratio of Doxorubicin:Compound I-1f (1:3) Related to Dilutions of its Initial Solution in Saline with 2.3 mM $CaCl_2$ (A), Normal Saline (B) and Culture Medium with 5% FBS (C).

Aliquots of a stock solution of the sodium salt of compound I-1f in ethanol-water (2:1, v/v) were evaporated on the rotary evaporator under reduced pressure. The resulting dried films were dissolved in water. An equal aliquots of solution of doxorubicin in water were added to three identical solutions, containing compound I-1f in water to form an initial solutions of the formulation with the desired molar ratio of doxorubicin:compound I-1f (1:3). The concentration of doxorubicin was equal to $10^{-3}$ M in three initial solutions of formulation.

The three working solutions of formulation in saline with 2.3 mM $CaCl_2$ (A), normal saline (B) and medium with 5% FBS (C) were prepared from these initial solutions for adding to cultures. The concentration of doxorubicin was equal to $10^{-5}$ M in three working solutions.

Cultures of MDA-MB-231 cells were treated with drug solutions on day 1 after seeding. Aliquots of working solutions (2 µL) with different concentrations of formulation in saline with 2.3 mM $CaCl_2$ (A), normal saline (B) and medium with 5% FBS (C) were added to 200 µL cultures to a final concentration of doxorubicin $1 \times 10^{-9}$, $1 \times 10^{-8}$ and $1 \times 10^{-7}$ mol/L in the culture After cultivation for two consecutive days, the number of viable cells in cultures was counted in order to evaluate the cytotoxicity of the tested solutions of the formulation (Table 19).

Example 64

Comparative Evaluation of the Cytotoxicity of the Formulation Docetaxel/Compound I-1a+Compound II-1a in Cultures of Human Lung Carcinoma A549 Cell Line at Molar Ratio of Docetaxel:(Compound I-1a+Compound II-1a) of 1:(2.5+2.5) Related to Dilutions of its Initial Solution in Saline with 2.3 mM $CaCl_2$ (A), Normal Saline (B) and Culture Medium with 5% FBS (C).

Aliquots of a stock solutions of the sodium salt of compound I-1a and the sodium salt of compound II-1a in ethanol-water (2:1, v/v) were mixed and evaporated on the rotary evaporator under reduced pressure. The resulting dried films were dissolved in methanol. An equal aliquots of solution of docetaxel in methanol were added to three identical solutions, containing compound I-1a and compound II-1a in methanol to form a solutions with the desired molar ratio of docetaxel:(compound I-1a+compound II-1a) of 1: (2.5+2.5). After stirring the organic solvent was evaporated. The one resulting dried film was dissolved in saline with 2.3 mM $CaCl_2$ and others dissolved in normal saline. The concentration of docetaxel was equal to $10^{-3}$ M in three initial solutions of the formulation. The three working solutions of formulation in saline with 2.3 mM $CaCl_2$ (A), normal saline (B) and medium with 5% FBS (C) were prepared from these initial solutions for adding to cultures. The concentration of docetaxel was equal to $10^{-5}$ M in three working solutions.

Cultures of A549 cells were treated with drug solutions on day 1 after seeding. Aliquots of working solutions (2 µL) with different concentrations of formulation in saline with 2.3 mM $CaCl_2$ (A), normal saline (B) and medium with 5%

TABLE 19

| Drug | Doxorubicin, mol/L | Tumor Cell Number, $\times 10^3$ | Cell Growth Inhibition, % | Positive Effect, % | $IC_{50}$ mol/L (a) |
|---|---|---|---|---|---|
| Negative Control | 0 | 56.4 ± 1.78 | | | |
| Doxorubicin | $10^{-9}$ | 45.6 ± 1.38 | 19.1* | | $6.4 \times 10^{-8}$ |
| | $10^{-8}$ | 41.0 ± 0.96 | 27.3* | | |
| | $10^{-7}$ | 25.2 ± 1.56 | 55.3* | | |
| Formulation in (A) | $10^{-9}$ | 30.3 ± 1.55 | 46.3* | +33.6* | $3.7 \times 10^{-9}$ |
| | $10^{-8}$ | 25.5 ± 1.15 | 54.8* | +37.8* | |
| | $10^{-7}$ | 10.8 ± 0.55 | 80.9* | +57.1* | |
| Formulation in (B) | $10^{-9}$ | 36.7 ± 1.07 | 34.9* | +19.5* | $2.1 \times 10^{-8}$ |
| | $10^{-8}$ | 32.6 ± 0.93 | 42.2* | +20.5* | |
| | $10^{-7}$ | 16.8 ± 0.91 | 70.2* | +33.3* | |
| Formulation in (C) | $10^{-9}$ | 29.5 ± 1.14 | 47.7* | +35.3* | $2.1 \times 10^{-9}$ |
| | $10^{-8}$ | 24.6 ± 0.53 | 56.4* | +40.0* | |
| | $10^{-7}$ | 10.0 ± 0.42 | 82.3* | +60.3* | |

(a) Cell growth inhibition data, determined at three different concentrations, were used to calculate the drug concentrations that inhibited cell growth by 50% as compared to untreated control cultures. All data are the means of three determinations each in six replicates.
*$p < 0.001$ FBS (C) were added to 200 μL cultures to a final concentration of docetaxel $1\times10^{-9}$, $1\times10^{-8}$ and $1\times10^{-7}$ mol/L in the cultures.

After cultivation for two consecutive days, the number of viable cells in cultures was counted in order to evaluate the cytotoxicity of the tested solutions of the formulation (Table 20).

$CaCl_2$, containing sodium salt of compound I-1 and others dissolved in normal saline, containing sodium salt of compound I-1 to form initial solutions of the formulation with desired molar ratio paclitaxel:compound I-1 (1:6). The concentration of paclitaxel was equal to $10^{-3}$ M in all the three initial solutions of the formulation.

TABLE 20

| Drug | Docetaxel, mol/L | Tumor Cell Number, × $10^3$ | Cell Growth Inhibition, % | Positive Effect, % | $IC_{50}$ mol/L (a) |
|---|---|---|---|---|---|
| Negative Control | 0 | 55.8 ± 1.90 | | | |
| Docetaxel | $10^{-9}$ | 35.7 ± 1.51 | 36.0* | | $2.2 \times 10^{-9}$ |
|  | $10^{-8}$ | 16.2 ± 0.75 | 71.0* | | |
|  | $10^{-7}$ | 11.0 ± 0.73 | 80.3* | | |
| Formulation in (A) | $10^{-9}$ | 27.9 ± 1.03 | 50.0* | +21.8• | $1.0 \times 10^{-9}$ |
|  | $10^{-8}$ | 9.5 ± 0.53 | 83.0* | +41.4* | |
|  | $10^{-7}$ | 6.6 ± 0.45 | 88.2* | +40.0* | |
| Formulation in (B) | $10^{-9}$ | 32.4 ± 1.64 | 41.9* | +9.2° | $1.5 \times 10^{-9}$ |
|  | $10^{-8}$ | 12.8 ± 0.65 | 77.1* | +21.0** | |
|  | $10^{-7}$ | 8.5 ± 0.60 | 84.8* | +22.7*** | |
| Formulation in (C) | $10^{-9}$ | 27.7 ± 1.22 | 50.4* | +22.4• | $1.0 \times 10^{-9}$ |
|  | $10^{-8}$ | 9.3 ± 0.58 | 83.3* | +42.6* | |
|  | $10^{-7}$ | 6.5 ± 0.47 | 88.4* | +40.9* | |

(a) Cell growth inhibition data, determined at three different concentrations, were used to calculate the drug concentrations that inhibited cell growth by 50% as compared to untreated control cultures. All data are the means of three determinations each in six replicates.
*$p < 0.001$
**$p < 0.01$
***$p < 0.05$
•$p < 0.002$
°$p > 0.05$ Example 65

Comparative Evaluation of the Cytotoxicity of the Formulation Paclitaxel/Compound I-1 in Cultures of Human Breast Adenocarcinoma MDA-MB-231 Cell Line at Molar Ratio of Paclitaxel:Compound I-1 (1:6) Related to Dilutions of its Initial Solution in Saline with 2.3 mM $CaCl_2$ (A), Normal Saline (B) and Culture Medium with 5% FBS (C)

The sodium salt of compound I-1 was converted into the acidic form of compound I-1 and dissolved in methanol. An equal aliquots of solution of paclitaxel in methanol were added to three identical solutions of compound I-1 in methanol to form a solutions with molar ratio of paclitaxel:compound I-1 (1:3).

After stirring the organic solvent was evaporated. The one resulting dried film was dissolved in saline with 2.3 mM The three working solutions of formulation in saline with 2.3 mM $CaCl_2$ (A), normal saline (B) and medium with 5% FBS (C) were prepared from these initial solutions for adding to cultures. The concentration of paclitaxel was equal to $10^{-5}$ M in three working solutions. Cultures of MDA-MB-231 cells were treated with drug solutions on day 1 after seeding. Aliquots of working solutions (2 μL) with different concentrations of formulation in saline with 2.3 mM $CaCl_2$ (A), normal saline (B) and medium with 5% FBS (C) were added to 200 μL cultures to a final concentration of paclitaxel $1\times10^{-9}$, $1\times10^{-8}$ and $1\times10^{-7}$ mol/L in the cultures.

After cultivation for two consecutive days, the number of viable cells in cultures was counted in order to evaluate the cytotoxicity of the tested solutions of the formulation (Table 21).

TABLE 21

| Drug | Paclitaxel, mol/L | Tumor Cell Number, × $10^3$ | Cell Growth Inhibition, % | Positive Effect, % | $IC_{50}$ mol/L (a) |
|---|---|---|---|---|---|
| Negative Control | 0 | 56.8 ± 2.94 | | | |
| Paclitaxel | $10^{-9}$ | 41.3 ± 1.93 | 27.3• | | $1.7 \times 10^{-8}$ |
|  | $10^{-8}$ | 32.2 ± 1.60 | 43.3* | | |
|  | $10^{-7}$ | 16.0 ± 0.72 | 71.8* | | |
| Formulation in (A) | $10^{-9}$ | 29.9 ± 1.06 | 47.4* | +27.6* | $1.5 \times 10^{-9}$ |
|  | $10^{-8}$ | 22.8 ± 0.75 | 59.9* | +29.2* | |
|  | $10^{-7}$ | 9.7 ± 0.42 | 82.9* | +39.4* | |
| Formulation in (B) | $10^{-9}$ | 34.0 ± 1.49 | 40.1* | +17.7*** | $6.0 \times 10^{-9}$ |
|  | $10^{-8}$ | 26.2 ± 0.86 | 53.9* | +18.6** | |
|  | $10^{-7}$ | 11.9 ± 0.61 | 79.0* | +25.6• | |

TABLE 21-continued

| Drug | Paclitaxel, mol/L | Tumor Cell Number, × 10³ | Cell Growth Inhibition, % | Positive Effect, % | IC$_{50}$ mol/L (a) |
|---|---|---|---|---|---|
| Formulation in (C) | $10^{-9}$ | 29.2 ± 0.94 | 48.6* | +29.3* | $1.2 \times 10^{-9}$ |
| | $10^{-8}$ | 22.3 ± 0.89 | 60.7* | +30.7* | |
| | $10^{-7}$ | 9.3 ± 0.38 | 83.6* | +41.9* | |

(a) Cell growth inhibition data, determined at three different concentrations, were used to calculate the drug concentrations that inhibited cell growth by 50% as compared to untreated control cultures. All data are the means of three determinations each in six replicates.
*p < 0.001
**p < 0.01
***p < 0.02
•p < 0.002

Example 66

Comparative Evaluation of the Cytotoxicity of the Formulation Paclitaxel/Compound I-1a+Compound II-1a in Cultures of Human Breast Adenocarcinoma MDA-MB-231 Cell Line at Molar Ratio of Paclitaxel:(Compound I-1a+Compound II-1A) of 1: (2.5+2.5) Related to Dilutions of its Initial Solution in Saline with 2.3 mM CaCl$_2$ (A), Normal Saline (B) and Culture Medium with 5% FBS (C).

Aliquots of a stock solutions of the sodium salt of compound I-1a and the sodium salt of compound II-1a in ethanol-water (2:1, v/v) were mixed and evaporated on a rotary evaporator under reduced pressure. The resulting dried films were dissolved in methanol. An equal aliquots of solution of paclitaxel in methanol were added to three identical solutions, containing compound I-1a and compound II-1a in methanol to form a solutions with the desired molar ratio of paclitaxel:(compound I-1a+compound II-1a) of 1:(2.5+2.5). After stirring the organic solvent was evaporated. The one resulting dried film was dissolved in saline with 2.3 mM CaCl$_2$ and others dissolved in normal saline. The concentration of paclitaxel was equal to $10^{-3}$ M in all three initial solutions of the formulation. The three working solutions of formulation in saline with 2.3 mM CaCl$_2$ (A), normal saline (B) and medium with 5% FBS (C) were prepared from these initial solutions for adding to cultures. The concentration of paclitaxel was equal to $10^{-5}$ M in all three working solutions.

Cultures of MDA-MB-231 cells were treated with drug solutions on day 1 after seeding. Aliquots of working solutions (2 μL) with different concentrations of formulation in saline with 2.3 mM CaCl$_2$ (A), normal saline (B) and medium with 5% FBS (C) were added to 200 μL cultures to a final concentration of paclitaxel $1\times10^{-9}$, $1\times10^{-8}$ and $1\times10^{-7}$ mol/L in the culture After cultivation for two consecutive days, the number of viable cells in cultures was counted in order to evaluate the cytotoxicity of the tested solutions of the formulation (Table 22).

TABLE 22

| Drug | Paclitaxel, mol/L | Tumor Cell Number, × 10³ | Cell Growth Inhibition, % | Positive Effect, % | IC$_{50}$ mol/L (a) |
|---|---|---|---|---|---|
| Negative Control | 0 | 58.5 ± 1.76 | | | |
| Paclitaxel | $10^{-9}$ | 42.3 ± 1.55 | 27.7* | | $1.7 \times 10^{-8}$ |
| | $10^{-8}$ | 32.8 ± 1.07 | 43.9* | | |
| | $10^{-7}$ | 16.6 ± 0.86 | 71.6* | | |
| Formulation in (A) | $10^{-9}$ | 31.6 ± 1.24 | 46.0* | +25.3* | $2.2 \times 10^{-9}$ |
| | $10^{-8}$ | 24.4 ± 1.06 | 58.3* | +25.6* | |
| | $10^{-7}$ | 9.1 ± 0.43 | 84.4* | +45.2* | |
| Formulation in (B) | $10^{-9}$ | 36.8 ± 1.94 | 37.1* | +13.0• | $8.0 \times 10^{-9}$ |
| | $10^{-8}$ | 28.1 ± 1.19 | 52.0* | +14.3*** | |
| | $10^{-7}$ | 12.4 ± 0.85 | 78.8* | +25.3** | |
| Formulation in (C) | $10^{-9}$ | 31.0 ± 1.36 | 47.0* | +26.7* | $1.7 \times 10^{-9}$ |
| | $10^{-8}$ | 23.7 ± 0.81 | 59.5* | +27.7* | |
| | $10^{-7}$ | 8.7 ± 0.52 | 85.1 | +47.6* | |

(a) Cell growth inhibition data, determined at three different concentrations, were used to calculate the drug concentrations that inhibited cell growth by 50% as compared to untreated control cultures. All data are the means of three determinations each in six replicates.
*p < 0.001
**p < 0.01
***p < 0.02
•p < 0.05

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto.

REFERENCES

L. Collins-Gold, et al., Modern Drug Discovery, 2000, Vol. 3, No. 3, p. 44–46, 48
J. E. Cortes, R. Pazdur, J. Clin. Oncology, 1995, v. 13, p. 2643–2655
D. Faulds et al., Drugs, 1991, v. 41, No. 3, p. 400–449
D. A. Gewirtz, Biochem. Pharmacol., 1999, v. 57, No. 7, p. 727–741
C. L. Vogel, J -M. Nabholtz, The Oncologist, 1999, v. 4, p. 17–33

The invention claimed is:
1. A compound having the structural formula

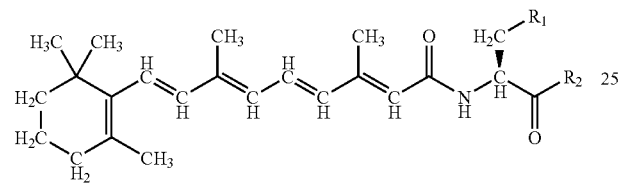

(I)

or

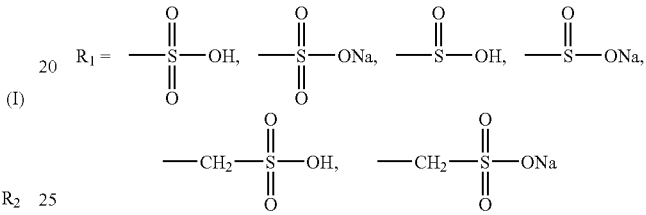

(II)

wherein $R_1$ is chosen among

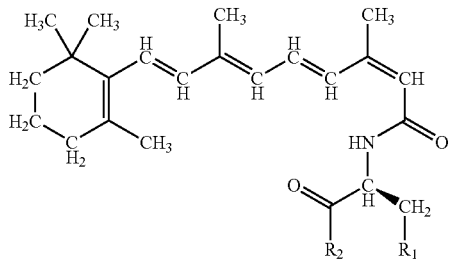

and $R_2$ is chosen among $NH_2$, $NHCH_3$, $N(CH_3)_2$ or OX wherein X is a $C_1$–$C_4$ among alkyl.

2. A compound according to claim 1, wherein the compound is selected from the group consisting of:

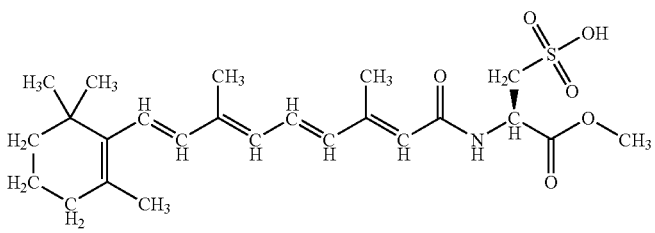

(I-1a)

N-(all-trans-retinoyl)-L-cysteic acid methyl ester

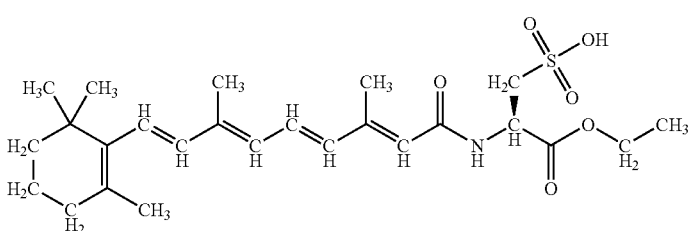

(I-1b)

N-(all-trans-retinoyl)-L-cysteic acid ethyl ester

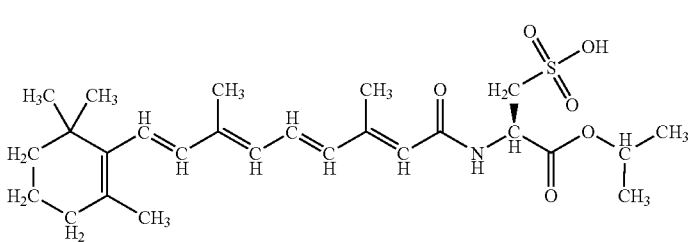

(I-1c)

N-(all-trans-retinoyl)-L-cysteic acid isopropyl ester

-continued
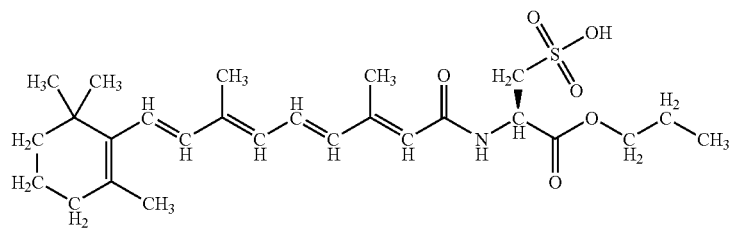
N-(all-trans-retinoyl)-L-cysteic acid propyl ester (I-1d)
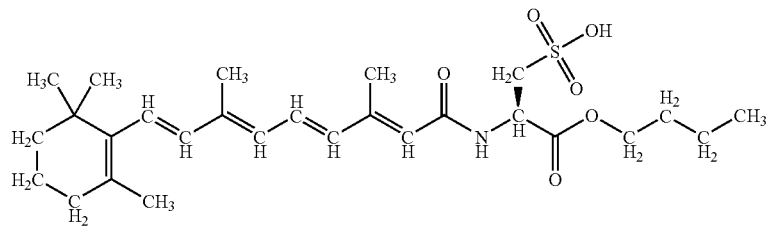
N-(all-trans-retinoyl)-L-cysteic acid butyl ester (I-1e)
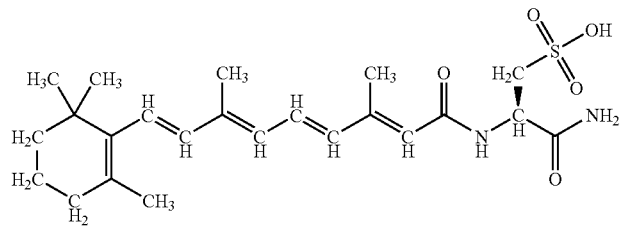
N-(all-trans-retinoyl)-L-cysteic acid amide (I-1f)
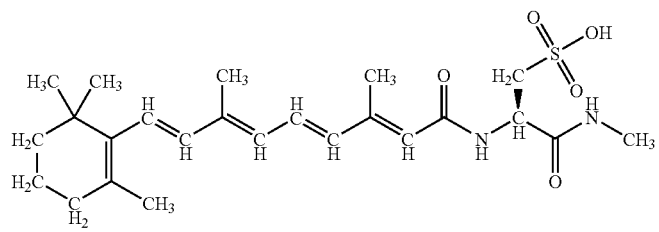
N-(all-trans-retinoyl)-L-cysteic acid methylamide (I-1g)
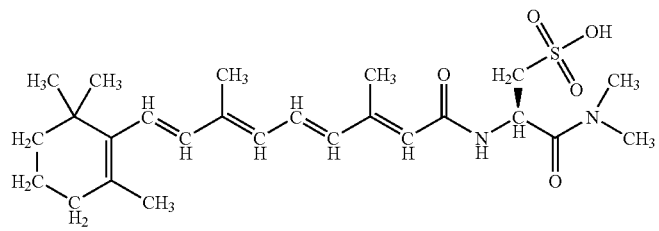
N-(all-trans-retinoyl)-L-cysteic acid dimethylamide (I-1h)
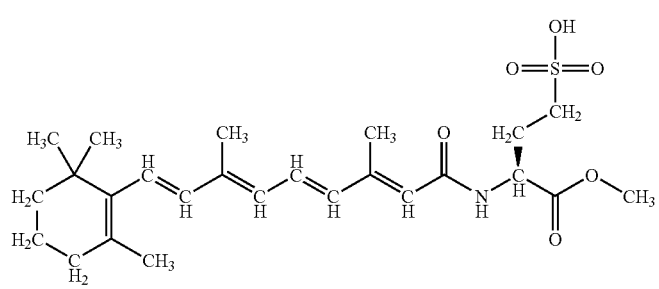
N-(all-trans-retinoyl)-L-homocysteic acid methyl ester (I-3a)

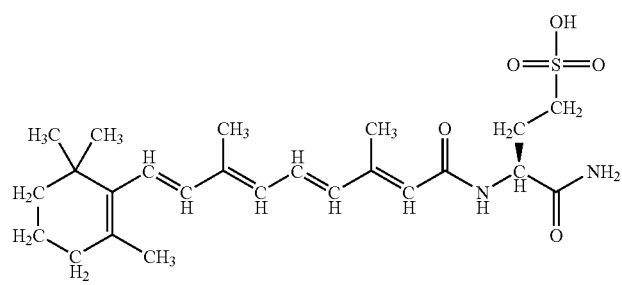
N-(all-trans-retinoyl)-L-homocysteic acid amide (I-3f)
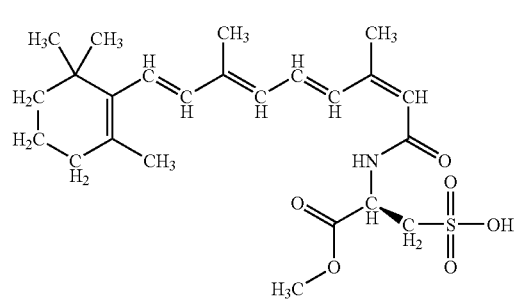
N-(13-cis-retinoyl)-L-cysteic acid methyl ester (II-1a)
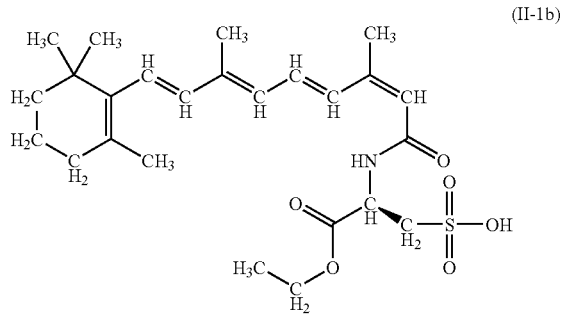
N-(13-cis-retinoyl)-L-cysteic acid ethyl ester (II-1b)
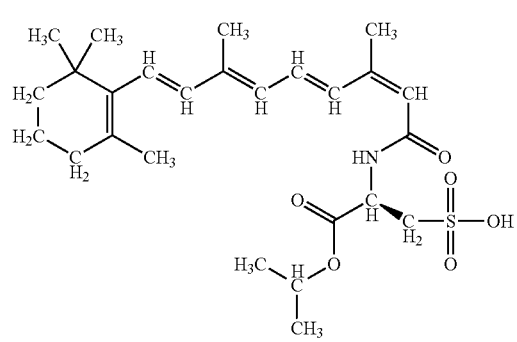
N-(13-cis-retinoyl)-L-cysteic acid isopropyl ester (II-1c)
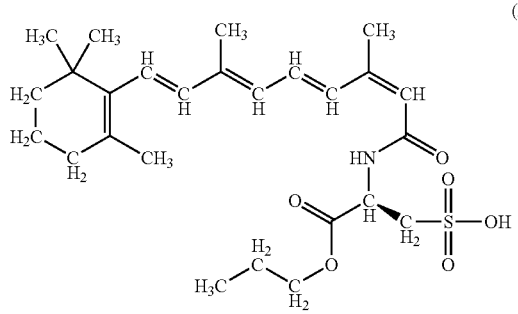
N-(13-cis-retinoyl)-L-cysteic acid propyl ester (II-1d)
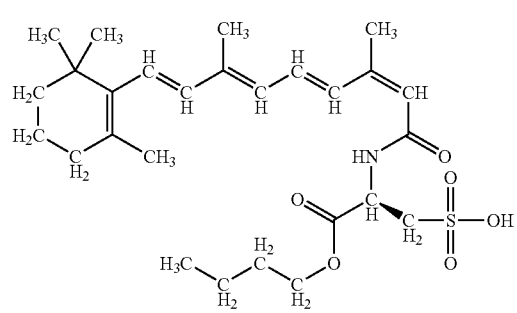
N-(13-cis-retinoyl)-L-cysteic acid butyl ester (II-1e)
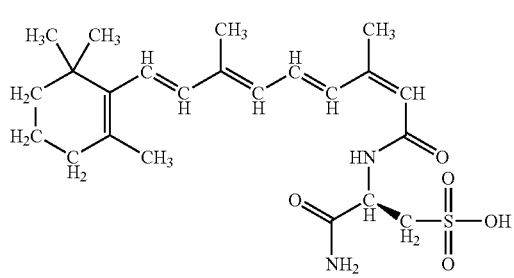
N-(13-cis-retinoyl)-L-cysteic acid amide (II-1f)

(II-3b)

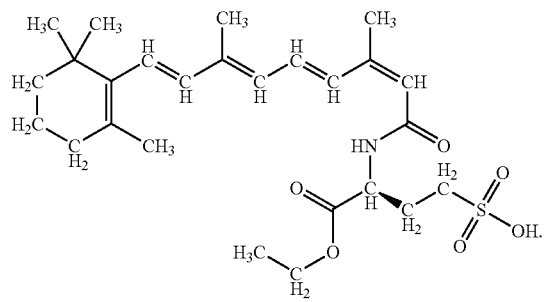

N-(13-cis-retinoyl)-L-homocysteic acid ethyl ester

3. A pharmaceutically acceptable salt of a compound according to claim 1.

4. A pharmaceutically acceptable salt of a compound according to claim 2.

5. A pharmaceutically acceptable sodium salt of a compound according to claim 1.

6. A pharmaceutically acceptable sodium salt of a compound according to claim 2.

7. A composition comprising the compound of claim 1.

8. A composition comprising the compound of claim 2.

9. A method of treating cancer, comprising administering the compound of claim 1 to a patient.

10. A method of treating cancer, comprising administering the compound of claim 2 to a patient.

11. A pharmaceutical composition comprising at least one of the compounds of claim 1 in an aqueous saline solution containing calcium ions.

12. A pharmaceutical composition comprising at least one of the compounds of claim 2 in an aqueous saline solution containing calcium ions.

13. A pharmaceutical composition according to claim 11, wherein the concentration of calcium ions is about 2.2 to 2.6 mmol/L $CaCl_2$.

14. A pharmaceutical composition according to claim 12, wherein the concentration of calcium ions is about 2.2 to 2.6 mmol/L $CaCl_2$.

15. A pharmaceutical composition according to claim 13, wherein the concentration of calcium ions is 2.3 mmol/L $CaCl_2$.

16. A pharmaceutical composition according to claim 14, wherein the concentration of calcium ions is 2.3 mmol/L $CaCl_2$.

17. A pharmaceutical composition according to claim 11, wherein at least one of the compounds is present in both cis- and trans-form.

18. A pharmaceutical composition according to claim 12, wherein at least one of the compounds is present in both cis- and trans-form.

19. A pharmaceutical composition comprising a compound of claim 1, further including an active substance.

20. A pharmaceutical composition according to claim 19, wherein the active substance is a cytotoxic compound.

21. A pharmaceutical composition according to claim 19, wherein the active substance is selected from the group consisting of docetaxel, paclitaxel, doxorubicin and mitoxantrone.

22. A pharmaceutical composition according to claim 19, wherein the active substance is paclitaxel present in the form of Taxol®.

23. A pharmaceutical composition according to claim 19, wherein the compound is present in the form of its sodium salt or is present in acid form.

24. A method for potentiating the efficacy of a pharmaceutically active substance, wherein the substance is prepared in micellar form with a compound according to claim 1.

25. A method for increasing the solubility of a pharmaceutically active substance, wherein the substance is prepared in micellar form with a compound according to claim 1.

26. A method for improving the bio-availability of a pharmaceutically active substance, wherein the substance is prepared in micellar form with a compound according to claim 1.

27. A method for improving the storage properties of a pharmaceutically active substance, wherein the substance is prepared in micellar form with a compound according to claim 1.

28. A method for the treatment of cancer, comprising mixing a cytotoxic substance with a compound according to claim 1 to form a mixture and administering said mixture to a patient.

29. The method of claim 28, wherein the cytotoxic substance is selected from the group consisting of docetaxel, paclitaxel, doxorubicin and mitoxantrone.

30. The method of claim 28, wherein the cytotoxic substance is paclitaxel present in the form of Taxol®.

31. The method of claim 28, wherein the compound is present in the form of its sodium salt.

32. The method of claim 28, wherein the compound is present in acid form.

33. A method for the treatment of cancer, comprising administering the pharmaceutical composition of claim 11 to a patient.

34. A method for the treatment of cancer, comprising administering the pharmaceutical composition of claim 12 to a patient.

35. A method for the treatment of cancer, comprising administering the pharmaceutical composition of claim 13 to a patient.

36. A method for the treatment of cancer, comprising administering the pharmaceutical composition of claim 14 to a patient.

37. A method for the treatment of cancer, comprising administering the pharmaceutical composition of claim 15 to a patient.

38. A method for the treatment of cancer, comprising administering the pharmaceutical composition of claim 16 to a patient.

39. A method for the treatment of cancer, comprising administering the pharmaceutical composition of claim 17 to a patient.

40. A method for preparing a water-soluble formulation of a poorly soluble pharmaceutical compound, comprising the steps of:
   (a) dissolving the pharmaceutical compound in a first solvent to form a first solution;
   (b) dissolving a compound according to claim 1 in a second solvent to form a second solution;
   (c) mixing aliquots of the first and second solutions; and
   (d) evaporating the resulting mixture to dryness to prepare a water soluble formulation of said pharmaceutical compound.

41. A method for preparing a stable storage formulation of a poorly soluble pharmaceutical compound, comprising the steps of:
   (a) dissolving the pharmaceutical compound in a first solvent to form a first solution;
   (b) dissolving a compound according to claim 1 in a second solvent to form a second solution;
   (c) mixing aliquots of the first and second solutions in a desired molar ratio to prepare a soluble storage formulation of a pharmaceutical compound.

42. A method for preparing a formulation of a poorly soluble pharmaceutical compound for administration to a patient, comprising the steps of:
   (a) dissolving a pharmaceutical compound in a first solvent to form a first solution;
   (b) dissolving a compound according to claim 1 in a second solvent to form a second solution;
   (c) mixing aliquots of the first and second solutions in a desired molar ratio to form a mixture;
   (d) evaporating the mixture to dryness to form a residue of said first compound and said second compound to form a residue;
   (e) dissolving said residue in water to form a dissolved residue; and
   (f) lyophilizing the dissolved residue to form a lyophilized residue and reconstituting the lyophilized residue with a third solvent suitable for administration to a patient.

43. A method according to claim 40, wherein the first and second solvents are at least one aliphatic alcohol.

44. A method according to claim 41, wherein the first and second solvents are at least one aliphatic alcohol.

45. A method according to claim 42, wherein the first and second solvents are at least one aliphatic alcohol.

46. A method according to claim 40, wherein the first and second solvents are ethanol.

47. A method according to claim 41, wherein the first and second solvents are ethanol.

48. A method according to claim 42, wherein the first and second solvents are ethanol.

49. A method according to claim 42, wherein the first and second solvents are at least one aliphatic alcohol and the third solvent is aqueous saline solution containing calcium ions.

* * * * *